United States Patent
Portal

(10) Patent No.: US 10,647,688 B2
(45) Date of Patent: May 12, 2020

(54) COMPOUNDS, SYNTHESIS METHOD THEREOF AND USE OF SAME IN MEDICINE AND IN COSMETICS

(71) Applicant: GALDERMA RESEARCH & DEVELOPMENT, Biot (FR)

(72) Inventor: Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 15/537,549

(22) PCT Filed: Dec. 17, 2015

(86) PCT No.: PCT/FR2015/053581
§ 371 (c)(1),
(2) Date: Jun. 19, 2017

(87) PCT Pub. No.: WO2016/097626
PCT Pub. Date: Jun. 23, 2016

(65) Prior Publication Data
US 2017/0342040 A1    Nov. 30, 2017

(30) Foreign Application Priority Data
Dec. 19, 2014   (FR) ..................................... 14 63033

(51) Int. Cl.
| | | |
|---|---|---|
| *C07D 277/30* | (2006.01) |
| *C07D 231/12* | (2006.01) |
| *C07D 261/08* | (2006.01) |
| *C07D 271/06* | (2006.01) |
| *A61K 8/49* | (2006.01) |
| *C07D 233/64* | (2006.01) |
| *C07D 333/24* | (2006.01) |
| *C07D 207/337* | (2006.01) |
| *C07D 263/32* | (2006.01) |
| *C07D 271/10* | (2006.01) |
| *A61Q 19/00* | (2006.01) |
| *C07D 249/08* | (2006.01) |
| *C07D 285/12* | (2006.01) |
| *A61Q 5/00* | (2006.01) |
| *A61Q 19/08* | (2006.01) |
| *A61Q 7/00* | (2006.01) |
| *C07D 271/107* | (2006.01) |

(52) U.S. Cl.
CPC .............. *C07D 277/30* (2013.01); *A61K 8/49* (2013.01); *A61K 8/494* (2013.01); *A61K 8/4913* (2013.01); *A61K 8/4986* (2013.01); *A61Q 5/008* (2013.01); *A61Q 7/00* (2013.01); *A61Q 19/00* (2013.01); *A61Q 19/007* (2013.01); *A61Q 19/008* (2013.01); *A61Q 19/08* (2013.01); *C07D 207/337* (2013.01); *C07D 231/12* (2013.01); *C07D 233/64* (2013.01); *C07D 249/08* (2013.01); *C07D 261/08* (2013.01); *C07D 263/32* (2013.01); *C07D 271/06* (2013.01); *C07D 271/10* (2013.01); *C07D 271/107* (2013.01); *C07D 285/12* (2013.01); *C07D 333/24* (2013.01); *A61K 2800/522* (2013.01)

(58) Field of Classification Search
CPC .. C07D 277/30; C07D 231/12; C07D 261/08; C07D 271/06; C07D 271/107
See application file for complete search history.

(56) References Cited

U.S. PATENT DOCUMENTS

| | | | | |
|---|---|---|---|---|
| 5,061,705 | A | 10/1991 | Wuest et al. | |
| 5,475,017 | A * | 12/1995 | Wuest ................ | C07D 207/323 424/59 |
| 6,020,339 | A * | 2/2000 | Perrier ................ | C07D 307/42 514/263.23 |
| 6,080,764 | A * | 6/2000 | Chihiro ................ | C07D 277/24 514/342 |
| 6,545,009 | B1 * | 4/2003 | Sugiyama ............ | C07D 263/32 514/277 |
| 8,329,739 | B2 * | 12/2012 | Shibutani ............. | C07D 233/54 514/397 |
| 9,611,230 | B2 * | 4/2017 | Almstead ............ | C07D 231/12 |
| 2011/0275823 | A1 | 11/2011 | Shibutani et al. | |

FOREIGN PATENT DOCUMENTS

| | | | |
|---|---|---|---|
| CN | 1314899 A | 9/2001 | |
| CN | 101076703 A | 11/2007 | |
| CN | 102307861 A | 1/2012 | |
| EP | 1092711 A1 * | 4/2001 | ........... C07D 263/32 |
| EP | 1092711 A1 | 4/2001 | |
| JP | H02-240058 A | 9/1990 | |
| JP | H05-51318 A | 3/1993 | |
| RU | 2497811 C2 | 11/2013 | |
| WO | WO-97/02244 A1 | 1/1997 | |
| WO | 98/08830 A1 | 3/1998 | |
| WO | WO-00/001679 A1 | 1/2000 | |
| WO | WO-03/000249 A1 | 1/2003 | |

(Continued)

OTHER PUBLICATIONS

CAS Abstract amd Indexed Compounds U.S. Pat. No. 5,475,017 (1995).*
T. Yoshizumi et al., 50 Tetrahedron Letters, 3273-3276 (2009).*
L. Duchet et al., 66 Tetrahedron, 986-994 (2010).*
A. Raoof et al., 56 Journal of Medicinal Chemistry, 6352-6370 (2013).*
D. Sinnoni et al., 51 Journal of Medicinal Chemistry, 4796-4803 (2008) (Year: 2008).*
E. Garattini et al., 103 Blood, 194-207 (2004) (Year: 2004).*

(Continued)

*Primary Examiner* — Alexander R Pagano
(74) *Attorney, Agent, or Firm* — Clark & Elbing LLP

(57) ABSTRACT

Novel compounds, synthesis methods and use of the same in medicine and in cosmetics are disclosed. Also disclosed, are novel compounds and ligands that modulate RARs.

29 Claims, No Drawings

(56) References Cited

FOREIGN PATENT DOCUMENTS

Figure 3:
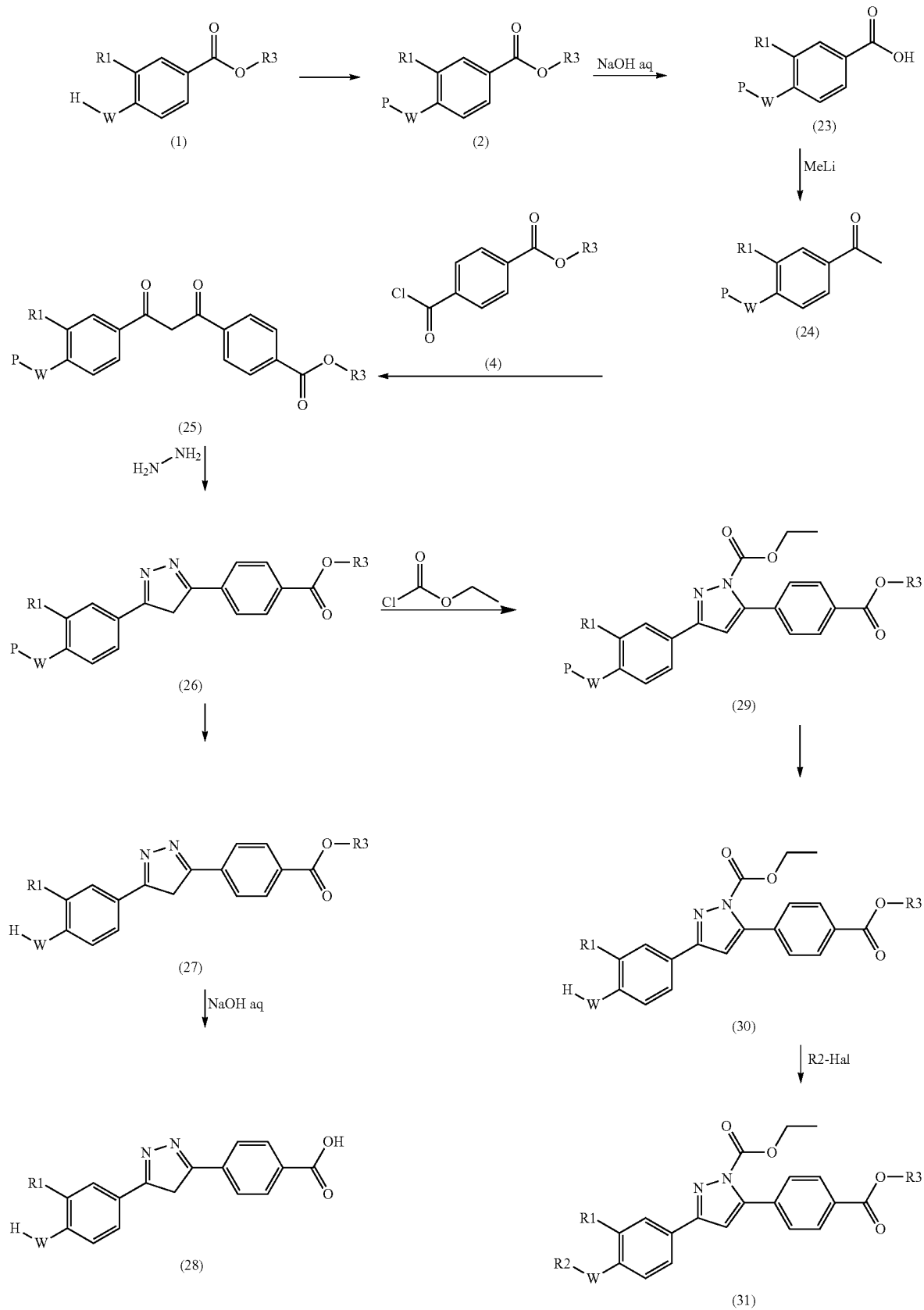

WO  WO-2006044456 A1 *  4/2006  ............ C07D 231/12
WO  WO-2010-090200 A1     8/2010

OTHER PUBLICATIONS

International Search Report and Written Opinion of the International Searching Authority dated Feb. 5, 2016 corresponding to International Patent Application No. PCT/FR2015/053581, 13 pages.
English translation of the International Search Report dated Feb. 5, 2016 corresponding to International Patent Application No. PCT/FR2015/053581, 4 pages.
Garattini, E., et al., "ST1926, a novel an orally active retinoid-related molecule inducing apoptosis in myeloid leukemia cells: modulation of intracellular calcium homeostasis," Blood, vol. 103, No. 1, Jan. 2004, pp. 194-207, XP002498487.
Simoni, D., et al., "Novel Terphenyls and 3,5-Diaryl Isoxazole Derivatives Endowed with Growth Supporting and Antiapoptotic Properties," J. Med. Chem., vol. 51, No. 15, Dec. 2008, pp. 4796-4803, XP002756731.
Garcia-Rodriguez, J., et al., "Inhibition of I[kappa]B and kinase-[beta] and I[kappa]B kinase-[alpha] by heterocyclic adamantyl arotinoids," Bioorg. Med. Chem., vol. 22, No. 4, Jan. 2014, pp. 1285-1302, XP028606349.
Duchet, L., et al., "Synthesis of 3,5-disubstituted 1,2,4-oxadiazoles using ionic liquid-phase organic synthesis (IoLiPOS) methododlogy," Tetrahedron, vol. 66, No. 4, Jan. 2010, pp. 986-994, XP026815260.
Chihiro, M., et al., "Novel Thiazole Derivatives as Inhibitors of Superoxide Production by Human Neutrophils: Synthesis and Structure-Activity Relationships," J. Med. Chem., vol. 38, No. 2, Jan. 1995, pp. 353-358, XP002024855.
Yoshizumi, T., et al., "Synthesis of 2,5-diaryloxazoles through van Leusen reaction and copper-mediated direct arylation," Tetrahendron Letters, vol. 50, No. 26, Jul. 2009, pp. 3273-3276, XP026120479.
Raoof, A., et al., "Toxoflavins and Deazaflavins as the First Reported Selective Small Molecule Inhibitors of Tyrosyl-DNA Phosphodiesterase II," J. Med. Chem., vol. 56, No. 16, pp. 6352-6370, XP0027556732.
Dawson et al., "4-[3-(5,6,7,8-Tetrahydro-5,5,8,8-tetramethyl-2-naphthalenyl)phenyl]benzoic acid and heterocyclic-bridged analogues are novel retinoic acid receptor subtype and retinoid X receptor alpha agonists," Bioorg Med Chem Lett. 10(12):1311-3 (2000).
Simoni et al., "Heterocycle-containing retinoids. Discovery of a novel isoxazole arotinoid possessing potent apoptotic activity in multidrug and drug-induced apoptosis-resistant cells," J Med Chem. 44(14):2308-18 (2001).
Examination Report for Australian Patent Application No. 2015365738, dated Jul. 9, 2019 (6 pages).
Office Action and Translation for Chinese Patent Application No. 2015800764662, dated Jun. 24, 2019 (20 pages).
First Examination Report and English Translation for European Patent Application No. 15832885.6, dated Apr. 15, 2019 (11 pages).
Office Action and English Translation for Israeli Patent Application No. 252934, dated Aug. 4, 2019 (5 pages).
Office Action and English Translation for Japanese Patent Application No. 2017-532890, dated Jul. 1, 2019 (10 pages).
Office Action and English Translation for Russian Patent Application No. 2017125663, dated May 6, 2019 (13 pages).

* cited by examiner

COMPOUNDS, SYNTHESIS METHOD THEREOF AND USE OF SAME IN MEDICINE AND IN COSMETICS

CROSS-REFERENCE TO PRIOR APPLICATIONS

This application is a National Stage of PCT/FR2015/053581, filed Dec. 17, 2015, and designating the United States (published on Jun. 23, 2016, as WO 2016/097626 A1), which claims priority under 35 U.S.C. § 119 to French Application No. 1463033, filed Dec. 19, 2014, each hereby expressly incorporated by reference in its entirety and each assigned to the assignee hereof.

TECHNICAL FIELD

As novel and useful industrial products, the invention relates to novel compounds, ligands that modulate RARs. It also relates to compositions containing them, the preparation methods and the use thereof in pharmaceutical compositions for human or veterinary medicinal use, or even in cosmetic compositions and the non-therapeutic use thereof.

Compounds with a retinoid (vitamin A and its derivatives) activity are widely described in the literature as having activities in the processes of cellular proliferation and differentiation. These properties give this class of compounds a strong potential in the treatment or prevention of many diseases, and particularly in dermatology and cancer. Many biological effects of retinoids are mediated by retinoic acid nuclear receptors (RARs) modulation. RARs activate transcription and are bound to DNA sequence elements called RAR response elements (RARE), in the form of a heterodimer with retinoid X receptors (called RXRs). Three subtypes of human RARs have been identified and described: RARα, RARβ and RARγ.

The prior art contains a large number of chemical ligand compounds for RARs. The documents of the prior art include U.S. Pat. No. 6,150,413 which describes triaromatic compounds, U.S. Pat. No. 6,214,878 which describes stilbene compounds, or U.S. Pat. No. 6,218,128 which describes a family of bicyclic or tricyclic molecules.

The Applicant has invented novel retinoic acid receptor modulator compounds.

Therefore the present invention relates to novel compounds of the following general formula (I),

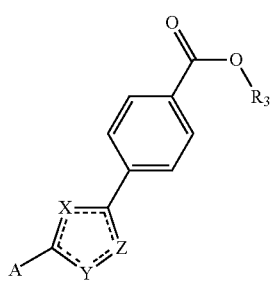

as well as the method of synthesis and use thereof in pharmaceutical compositions for human or veterinary medicinal use, or in cosmetics.

The compounds of the present invention act as modulators of different subtypes of retinoic acid nuclear receptors (RARs).

Therefore, the present invention concerns compounds of formula (I)

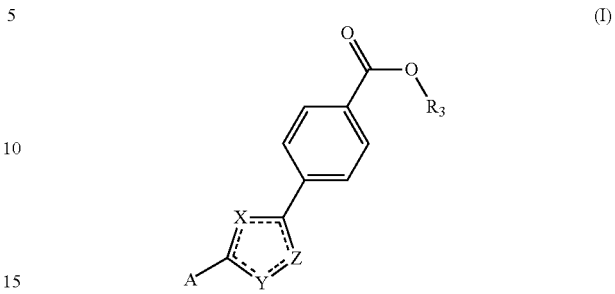

in which:

A represents a group chosen from among:

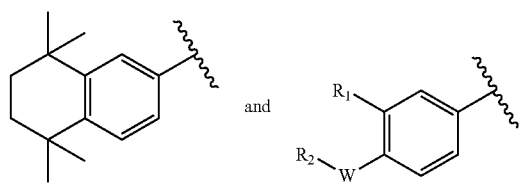

R1 represents a linear or branched alkyl radical, a substituted alkyl radical, a cycloalkyl radical, a substituted cycloalkyl radical, an adamantyl radical, an alkoxyl radical or a $NR_4R_5$ radical;

R2 is a hydrogen atom, a linear or branched alkyl radical, a substituted alkyl radical, a fluorinated alkyl radical, an alkenyl radical, a substituted alkenyl radical, an alkynyl radical, a substituted alkynyl radical, a cycloalkyl-alkyl radical, a polyether radical a mono or polyhydroxyalkyl radical, an aminoalkyl radical, an aralkyl radical, a substituted aralkyl radical, a heteroaralkyl radical or a substituted heteroaralkyl radical.

R3 is a hydrogen or linear or branched alkyl radical;

R4 and R5, identical or different, represent a hydrogen atom, a linear or branched alkyl radical, a substituted alkyl radical, an acyl radical;

R4 and R5, taken together, can also be bound and form an azetidine, pyrrolidine or piperidine heterocycle with the nitrogen atom with which they are linked, this heterocycle can also be substituted;

W represents O, S, NH or CH2;

X, Y, Z, identical or different, represent O, S, N, $NR_6$ or CH;

the central heterocycle

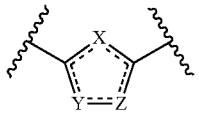

corresponds to one of the structures presented below, the dashed bonds may be a single or double bond depending on the nature of atoms X, Y and Z and their covalence

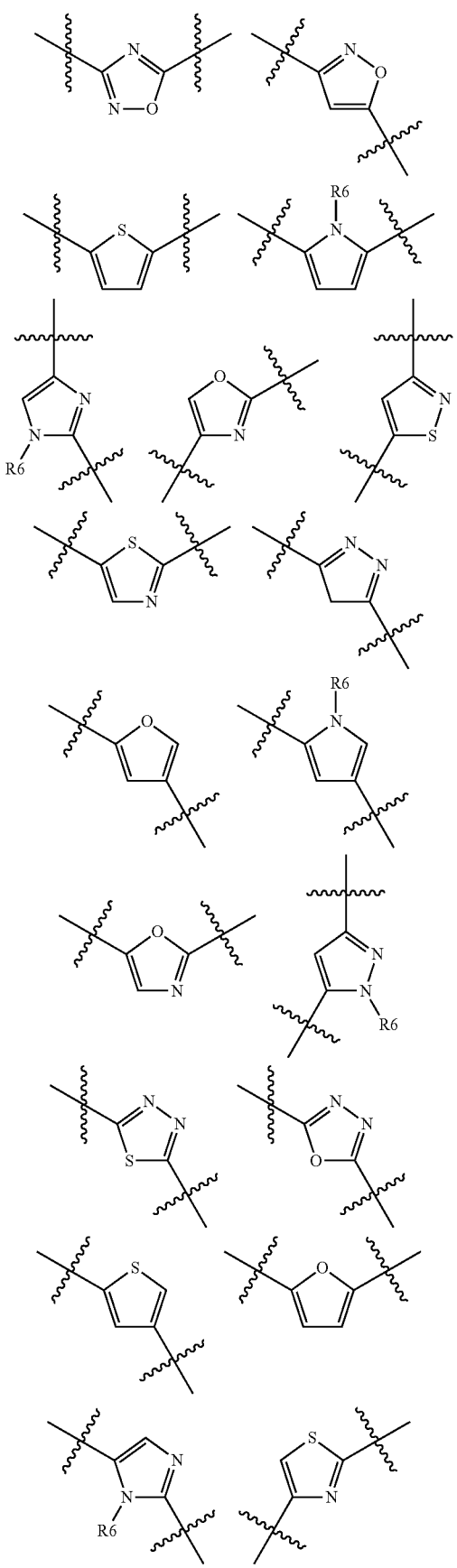

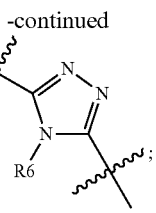

$R_6$ represents a hydrogen or alkyl radical;

as well as addition salts of the compounds of general formula (I) with a pharmaceutically-acceptable acid, addition salts of the compounds of general formula (I) with a pharmaceutically-acceptable base and enantiomers of the compounds of general formula (I).

Addition salts of general formula (I) with a pharmaceutically-acceptable acid preferably include salts with an organic acid or an inorganic acid.

Appropriate inorganic acids are, for example, hydrohalic acids (e.g., hydrochloric acid and hydrobromic acid), sulfuric acid, nitric acid and phosphoric acid.

Appropriate organic acids are, for example, acetic acid, trifluoroacetic acid, trichloroacetic acid, propionic acid, glycolic acid, pyruvic acid, succinic acid, benzoic acid, cinnamic acid, mandelic acid, methanesulfonic acid, para-toluenesulfonic acid, salicylic acid, picric acid, citric acid, oxalic acid, tartaric acid, malonic acid, maleic acid, camphorsulfonic acid and fumaric acid.

Addition salts of general formula (I) with a pharmaceutically-acceptable base preferably include salts with an organic base or an inorganic base.

Appropriate inorganic bases include hydroxides and alkali metal or alkali earth metal carbonates and bicarbonates. These bases include potassium hydroxide, sodium hydroxide, lithium hydroxide, calcium hydroxide, potassium carbonate, sodium carbonate, lithium carbonate, calcium carbonate, potassium bicarbonate, sodium bicarbonate, lithium bicarbonate or calcium bicarbonate.

Appropriate organic bases include amines and amino acids. These amines include, for example, aliphatic or aromatic primary, secondary or tertiary amines such as methylamine, ethylamine, ethanolamine, propylamine, isopropylamine, the four butylamine isomers, dimethylamine, diethylamine, diethanolamine, dipropylamine, diisopropylamine, di-n-butylamine, pyrrolidine, piperidine, morpholine, diethanol phenylamine, trimethylamine, triethylamine, tripropylamine, quinuclidine, pyridine, quinoline or isoquinoline.

Amino acids include, for example, lysine, arginine and ornithine.

According to the present invention, alkyl radical means a linear or branched saturated hydrocarbon chain with 1 to 10 carbon atoms.

According to the present invention, a fluorinated alkyl radical means an alkyl radical for which one or more hydrogen atoms are replaced by fluorine atoms.

According to the present invention, alkenyl radical means a linear or branched unsaturated hydrocarbon chain with 2 to 10 carbon atoms and comprising one or more double bonds.

According to the present invention, alkynyl radical means a linear or branched unsaturated hydrocarbon chain with 2 to 10 carbon atoms and comprising one or more triple bonds.

According to the present invention, substituted alkyl radical means a saturated, linear or branched hydrocarbon chain comprising 1 to 10 carbon atoms and substituted with one or more radicals chosen from a halogen atom, an amino radical, a dialkylamino radical, an amide radical, an alkoxyl radical, a heterocycloalkyl radical, a hydroxyl radical, a silyl radical or an alkylcarbamoyl radical.

According to the present invention, alkenyl radical means a linear or branched unsaturated hydrocarbon chain comprising 2 to 10 carbon atoms and comprising one or more double bonds and substituted with one or more radicals chosen from among a halogen atom, an amino radical, an alkoxy radical and a hydroxyl radical.

According to the present invention, substituted alkynyl radical means a linear or branched unsaturated hydrocarbon chain comprising 2 to 10 carbon atoms and comprising one or more triple bonds and substituted with one or more radicals chosen from among a halogen atom, an alkoxy radical, an amino radical and a hydroxyl radical.

According to the present invention, cycloalkyl means a saturated cyclic hydrocarbon chain comprising 3 to 7 carbon atoms.

According to the present invention, substituted cycloalkyl means a saturated cyclic hydrocarbon chain comprising 3 to 7 carbon atoms and substituted with one or more radicals chosen from among a halogen atom, an alkyl radical, an alkoxy radical, a hydroxyl radical or an amino radical.

According to the present invention, cycloalkyl-alkyl means an alkyl substituted with a cycloalkyl.

According to the present invention, aryl radical means an aromatic hydrocarbon ring or two fused aromatic hydrocarbon rings.

According to the present invention, substituted aryl radical means one or two fused aromatic hydrocarbon rings substituted with one or more groups of atoms chosen from among an alkyl, an alkoxyl, an aryl, a halogen, a hydroxyl, a cyano, a trifluoromethyl, a substituted or unsubstituted amine group and a nitro.

According to the present invention, aralkyl radical means an alkyl substituted with an aryl.

According to the present invention, substituted aralkyl radical means an alkyl substituted with a substituted aryl.

According to the present invention, heterocyclic radical means a cyclic or polycyclic hydrocarbon chain, saturated or unsaturated, comprising one or more heteroatoms chosen from among O, S and N.

According to the present invention, substituted heterocyclic radical means a heterocyclic radical substituted with one or more groups of atoms chosen from among an alkyl, an alkoxyl, a halogen, a hydroxyl, a cyano, a trifluoromethyl and a nitro.

According to the present invention, heteroaryl radical means an aromatic heterocyclic radical, i.e., a cyclic or polycyclic aromatic hydrocarbon chain comprising one or more heteroatoms chosen from among O, S and N.

According to the present invention, substituted heteroaryl radical means a heteroaryl radical substituted with one or more groups of atoms chosen, for example, from among an alkyl, an alkoxy, an aryl, a substituted aryl, a halogen, a hydroxyl, a cyano, a trifluoromethyl and a nitro.

According to the present invention, heteroaralkyl radical means an alkyl radical substituted with a heteroaryl radical.

According to the present invention, substituted heteroaralkyl radical means a heteroaralkyl radical substituted with one or more groups of atoms chosen from among an alkyl, an alkoxyl, a halogen, a hydroxyl, a cyano, a trifluoromethyl and a nitro.

According to the present invention, alkoxyl radical means an oxygen atom substituted with an alkyl radical.

According to the present invention, halogen atom means a fluorine, chlorine, bromine or iodine atom.

The compounds of general formula (I) within the scope of the present invention notably include the following compounds:

4-[3-(3-adamantan-1-yl-4-ethoxymethoxy-phenyl)-[1,2,4]oxadiazol-5-yl]-benzoic acid
4-[5-(5,5,8,8-tetramethyl-5,6,7,8-tetrahydro-naphthalen-2-yl)-thiazol-2-yl]-benzoic acid
4-[5-(3-adamantan-1-yl-4-ethoxymethoxy-phenyl)-thiazol-2-yl]-benzoic acid
4-{5-[3-adamantan-1-yl-4-(2-methoxy-ethoxymethoxy)-phenyl]-1,3,4-oxadiazol-2-yl}-benzoic acid
4-[5-(3-adamantan-1-yl-4-hydroxy-phenyl)-thiazol-2-yl]benzoic acid
4-[3-(3-adamantan-1-yl-4-hydroxy-phenyl)-[1,2,4]oxadiazol-5-yl]-benzoic acid
4-{5-[3-adamantan-1-yl-4-(2-methoxy-ethoxy)-phenyl]-thiazol-2-yl}-benzoic acid
4-[5-(3-tert-butyl-4-hydroxy-phenyl)-thiazol-2-yl]benzoic acid
4-[5-(3-adamantan-1-yl-4-methoxy-phenyl)-thiazol-2-yl]benzoic acid
4-[5-(3-adamantan-1-yl-4-isobutoxy-phenyl)-thiazol-2-yl]-benzoic acid
4-[5-(3-adamantan-1-yl-4-propoxy-phenyl)-thiazol-2-yl]benzoic acid
4-[5-(3-adamantan-1-yl-4-ethoxy-phenyl)-thiazol-2-yl]benzoic acid
4-[5-(3-adamantan-1-yl-4-hydroxy-phenyl)-[1,3,4]oxadiazol-2-yl]-benzoic acid
4-[5-(3-adamantan-1-yl-4-isobutoxy-phenyl)-[1,3,4]oxadiazol-2-yl]-benzoic acid
4-{3-[3-adamantan-1-yl-4-(2-methoxy-ethoxy)-phenyl]-[1,2,4]oxadiazol-5-yl}-benzoic acid
4-{3-[3-adamantan-1-yl-4-(2-dimethylamino-ethoxy)-phenyl]-[1,2,4]oxadiazol-5-yl}-benzoic acid
4-[3-(3-adamantan-1-yl-4-methoxy-phenyl)-[1,2,4]oxadiazol-5-yl]-benzoic acid
4-[3-(3-adamantan-1-yl-4-ethoxy-phenyl)-[1,2,4]oxadiazol-5-yl]-benzoic acid
4-[3-(3-adamantan-1-yl-4-propoxy-phenyl)-[1,2,4]oxadiazol-5-yl]-benzoic acid
4-[3-(3-adamantan-1-yl-4-isobutoxy-phenyl)-[1,2,4]oxadiazol-5-yl]-benzoic acid
4-{3-[3-adamantan-1-yl-4-(2,2-dimethoxy-ethoxy)-phenyl]-[1,2,4]oxadiazol-5-yl}-benzoic acid
4-[3-(3-tert-butyl-4-ethoxymethoxy-phenyl)-[1,2,4]oxadiazol-5-yl]-benzoic acid
4-{5-[4-(2-methoxy-ethoxymethoxy)-3-(1-methyl-cyclohexyl)-phenyl]-thiazol-2-yl}-benzoic acid
4-[5-(3-adamantan-1-yl-4-methoxy-phenyl)-[1,3,4]oxadiazol-2-yl]-benzoic acid
4-[5-(3-adamantan-1-yl-4-ethoxy-phenyl)-[1,3,4]oxadiazol-2-yl]-benzoic acid
4-5-(3-adamantan-1-yl-4-cyclopropylmethoxy-phenyl)-[1,3,4]oxadiazol-2-yl]-benzoic acid
4-{5-[3-adamantan-1-yl-4-(2,2,2-trifluoro-ethoxy)-phenyl]-[1,3,4]-oxadiazol-2-yl}-benzoic acid
4-[5-(3-adamantan-1-yl-4-propoxy-phenyl)-[1,3,4]oxadiazol-2-yl]-benzoic acid
4-[3-(3-tert-butyl-4-hydroxy-phenyl)-[1,2,4]oxadiazol-5-yl]-benzoic acid
4-{3-[4-ethoxymethoxy-3-(1-methyl-cyclohexyl)-phenyl]-[1,2,4]-oxadiazol-5-yl}-benzoic acid
4-{3-[4-hydroxy-3-(1-methyl-cyclohexyl)-phenyl]-[1,2,4]-oxadiazol-5-yl}-benzoic acid
4-{3-[3-tert-butyl-4-(2-methoxy-ethoxy)-phenyl]-[1,2,4]-oxadiazol-5-yl}-benzoic acid 4-{3-[3-tert-butyl-4-(2-dimethylamino-ethoxy)-phenyl]-[1,2,4]-oxadiazol-5-yl}-benzoic acid
4-[3-(3-tert-butyl-4-methoxy-phenyl)-[1,2,4]oxadiazol-5-yl]-benzoic acid
4-[3-(3-tert-butyl-4-ethoxy-phenyl)-[1,2,4]oxadiazol-5-yl]-benzoic acid
4-[3-(3-tert-butyl-4-propoxy-phenyl)-[1,2,4]oxadiazol-5-yl]-benzoic acid
4-[3-(3-tert-butyl-4-isobutoxy-phenyl)-[1,2,4]oxadiazol-5-yl]-benzoic acid
4-{3-[3-tert-butyl-4-(2,2,2-trifluoro-ethoxy)-phenyl]-[1,2,4]-oxadiazol-5-yl}-benzoic acid
4-[3-(3-tert-butyl-4-cyclopropylmethoxy-phenyl)-[1,2,4]oxadiazol-5-yl]-benzoic acid
4-{3-[3-tert-Butyl-4-(2,2-dimethoxy-ethoxy)-phenyl]-[1,2,4]-oxadiazol-5-yl}-benzoic acid
4-[3-(3-tert-butyl-4-[1,3]dioxolan-2-ylmethoxy)-phenyl]-[1,2,4]oxadiazol-5-yl)-benzoic acid
4-{5-[4-hydroxy-3-(1-methyl-cyclohexyl)-phenyl]-thiazol-2-yl}-benzoic acid
4-{5-[4-hydroxy-3-(1-methyl-cyclohexyl)-phenyl]-thiazol-2-yl}-benzoic acid
4-{5-[4-hydroxy-3-(1-methyl-cyclohexyl)-phenyl]-thiazol-2-yl}-benzoic acid
4-{5-[4-isobutoxy-3-(1-methyl-cyclohexyl)-phenyl]-thiazol-2-yl}-benzoic acid
4-{5-[4-methoxy-3-(1-methyl-cyclohexyl)-phenyl]-thiazol-2-yl}-benzoic acid
4-{5-[3-(1-methyl-cyclohexyl)-4-propoxy-phenyl]-thiazol-2-yl}-benzoic acid
4-{5-[4-cyclopropylmethoxy-3-(1-methyl-cyclohexyl)-phenyl]-thiazol-2-yl}-benzoic acid
4-{5-[4-ethylcarbamoylmethoxy-3-(1-methyl-cyclohexyl)-phenyl]-thiazol-2-yl}-benzoic acid
4-[3-(3-adamantan-1-yl-4-trimethylsilanylmethoxy-phenyl)-[1,2,4]oxadiazol-5-yl]-benzoic acid
4-{5-[3-adamantan-1-yl-4-(2,2-dimethoxy-ethoxy)-phenyl]-[1,3,4]-oxadiazol-2-yl}-benzoic acid
4-{5-[3-adamantan-1-yl-4-(2-methoxy-ethoxymethoxy)-phenyl]-4H-pyrazol-3-yl}-benzoic acid
4-[5-(3-adamantan-1-yl-4-propylamino-phenyl)-thiazol-2-yl]-benzoic acid
4-[5-(3-tert-butyl-4-methoxy-phenyl)-thiazol-2-yl]-benzoic acid
4-[5-(3-tert-butyl-4-ethoxy-phenyl)-thiazol-2-yl]-benzoic acid
4-[5-(3-tert-butyl-4-propoxy-phenyl)-thiazol-2-yl]-benzoic acid
4-{5-[3-tert-butyl-4-(2,2,2-trifluoro-ethoxy)-phenyl]-thiazol-2-yl}-benzoic acid
4-[5-(3-tert-butyl-4-cyclopropylmethoxy-phenyl)-thiazol-2-yl]-benzoic acid
4-{5-[3-tert-butyl-4-(2-methoxy-ethoxy)-phenyl]-thiazol-2-yl}-benzoic acid
4-{5-[3-tert-butyl-4-(2,2-dimethoxy-ethoxy)-phenyl]-thiazol-2-yl}-benzoic acid
4-{5-[3-(1-methyl-cyclohexyl)-4-(2,2,2-trifluoro-ethoxy)-phenyl]-thiazol-2-yl}-benzoic acid
4-{3-[4-methoxy-3-(1-methyl-cyclohexyl)-phenyl]-1,2,4-oxadiazol-5-yl}-benzoic acid
4-{3-[3-(1-methyl-cyclohexyl)-4-propoxy-phenyl]-[1,2,4]oxadiazol-5-yl}-benzoic acid
4-{3-[4-isobutoxy-3-(1-methyl-cyclohexyl)-phenyl]-[1,2,4]-oxadiazol-5-yl}-benzoic acid
4-{3-[4-cyclopropylmethoxy-3-(1-methyl-cyclohexyl)-phenyl]-[1,2,4]-oxadiazol-5-yl}-benzoic acid
4-{3-[4-(2,2-dimethoxy-ethoxy)-3-(1-methyl-cyclohexyl)-phenyl]-[1,2,4]oxadiazol-5-yl}-benzoic acid
4-[3-(3-adamantan-1-yl-4-hydroxy-phenyl)-isoxazol-5-yl]benzoic acid
4-[5-(3-adamantan-1-yl-4-hydroxy-phenyl)-4H-pyrazol-3-yl]-benzoic acid
4-[3-(3-adamantan-1-yl-4-cyclopropylmethoxy-phenyl)-isoxazol-5-yl]-benzoic acid
4-[3-(3-adamantan-1-yl-4-methoxy-phenyl)-isoxazol-5-yl]benzoic acid
4-[3-(3-adamantan-1-yl-4-propoxy-phenyl)-isoxazol-5-yl]benzoic acid
4-[3-(3-adamantan-1-yl-4-isobutoxy-phenyl)-isoxazol-5-yl]-benzoic acid
4-{3-[3-adamantan-1-yl-4-(2,2-dimethoxy-ethoxy)-phenyl]-isoxazol-5-yl}-benzoic acid
4-[5-(3-tert-butyl-4-ethylcarbamoylmethoxy-phenyl)-thiazol-2-yl]-benzoic acid
4-[5-(3-tert-butyl-4-isobutoxy-phenyl)-thiazol-2-yl]-benzoic acid
4-[3-(3-adamantan-1-yl-4-ethoxy-phenyl)-isoxazol-5-yl]benzoic acid
4-{5-[3-adamantan-1-yl-4-([1,3]dioxolan-2-ylmethoxy)-phenyl]-[1,3,4]oxadiazol-2-yl}-benzoic acid
4-{3-[3-(1-methylcyclohexyl)-4-(2,2,2-trifluoroethoxy)-phenyl]-[1,2,4]oxadiazol-5-yl}-benzoic acid
4-{3-[4-([1,3]dioxolan-2-ylmethoxy)-3-(1-methylcyclohexyl)-phenyl]-[1,2,4]oxadiazol-5-yl}-benzoic acid
4-[5-(3-adamantan-1-yl-4-propylamino-phenyl)-thiazol-2-yl]-benzoic acid
4-{3-[3-tert-butyl-4-(2-hydroxy-ethoxy)-phenyl]-[1,2,4]-oxadiazol-5-yl}-benzoic acid
4-{3-[3-tert-butyl-4-(3-hydroxy-propoxy)-phenyl]-[1,2,4]-oxadiazol-5-yl}-benzoic acid
4-[5-(3-tert-butyl-4-propoxy-phenyl)-1-methyl-1H-imidazol-2-yl]-benzoic acid
4-[5-(4-allyloxy-3-tert-butyl-phenyl)-[1,3,4]thiadiazol-2-yl]-benzoic acid
4-{4-[3-(1-methyl-cyclohexyl)-4-(pyridin-4-ylmethoxy)-phenyl]-oxazol-2-yl}-benzoic acid
4-[5-(4-ethoxy-3-pyrrolidin-1-yl-phenyl)-4H-[1,2,4]triazol-3-yl]-benzoic acid
4-{5-[3-diethylamino-4-(4-fluoro-benzyloxy)-phenyl]-[1,3,4]-thiadiazol-2-yl}-benzoic acid
4-[5-(3-tert-butyl-4-isobutoxy-phenyl)-[1,3,4]thiadiazol-2-yl]-benzoic acid
methyl 4-[3-(3-tert-butyl-4-hydroxy-phenyl)-[1,2,4]oxadiazol-5-yl]-benzoate
4-[5-(4-butoxy-3-tert-butyl-phenyl)-1-methyl-1H-pyrrol-2-yl]-benzoic acid
4-{5-[4-(2-amino-ethoxy)-3-tert-butyl-phenyl]-thiophen-2-yl}-benzoic acid
4-{3-[3-tert-butyl-4-((E)-propenyl)-phenyl]-[1,2,4]oxadiazol-5-yl}-benzoic acid
4-[3-(3-tert-butyl-4-propyl-phenyl)-[1,2,4]oxadiazol-5-yl]-benzoic acid
4-[5-(3-tert-butyl-4-ethylsulfanyl-phenyl)-thiazol-2-yl]-benzoic acid
4-[5-(3-tert-butyl-4-cyclopropylmethylsulfanyl-phenyl)-oxazol-2-yl]-benzoic acid
4-[3-(4-cyclopropylmethoxy-3-pyrrolidin-1-yl-phenyl)-[1,2,4]oxadiazol-5-yl]-benzoic acid
4-[3-(4-hydroxy-3-pyrrolidin-1-yl-phenyl)-[1,2,4]oxadiazol-5-yl]-benzoic acid
4-{3-[4-(2-hydroxy-ethoxy)-3-pyrrolidin-1-yl-phenyl]-[1,2,4]oxadiazol-5-yl}-benzoic acid 3-[5-(3-adamantan-1-yl-4-hydroxy-phenyl)-2-ethyl-2H-pyrazol-3-yl]-benzoic acid
4-{3-[4-diethylamino-3-(3-hydroxy-propoxy)-phenyl]-[1,2,4]-oxadiazol-5-yl}-benzoic acid
4-[3-(4-diethylamino-3-propoxy-phenyl)-isoxazol-5-yl]-benzoic acid
4-[3-(4-tert-butyl-3-ethylamino-phenyl)-[1,2,4]oxadiazol-5-yl]-benzoic acid
4-(2-[3-(1-methyl-cyclohexyl)-4-(pyridin-4-ylmethoxy)-phenyl]-oxazol-4-yl}-benzoic acid
4-[2-(3-tert-butyl-4-cyclopropylmethylsulfanyl-phenyl)-oxazol-5-yl]-benzoic acid
4-[5-(3-tert-butyl-4-hydroxy-phenyl)-[1,3,4]oxadiazol-2-yl]-benzoic acid
4-[5-(3-tert-butyl-4-ethoxy-phenyl)-[1,3,4]oxadiazol-2-yl]-benzoic acid
4-[5-(4-hydroxy-3-pyrrolidin-1-yl-phenyl)-[1,3,4]oxadiazol-2-yl]-benzoic acid
methyl 4-[5-(4-hydroxy-3-pyrrolidin-1-yl-phenyl)-[1,3,4]oxadiazol-2-yl]-benzoate
methyl 4-[3-(4-tert-butyl-3-ethylamino-phenyl)-[1,2,4]oxadiazol-5-yl]-benzoate.

Compounds of general formula (I) are prepared according to the reaction schemes of Figures 1 to 8 presented below. The choice of the synthesis scheme used is linked to the central heterocycle of the compound whose synthesis is sought.

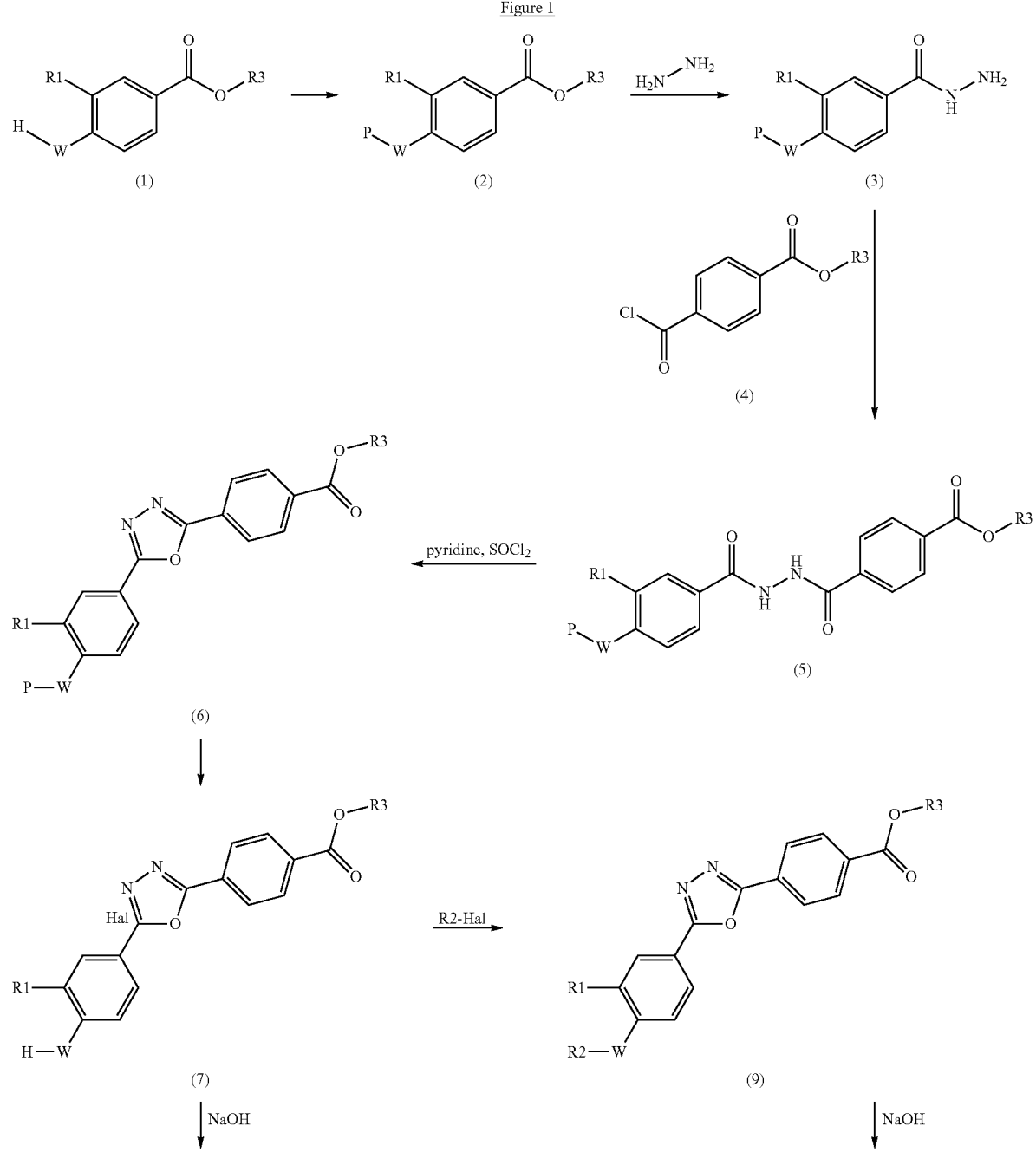

Figure 1

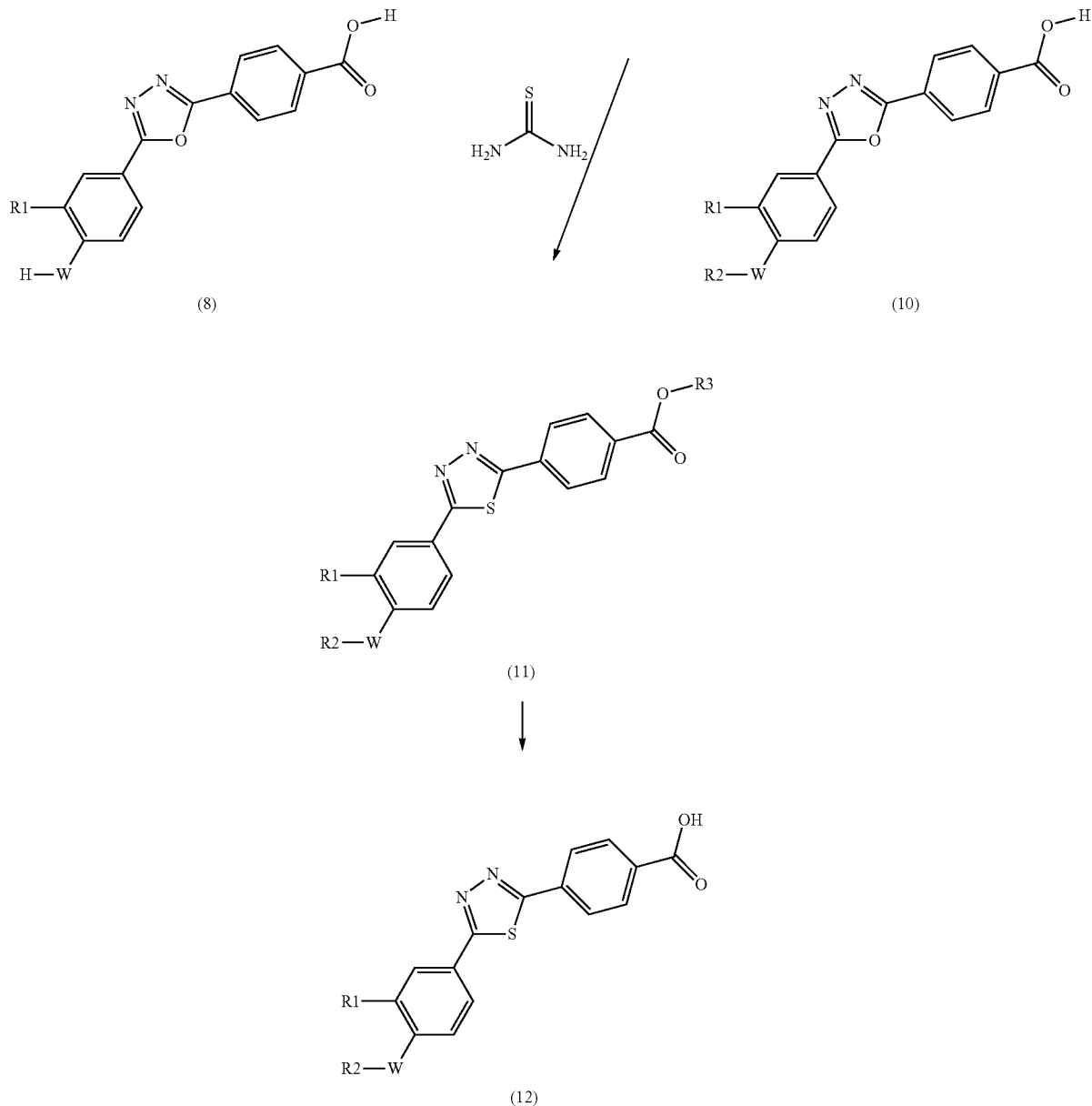

According to Figure 1, 1,2,4-oxadiazole or 1,2,4-thiadiazole derivatives can be obtained. Thus, the hydrazide derivative (3) can be obtained by reaction of ester (2) with hydrazine after a protection step in the case where W=O or S. The choice of protective group P depends on the reaction sequence that follows. Many conventionally used protective groups as described in the book "Protective Groups in Organic Synthesis" (Third edition, authors: Theodora W. Greene & Peter G. M. Wuts, Editor: Wiley InterScience) can be considered. A polyether group (ethyl methyl ether, for example) can be considered. Compound (5) below is thus obtained by reaction of hydrazide derivative (3) with acyl chloride (4) (commercially available in the case of R3 being a methyl). In the presence of thionyl chloride and pyridine, this compound is cyclized to lead to the oxadiazole derivative (6). In the case of compounds with W=O, S or N, after a step of deprotecting the P group according to the conventional conditions described in the book "Protective Groups in Organic Chemistry", compound (7) obtained can be saponified to lead to derivative (8) or alkylated in the presence of an alkyl halide, for example, and a base such as potassium carbonate or by reductive amination reaction when W=N, to lead to compound (9). After saponification of compound (9) according to conventional conditions (aqueous sodium hydroxide for example), derivative (10) is obtained. It is also possible to obtain the corresponding thiadiazole derivative (11) by treatment of compound (9) in the presence of thiourea and pyridine, for example. By saponification of compound (11), derivative (12) can be obtained.

Figure 2

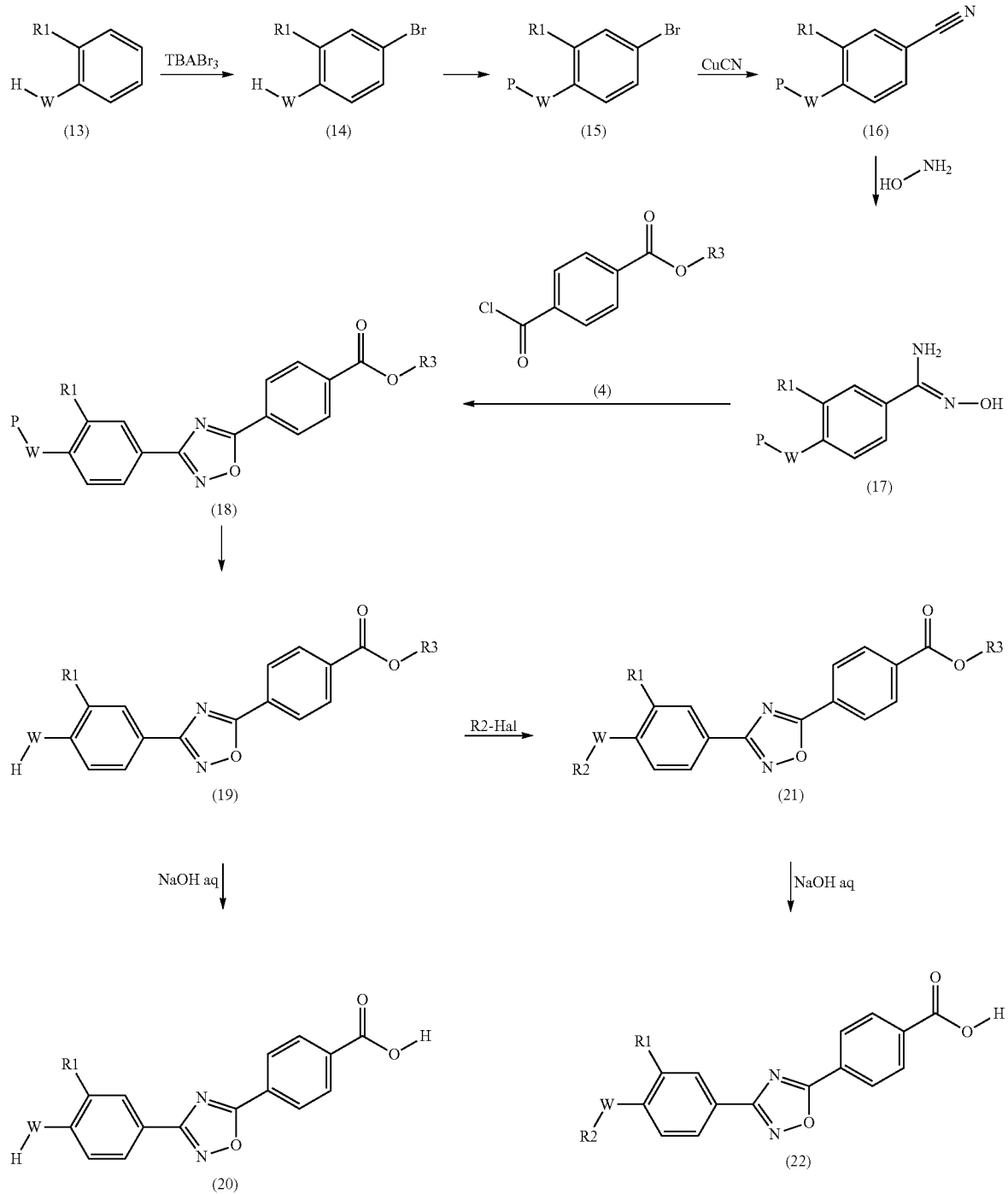

According to Figure 2, other oxadiazole derivatives (1,3,4-oxadiazoles) can be prepared. After bromination of compounds (13), commercially available or previously prepared, for example by tetrabutylammonium bromide, compounds (14) obtained are protected by a protective group like ethyl methyl ether, for example, in the case of W=O or S. Compounds (15) are obtained by substitution reaction with copper (I) cyanide. In the presence of hydroxylamine, these compounds react to form derivatives (17). The reaction between compound (17) and acid chloride (4) commercially available permits obtaining oxadiazole (18). After deprotecting this compound when W=O, S, N and obtaining compound (19), this can be saponified to lead to compound (20). By alkylation of compound (19) in the presence of an alkyl halide, for example, and a base such as potassium carbonate or by reductive amination reaction when W=N, compound (21) can also be obtained. The saponification of this compound leads to acid compound (22).

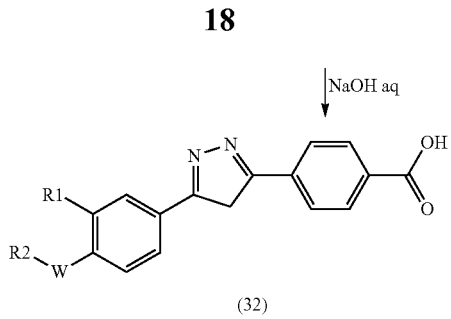

(32)

Pyrazole-type heterocyclic derivatives can be obtained according to Figure 3. After protection of compounds for which W=O or S and saponification of their ester function, compounds (23) are obtained. By reaction of methyllithium, for example, on acid derivatives (23), the corresponding methyl ketone (24) is obtained. This methyl ketone can react with acid chloride (4) in order to form the 1,3-diphenyl-propane-1,3-dione derivative (25), which, in turn, after condensation with hydrazine, forms diazole derivative (26). A deprotection step of this compound leads to compound (27) which, after saponification, permits obtaining compound (28). Protection of the diazole nucleus may also be considered to obtain derivative (29). Thus, after selective deprotection of the phenol, thiophenol or amine function of this compound when W=O, S, N followed by alkylation in the presence of an alkyl halide, for example, and a base such as potassium carbonate or followed by a reductive amination reaction, compound (31) may be prepared. By reaction of compound (31) with aqueous sodium hydroxide, for example, compound (32) can be prepared.

Figure 4

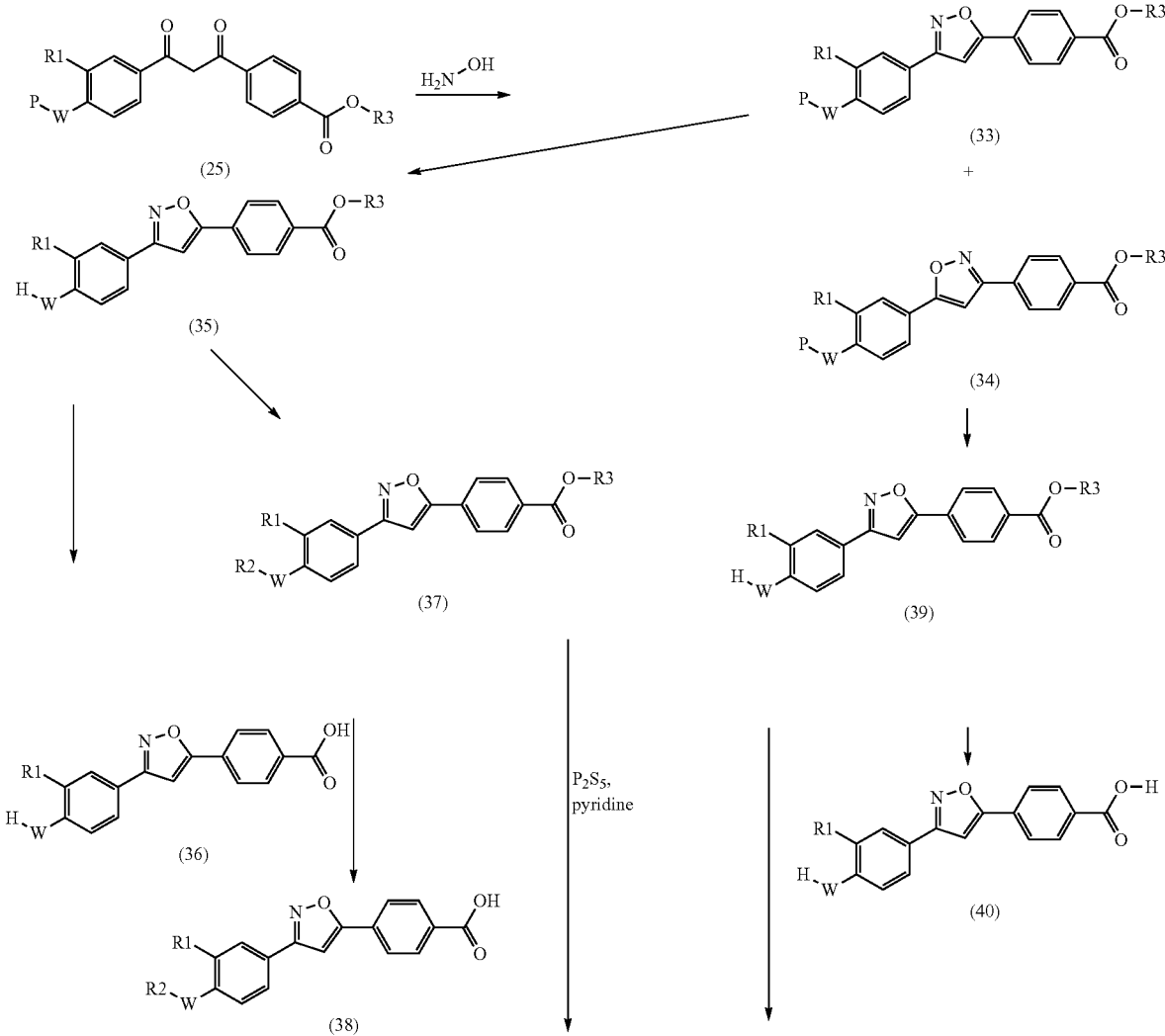

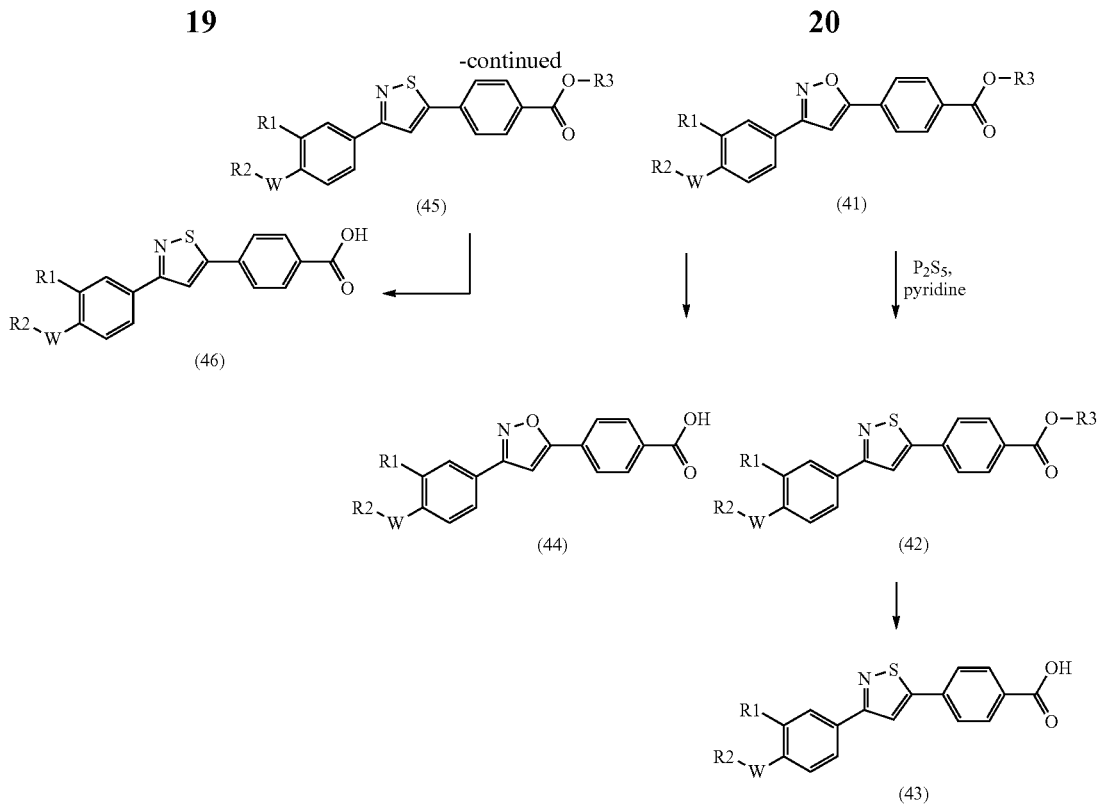

Figure 4 describes a method for preparing isoxazole compounds. Thus, by condensation of hydroxylamine in the 1,3-diphenyl-propane-1,3-dione derivative (25), prepared as described above, two oxazole derivatives (33) and (34) can be obtained depending on the direction of the condensation and the operating conditions followed. Once these compounds are obtained and separated, they may respectively lead to derivatives (35) and (39), after deprotection of their amino, phenol or thiophenol function. By saponification of compounds (35) and (39) in the presence of aqueous sodium hydroxide, for example, compounds (36) and (40) can be prepared. An alkylation of compounds (35) and (39) in the presence of an alkyl halide, for example, and a base such as potassium carbonate, followed by a saponification step permits obtaining, respectively, compounds (38) and (44). By reaction of compounds (37) and (41) (obtained by alkylation of their phenol or thiophenol functions or by reductive amination of aniline) with diphosphorus pentasulfide in the presence of pyridine, the corresponding thiazoles derivatives (45) and (42) can be prepared

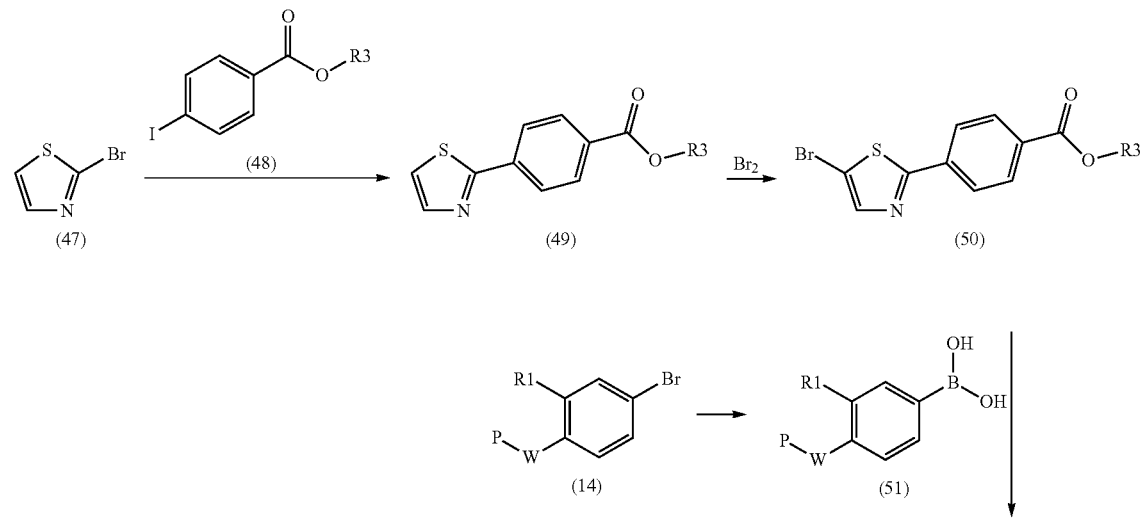

Figure 5

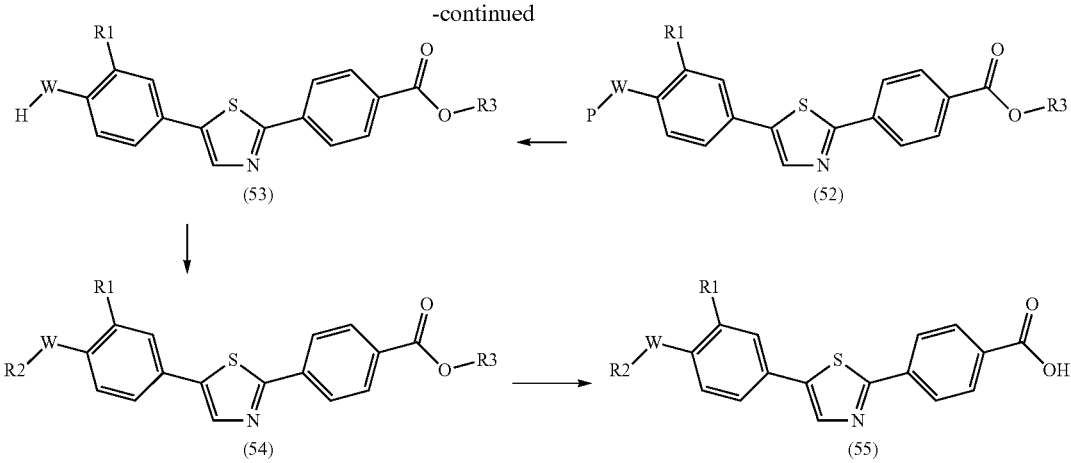

Thiazole derivatives can be obtained according to the synthesis scheme described in Figure 5. By Negishi coupling reaction between 2-bromothiazole (47) and the organozinc derivative previously prepared from iodinated derivative (48), compound (49) is obtained. A bromination of this compound with bromine, for example, leads to compound (50). By Suzuki coupling, in the presence of a tetra (triphenylphosphine)palladium catalyst and a base such as aqueous potassium carbonate, for example, between brominated derivative (50) and boronic acid (51) previously prepared from the corresponding brominated compound (14), compound (52) is obtained After deprotection of any amino, phenol or thiophenol function then alkylation in the presence of an alkyl halide, for example, and a base such as potassium carbonate or by reductive amination of the aniline function, compound (54) is obtained. A saponification of this compound in the presence of aqueous sodium hydroxide, for example, leads to compound (55).

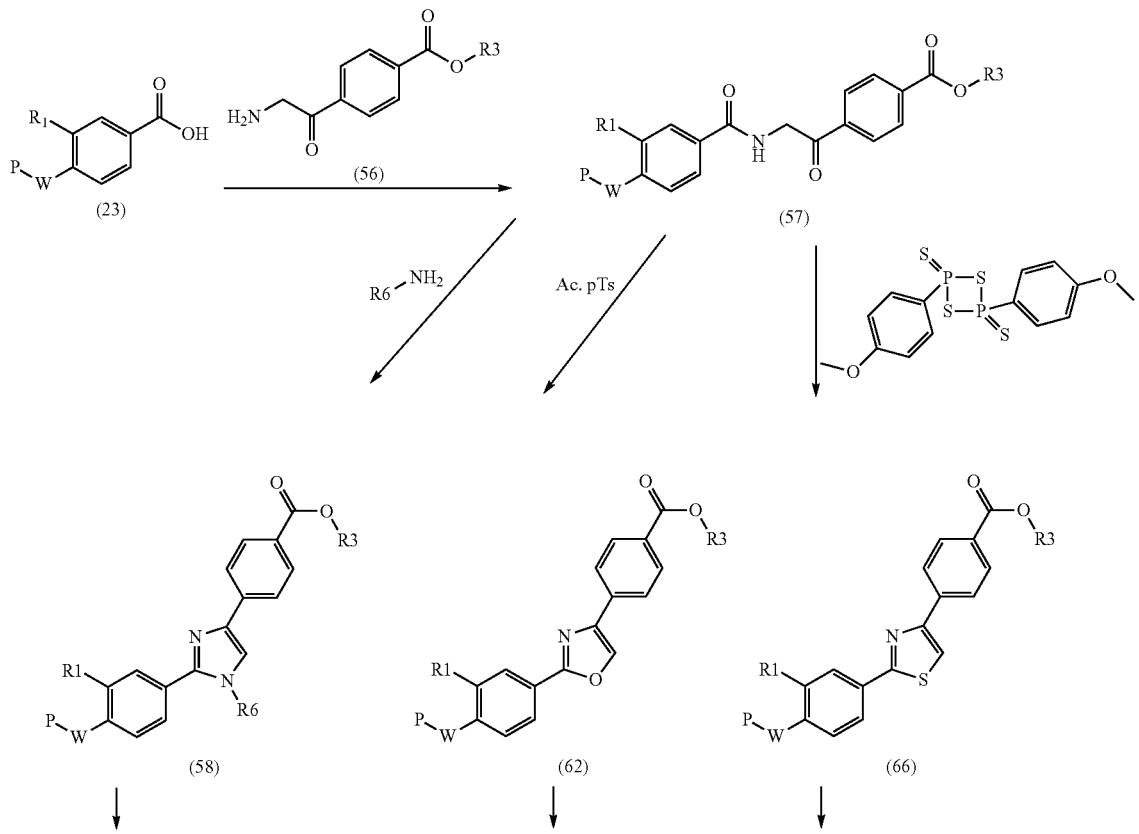

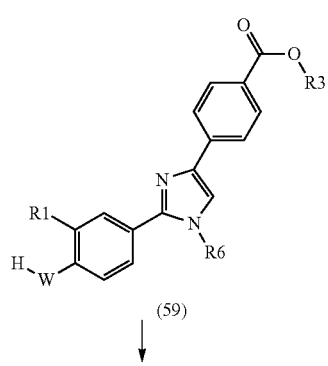

(59)

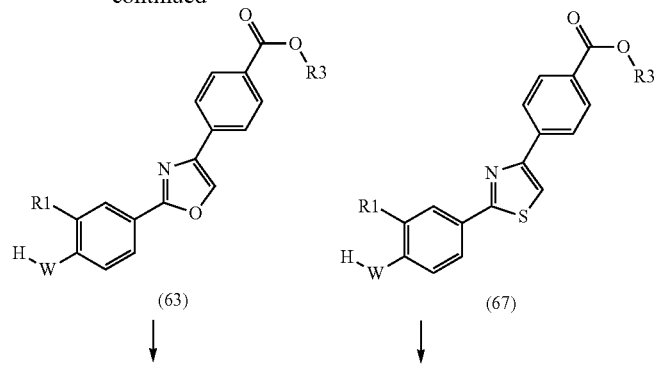

(63)    (67)

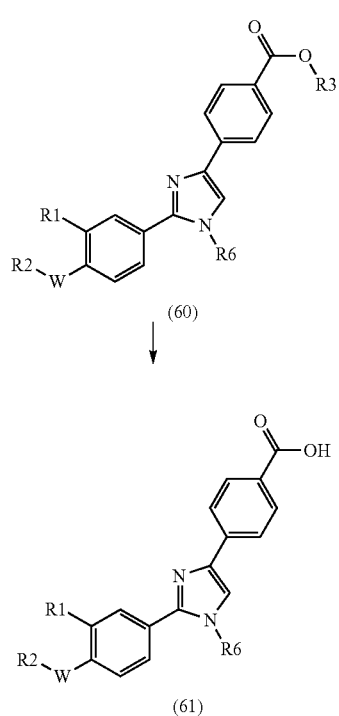

(60)

(61)

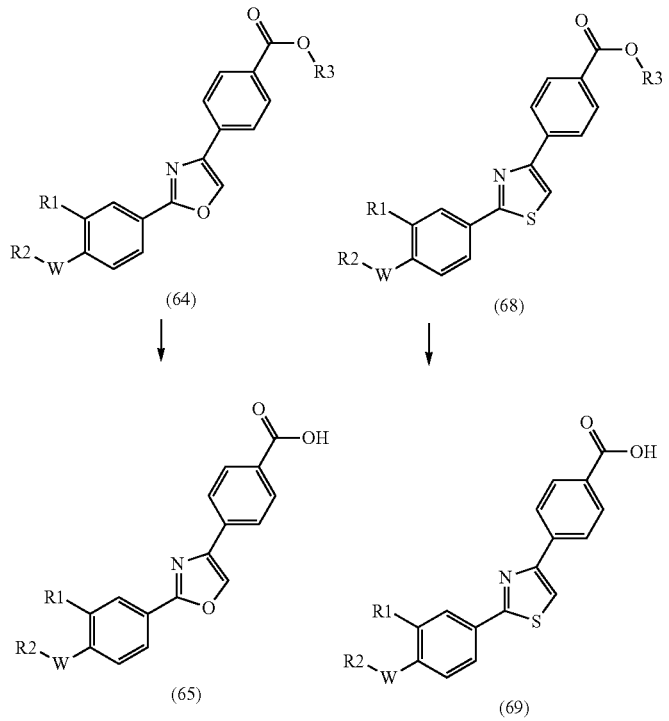

(64)    (68)

(65)    (69)

The scheme of Figure 6 describes imidazole, oxazole and thiazole derivatives. Thus, by peptide coupling reaction in the presence of 1-hydroxybenzotriazole and 1-(3-dimethyl-aminopropyl)-3-ethylcarbodiimide hydrochloride, for example, between acid (23) previously protected and commercially-available methyl ester (56), compound (57) is obtained. Cyclization of this compound in the presence of para-toluenesulfonic acid, for example, leads to corresponding oxazole derivative (62), cyclization in the presence of ammonia or a primary amine leads to optionally N-alkylated imidazole (58), and finally, cyclization in the presence of 2,4-bis(4-methoxyphenyl)-1,3-dithia-2,4-diphosphetane 2,4-disulfide (Lawesson's reagent) makes it possible to obtain corresponding thiazole (66). After deprotection of any amino, phenol or thiophenol function (compound (59), (63) and (67)), then optional alkylation in the presence of an alkyl halide, for example, and a base such as potassium carbonate or by reductive amination on the aniline function, compounds (60), (64) and (68) are obtained. A saponification of these compounds in the presence of aqueous sodium hydroxide, for example, leads to compounds (61), (65) and (69).

Figure 7

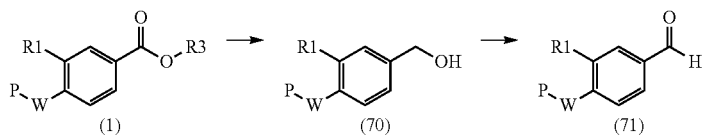

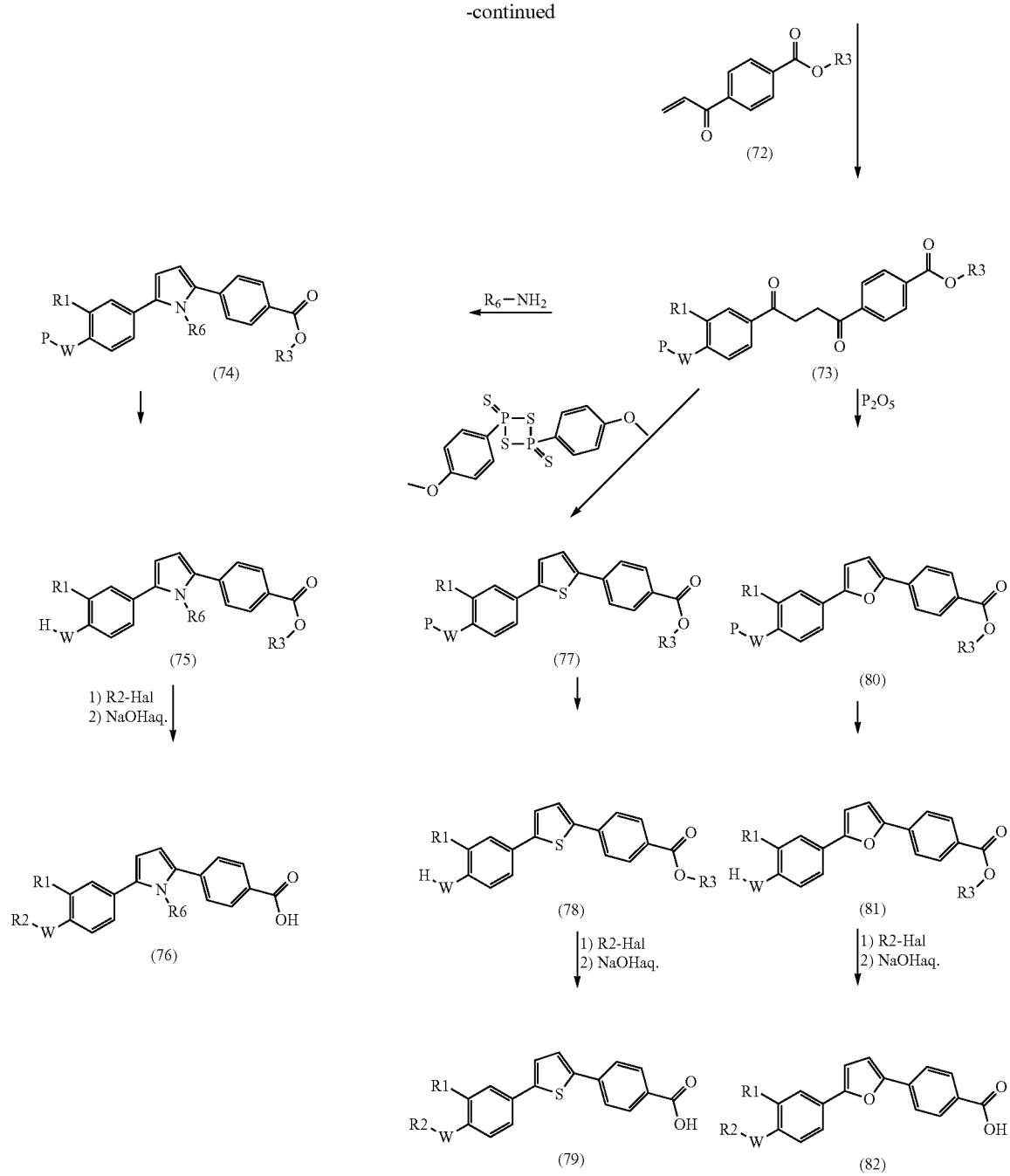

According to the schemes described in Figure 7, access to pyrroles, furans and thiophenes is possible. By reduction of ester function derivatives (1) (optionally previously protected at the phenol or thiophenol function) in the presence of aluminum lithium hydride, for example, benzylic alcoholic derivative (70) is obtained. This compound is oxidized in the presence of manganese dioxide, for example, to give compound (71). Stetter reaction between this aldehyde (71) and methyl benzoate 4-acrylate, for example, previously prepared (72) according to the standard conditions described in the publication Angew. Chem. Int. Ed. 1976, 15 (11), p. 639-647, derivative (73) is obtained. Reaction of this compound in the presence of ammonia or a primary amine leads to corresponding pyrrole (74). By reaction of compound (73) with 2,4-bis(4-methoxyphenyl)-1,3-dithia-2,4-diphosphetane 2,4-disulfide (Lawesson's reagent) the corresponding thiophene derivative (77) is obtained. By reaction of compound (73) with phosphorus pentoxide, furan derivative (80) can be prepared. After deprotection of any amino, phenol or thiophenol function (compounds (75), (78) and (81)), then optional alkylation in the presence of an alkyl halide, for example, and a base such as potassium carbonate or by reductive amination on the aniline function and finally, saponification in the presence of aqueous sodium hydroxide, for example, compounds (76), (79) and (82) are obtained.

Figure 8

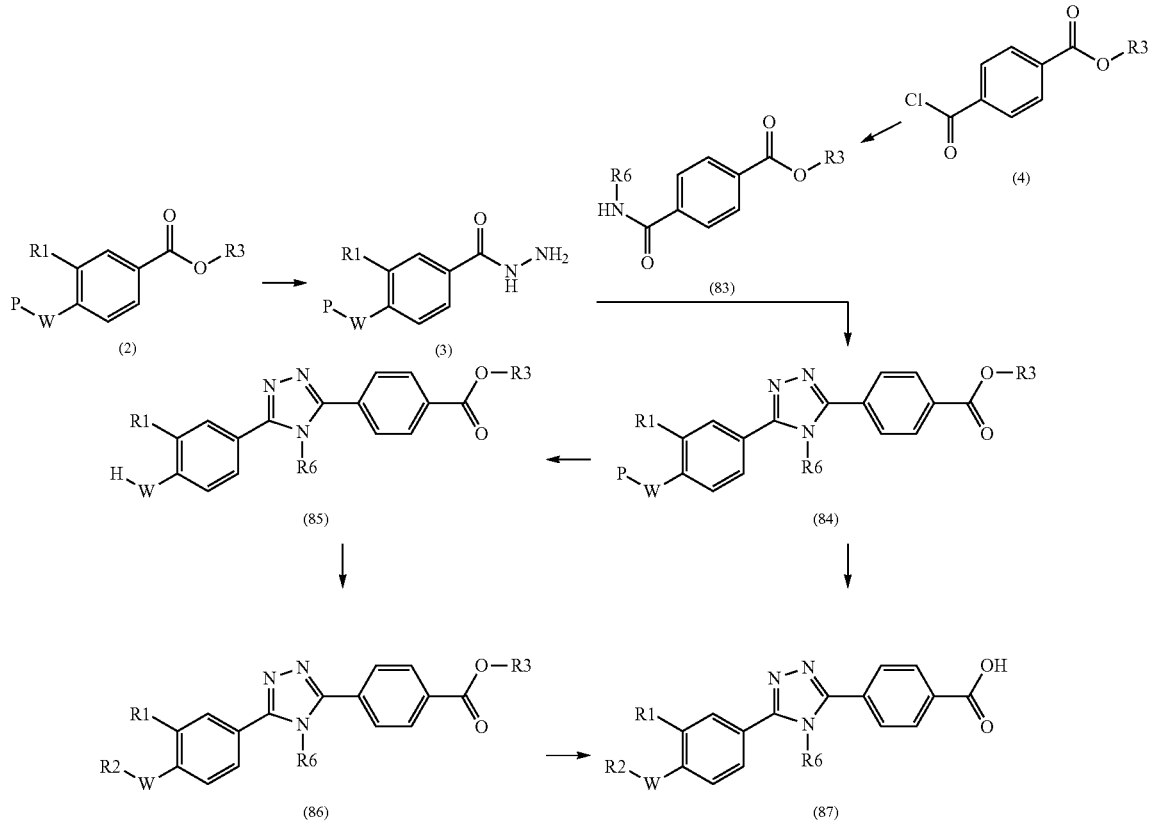

Figure 8 describes a method for obtaining triazole derivatives. By reaction of ester derivative (2) with hydrazine, compound (3) is obtained. A reaction between this hydrazide (3) and amide derivative (83) (previously prepared by reaction of commercially-available acid chloride (4) when R3 is a methyl, with an R6NH$_2$ amine, leads to triazole derivative (84). In the case where W=O, S or N, a deprotection step releases the phenol or thiophenol functions and leads to compound (85). An alkylation of this compound in the presence of an alkyl halide, for example, and a base such as potassium carbonate or a reductive amination on the aniline function followed by a saponification step permits obtaining compound (87).

According to the present invention, the particularly preferred compounds of general formula (I) are those for which:

A represents a group chosen from among:

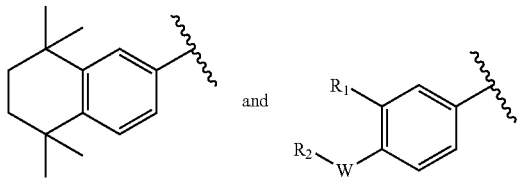

R1 is a linear or branched alkyl radical, a substituted cycloalkyl radical, an adamantyl radical or an NR4R5 radical;

R2 is a hydrogen atom, a linear or branched alkyl radical, a polyether radical or a mono or polyhydroxyalkyl radical, R3 is a hydrogen atom, R4 and R5, identical or different, represent a linear or branched alkyl radical, a substituted alkyl radical or an acyl radical. R4 and R5, taken together, can also be bound and form an azetidine, pyrrolidine or piperidine heterocycle with the nitrogen atom that can also be substituted.

X is O, S or CH$_2$,

The central heterocycle is preferably

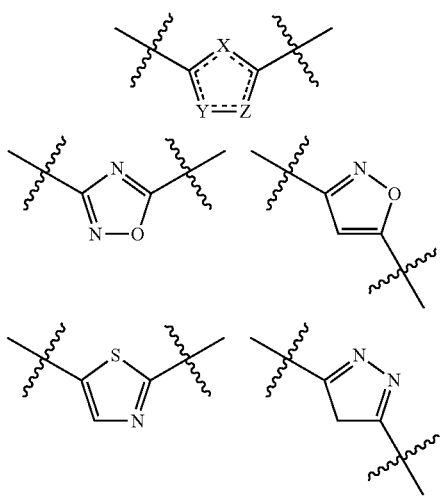

-continued

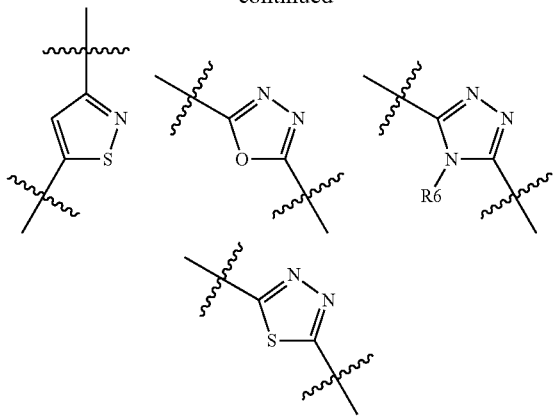

According to the present invention, the particularly preferred compounds of general formula (I) are those for which:

A represents a group chosen from among:

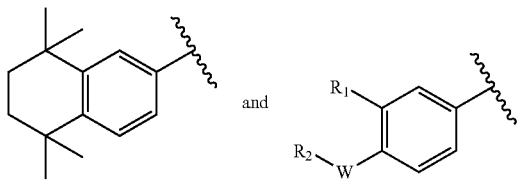

and

R1 is a branched alkyl radical, a substituted cycloalkyl radical or a NR4R5 radical R2 is a hydrogen atom, a linear or branched alkyl radical, a polyether radical or a mono or polyhydroxyalkyl radical, R3 is a hydrogen atom, R4 and R5, identical or different, represent a linear or branched alkyl radical, a substituted alkyl radical or an acyl radical. R4 and R5, taken together, can also be bound and form an azetidine, pyrrolidine or piperidine heterocycle with the nitrogen atom that can also be substituted.

X is O, S

The central heterocycle is preferably

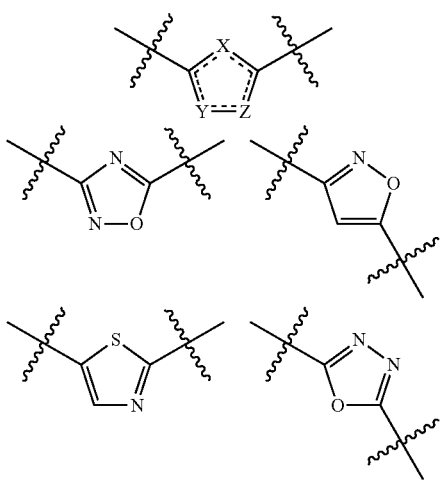

According to the present invention, the particularly preferred compounds of general formula (I) are those for which:

A represents a

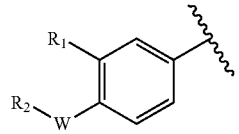

group

R1 is a branched alkyl radical or an NR4R5 radical,

R2 is a hydrogen atom, a linear or branched alkyl radical or a monohydroxyalkyl radical.

R3 is a hydrogen atom,

R4 and R5, identical or different, represent a linear or branched alkyl radical, R4 and R5 taken together can also be bound and form a pyrrolidine heterocycle type with the nitrogen atom, which heterocycle can also be substituted.

X is O, the central heterocycle is preferably an oxadiazole

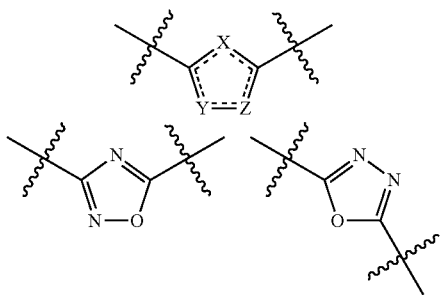

According to another preferred embodiment, the invention concerns a compound of formula (I) in which A represents a group chosen from among:

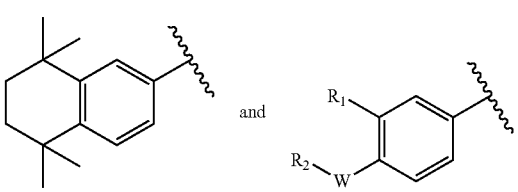

R1 is a branched alkyl radical or a substituted cycloalkyl radical;

R2 is a hydrogen atom, a linear alkyl radical or an alkyl radical substituted with an alkoxyl radical;

R3 is a hydrogen;

the central heterocycle

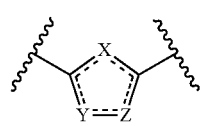

is a thiazolyl or oxadiazolyl ring.

According to another preferred embodiment, the compound according to the invention is a compound of formula (I) in which A represents a group chosen from among:

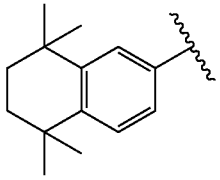 and 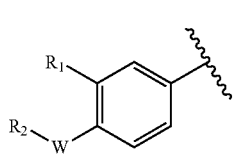

R1 is a tert-butyl or 1-methyl-cyclohexyl radical;
R2 is an ethoxymethyl radical;
W is O;
R3 is a hydrogen;
X represents S, Y represents CH and Z represents N; or X represents N, Y represents N and
Z represents O.

The present invention also relates to compounds of formula (I) such as described above as a medicament.

The compounds according to the invention are particularly well suited in the following fields of treatment:

1) dermatological conditions linked to a keratinization disorder pertaining to cellular differentiation and proliferation, especially to treat acne vulgaris, comedonic or polymorphic acne, rosacea, nodulocystic acne, acne conglobata, senile acne and secondary acnes such as solar, drug-induced or occupational acne;

2) keratinization disorders, especially ichthyosis, ichthyosiform states, lamellar ichthyosis, Darier disease, palmoplantar keratoderma, leukoplakia and leukoplakiform conditions, cutaneous or mucosal (buccal) lichen;

3) dermatological conditions with an inflammatory immuno-allergic component, with or without cellular proliferation problems, and in particular all forms of psoriasis, whether cutaneous, mucosal or ungual, and even arthropathia psoriatica, or alternatively cutaneous atopy such as eczema, or respiratory atopy or gingival hypertrophy;

4) skin disorders due to exposure to UV radiation and to repair or treat aging of the skin, whether photo-induced or chronological or to reduce pigmentation and actinic keratosis, or any pathologies associated with chronological or actinic aging, such as xerosis;

5) dermal or epidermal proliferations, whether benign or malignant, whether of viral origin or not such as common warts, flat warts and verruciform epidermodysplasia, oral florid papillomatoses, T lymphoma, and proliferations that can be induced by UV radiation, in particular basal and prickle cell epithelioma, as well as any precancerous cutaneous lesion such as keratoacanthoma;

6) dermatological disorders such as immune dermatoses like lupus erythematosus, bullous immune diseases and collagen diseases, such as scleroderma;

7) dermatological or general conditions with an immunological component;

8) ophthalmological problems, especially corneal diseases.

9) stigmata of epidermal and/or dermal atrophy induced by local or systemic corticosteroids, or any other form of cutaneous atrophy, 10) the treatment of any skin or general condition of viral origin, 11) to treat disorders of sebaceous function, such as hyperseborrhea associated with acne or simple seborrhea;

12) wound healing disorders, or to prevent or repair stretch marks, or to promote wound healing, 13) pigmentation disorders such as hyperpigmentation, melasma, hypopigmentation or vitiligo;

16) cancerous or precancerous conditions;

17) alopecia of various origins, notably alopecia due to chemotherapy or radiation.

The invention also has for a subject a pharmaceutical composition containing at least one compound of formula (I) such as defined above in a pharmaceutically-acceptable medium.

The present invention also has for a subject a novel medicinal composition intended for treatment of the above-mentioned conditions, which is characterized by the fact that it comprises, in a pharmaceutically-acceptable carrier and compatible with the selected mode of administration thereof, at least compound of formula (I), one of its optical isomers or one of its salts.

The composition according to the invention can be administered orally, enterally, parenterally, topically or by ocular administration. Preferably, the pharmaceutical composition is packaged in an appropriate form for topical application.

For oral administration, the composition may be in the form of tablets, hard capsules, lozenges, syrups, suspensions, solutions, powders, granulates, emulsions, suspensions of microspheres or nanospheres or lipid or polymer vesicles permitting controlled release. For parenteral administration, the composition is advantageously in the form of solutions or suspensions for infusion or for injection.

The compounds according to the invention are generally administered at a daily dosage of approximately 0.01 mg/kg to 100 mg/kg of bodyweight, in 1 to several doses.

The compounds are used systemically at a concentration generally comprised between 0.001% and 10% by weight, preferably between 0.01% and 1% by weight, relative to the weight of the composition.

For topical administration, the pharmaceutical composition according to the invention is more particularly intended for the treatment of the skin and the mucosa, and is in the liquid, paste or solid form, and more particularly in the form of ointments, creams, milks, salves, powders, impregnated pads, syndets, solutions, gels, sprays, foams, suspensions, sticks, shampoos or washing bases. They may also be in the form of suspensions of microspheres or nanospheres or lipid or polymer vesicles, or polymer patches and gels permitting controlled release.

The compounds are used topically at a concentration generally comprised between 0.001 and 10% by weight, preferably between 0.01% and 1% by weight, relative to the weight of the composition.

Compounds of formula (I) according to the invention also find application in the cosmetic field, in particular in body and hair hygiene and in particular for the treatment of acne-prone skin, for hair regrowth and loss prevention, to treat oily skin or hair, to protect against the harmful aspects of the sun or in the treatment of physiologically dry skin, to prevent and/or to treat photo-induced or chronological aging.

EXPERIMENTAL PART

A: Preparation of the Oxadiazole Compounds Described in Figure 1

Example 1: 4-{5-[3-adamantan-1-yl-4-(2-methoxy-ethoxymethoxy)-phenyl]-[1,3,4]-oxadiazol-2-yl}-benzoic acid 1.1: methyl 3-adamantan-1-yl-4-hydroxybenzoate 325 ml (5 mmol) of methane sulfonic acid are added dropwise to a solution of 31 g (200 mmol) of adamantanol and 31 g (200 mmol) of methyl 4-hydroxybenzoate in 3 L of dichloromethane and then the mixture is heated under reflux for 24 hours. After cooling to room temperature, the reaction medium is washed with water and then with a saturated solution of sodium bicarbonate. The organic phase is dried on magnesium sulfate then filtered and evaporated. The crude residue obtained is purified by silica gel chromatography eluted with a 97/3 heptane/ethyl acetate mixture. 25 g (44%) methyl 3-adamantan-1-yl-4-hydroxybenzoate are obtained.

1.2: methyl 3-adamantan-1-yl-4-(2-methoxy-ethoxymethoxy)-benzoate 4.2 g (105 mmol) of 60% of sodium hydride in hexane are added portionwise to a solution of 25 g (88 mmol) of methyl 3-adamantan-1-yl-4-hydroxy-benzoate in 100 ml of tetrahydrofuran and 100 ml of dimethylformamide. The reaction medium is stirred for 30 minutes and then 11 ml (96 mmol) of 1-chloromethoxy-2-methoxy-ethane are added dropwise and the reaction medium is stirred again at room temperature for one and a half hours. 150 ml of water are then added and the reaction medium is extracted with ethyl acetate. The organic phase is washed with water, dried on magnesium sulfate and then filtered and evaporated. 39 g of crude residue are obtained and purified by silica gel chromatography eluted with an 8/2 heptane/ethyl acetate mixture. 31.5 g (96%) of methyl 3-adamantan-1-yl-4-(2-methoxy-ethoxymethoxy)-benzoate are obtained in the form of a white solid.

1.3: 3-adamantan-1-yl-4-(2-methoxy-ethoxymethoxy)-benzohydrazide 11 ml (226 mmol) of hydrazine hydrate are added to a solution of 10 g (27 mmol) of methyl 3-adamantan-1-yl-4-(2-methoxy-ethoxymethoxy)-benzoate in 100 ml of methanol. The reaction medium is heated under reflux for 3 days. After cooling and addition of water, the reaction medium is extracted with ethyl acetate. The organic phase is washed with water, dried on magnesium sulfate and then filtered and evaporated. 10 g of crude residue are obtained and recrystallized in diethyl ether. 9.5 g (95%) of 3-adamantan-1-yl-4-(2-methoxy-ethoxymethoxy)-benzohydrazide are thus obtained in the form of a beige solid.

1.4: methyl 4-{N'-[3-adamantan-1-yl-4-(2-methoxy-ethoxymethoxy)-benzoyl]-hydrazinocarbonyl}-benzoate A solution of 5.8 g (29 mmol) of methyl 4-chlorocarbonyl-benzoate in 40 ml tetrahydrofuran is added dropwise to a solution of 11 g (29 mmol) of 3-adamantan-1-yl-4-(2-methoxy-ethoxymethoxy)-benzohydrazide in 80 ml of tetrahydrofuran. 1.1 g (10% by mass) of 4-dimethylamino-pyridine are added and the reaction medium is stirred for 24 hours at room temperature. Water is added and the reaction medium is extracted with ethyl acetate. The organic phase is washed with water, dried on magnesium sulfate and then filtered and evaporated. 15.4 g of crude reside are obtained and purified by successive recrystallizations in dichloromethane and then diethyl ether. 9.6 g (60%) of methyl 4-{N'-[3-adamantan-1-yl-4-(2-methoxy-ethoxymethoxy)-benzoyl]-hydrazinocarbonyl}-benzoate are obtained.

1.5: methyl 4-{5-[3-adamantan-1-yl-4-(2-methoxy-ethoxymethoxy)-phenyl]-[1,3,4]oxadiazol-2-yl}-benzoate 3.7 ml (46 mmol) of pyridine and then 1.7 ml (23 mmol) of thionyl chloride are added to a solution of 9.6 g (18 mmol) of methyl 4-{N'-[3-adamantan-1-yl-4-(2-methoxy-ethoxymethoxy)-benzoyl]-hydrazinocarbonyl}-benzoate in 100 ml of diethyl ether, previously cooled to 0° C. The reaction medium is stirred from 0° C. to room temperature for 4 hours and then 100 ml of toluene are added and the medium is heated under reflux for two and a half hours. After cooling, the reaction medium is filtered, the precipitate is rinsed with tetrahydrofuran and then the concentrated filtrate. 15 g of crude residue are obtained and purified by silica gel chromatography eluted with a 7/3 heptane/ethyl acetate mixture. 8 g (87%) of methyl 4-{5-[3-adamantan-1-yl-4-(2-methoxy-ethoxymethoxy)-phenyl]-[1,3,4]oxadiazol-2-yl} benzoate are obtained.

1.6: 4-{5-[3-adamantan-1-yl-4-(2-methoxy-ethoxymethoxy)-phenyl]-[1,3,4]-oxadiazol-2-yl}-benzoic acid 0.8 ml (0.8 mmol) of a 1 M aqueous lithium hydroxide solution are added to a solution of 0.2 g (0.4 mmol) of methyl 4-{5-[3-adamantan-1-yl-4-(2-methoxy-ethoxymethoxy)-phenyl]-[1,3,4] oxadiazol-2-yl}-benzoate in 9 ml of tetrahydrofuran and 3 ml of methanol. The reaction medium is heated under reflux for 6 hours and then cooled, acidified to pH 5 with 1 M aqueous hydrochloric acid solution and extracted with ethyl acetate. The organic phase is then dried on magnesium sulfate, filtered and evaporated. 350 mg of crude residue are obtained and purified by silica gel chromatography eluted with a 7/3 heptane/ethyl acetate mixture. 150 mg (77%) of 4-{5-[3-adamantan-1-yl-4-(2-methoxy-ethoxymethoxy)-phenyl]-[1,3,4]oxadiazol-2-yl}-benzoic acid are obtained.

Example 2: 4-[5-(3-adamantan-1-yl-4-methoxy-phenyl)-[1,3,4]oxadiazol-2-yl]-benzoic acid 2.1: methyl 4-[5-(3-adamantan-1-yl-4-hydroxy-phenyl)-[1,3,4]oxadiazol-2-yl]-benzoate 3 ml of a commercial solution of concentrated sulfuric acid are added to a solution of 7.8 g (15 mmol) of 4-{5-[3-adamantan-1-yl-4-(2-methoxy-ethoxymethoxy)]-phenyl-[1,3,4]oxadiazol-2-yl}-benzoate (prepared as described in Example 1.5) in 60 ml of methanol and 70 ml of tetrahydrofuran. The reaction medium is stirred at room temperature for 18 hours and then filtered. The filtrate is brought to pH 7 by addition of an aqueous solution of sodium hydroxide and extracted with ethyl acetate. The organic phase is washed with water, dried on magnesium sulfate and then filtered and evaporated. 5.8 g (90%) of methyl 4-[5-(3-adamantan-1-yl-4-hydroxy-phenyl)-[1,3,4]oxadiazol-2-yl]-benzoate are thus obtained.

2.2: methyl 4-[5-(3-adamantan-1-yl-4-methoxy-phenyl)-[1,3,4]oxadiazol-2-yl]-benzoate A solution of 250 mg (0.6 mmol) of methyl 4-[5-(3-adamantan-1-yl-4-hydroxyphenyl)-[1,3,4]oxadiazol-2-yl] benzoate, 36 mg (0.6 mmol) of potassium hydroxide and 40 ml (0.7 mmol) of methyl iodide in 20 ml of diglyme is heated under reflux for 5 hours in a closed tube After cooling, water is added and the medium is extracted with ethyl acetate. The organic phase is dried on magnesium sulfate then filtered and evaporated. 260 mg (100%) of methyl 4-[5-(3-adamantan-1-yl-4-methoxy-phenyl)-[1,3,4]oxadiazol-2-yl]-benzoate are obtained.

2.3: 4-[5-(3-adamantan-1-yl-4-methoxy-phenyl)-[1,3,4]oxadiazol-2-yl]-benzoic acid 0.7 ml (0.7 mmol) of a 1 M aqueous sodium hydroxide solution are added to a solution of 250 mg (0.6 mmol) of methyl 4-[5-(3-adamantan-1-yl-4-methoxy-phenyl)-[1,3,4] oxadiazol-2-yl]-benzoate in 10 ml of tetrahydrofuran and 4 ml of methanol. After stirring at room temperature for 6 hours, the reaction medium is acidified to pH 3-4 by addition of a 1 M aqueous hydrochloric acid solution. The product precipitates and is filtered, rinsed with water and dried under vacuum. 212 mg (85%) of 4-[5-(3-adamantan-1-yl-4-methoxyphenyl)-[1,3,4]oxadiazol-2-yl]-benzoic acid are obtained.

| Example no. in experimental part | Chemical structure | Compound name | Synthesis pathway | 1H NMR | Appearance |
| --- | --- | --- | --- | --- | --- |
| Example 1 | 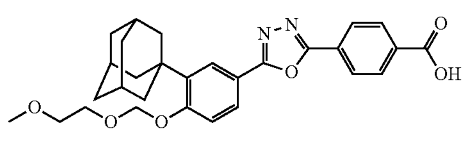 [SMILES: COCCOCOc1ccc(-c2nnc(-c3ccc(C(=O)O)cc3)o2)cc1C12CC3CC(CC(C3)C1)C2] | 4-{5-[3-adamantan-1-yl-4-(2-methoxy-ethoxymethoxy)-phenyl]-[1,3,4]oxadiazol-2-yl}-benzoic acid | A (Figure 1) | $^1$H NMR (400 MHz, CDCl$_3$); δ (ppm) 8.13 (m, 4H); 7.95 (d, J = 2.2 Hz, 1 H); 7.65 (dd, J = 8.6, 2.1 Hz, 1 H); 7.21 (d, J = 8.6 Hz, 1 H); 5.34 (s, 2 H); 3.81 (dd, J = 5.6, 3.5 Hz, 2 H); 3.53 (m, J = 4.4 Hz, 2 H); 3.32 (s, 3 H); 2.09 (s, 6 H); 2.04 (s, 3 H); 1.73 (s, 6 H). | white solid |
| Example 2 | 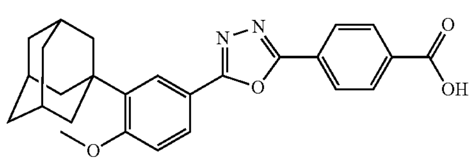 [SMILES: COc1ccc(-c2nnc(-c3ccc(C(=O)O)cc3)o2)cc1C12CC3CC(CC(C3)C1)C2] | 4-[5-(3-adamantan-1-yl-4-methoxy-phenyl)-[1,3,4]oxadiazol-2-yl]-benzoic acid | A (Figure 1) | $^1$H NMR (400 MHz, CDCl$_3$); δ (ppm) 8.10 (m, 4H); 7.90 (d, J = 2.2 Hz, 1 H); 7.66 (dd, J = 8.5, 2.1 Hz, 1 H); 6.91 (d, J = 8.5 Hz, 1 H); 3.83 (s, 3 H); 2.05 (s, 6 H); 2.01 (s, 3 H); 1.70 (s, 6 H). | white solid |
| | | 4-[5-(3-adamantan-1-yl-4-hydroxy-phenyl)-[1,3,4]oxadiazol-2-yl]-benzoic acid | A (Figure 1) | $^1$H NMR (400 MHz, DMSO); δ (ppm) 10.37 (m, 1 H); 8.16 (s, 4 H); 7.79-7.83 (m, 2 H); 7.00 (d, J = 8.3 Hz, 1 H); 2.14 (s, 6 H); 2.08 (s, 3 H); 1.78 (s, 6 H). | beige solid |
| | | 4-[5-[3-adamantan-1-yl-4-isobutoxy-phenyl)-[1,3,4]oxadiazol-2-yl]-benzoic acid | A (Figure 1) | $^1$H NMR (400 MHz, CDCl$_3$); δ (ppm) 8.09-8.11 (m, 4 H); 7.80 (d, J = 2.2 Hz, 1 H); 7.83 ((dd, J = 8.6 Hz et 2.2 Hz, 1 H); 6.69 (d, J = 8.6 Hz, 1 H); 3.76 (d, J = 6.3 Hz, 2 H); 2.51 (m, 1 H); 2.09 (s, 6 H); 2.02 (s, 3 H); 1.71 (s, 6 H); 1.05 (d, J = 6.7 Hz, 6 H). | beige solid |

| Example no. in experimental part | Chemical structure | Compound name | Synthesis pathway | 1H NMR | Appearance |
|---|---|---|---|---|---|
| | | 4-[5-(3-adamantan-1-yl-4-ethoxy-phenyl)-[1,3,4]oxadiazol-2-yl]-benzoic acid | A (Figure 1) | $^1$H NMR (400 MHz, CDCl$_3$); δ (ppm) 8.02 (m, 4 H); 7.81 (d, J = 2.3 Hz, 1 H); 7.75 (dd, J = 6.5, 2.2 Hz, 1 H); 8.81 (d, J = 8.5 Hz, 1 H); 3.99 (q, J = 6.9 Hz, 2 H); 2.01 (s, 5 H); 1.94 (s, 5 H); 1.64 (s, 6 H); 1.37 (t, J = 6.9 Hz, 3 H). | white solid |
| | | 4-[5-(3-adamantan-1-yl-4-cyclopropylmethoxy-phenyl)-[1,3,4]oxadiazol-2-yl]-benzoic acid | A (Figure 1) | $^1$H NMR (400 MHz, CDCl$_3$); δ (ppm) 8.05 (m, 4 H); 7.84 (s, 1 H); 7.77 (d, J = 8.6 Hz, 1 H); 6.79 (d, J = 8.5 Hz, 1 H); 3.79 (d, J = 8.9 Hz, 2 H); 2.07 (s, 6 H); 1.98 (s, 3 H); 1.88 (s, 8 H); 0.73 (s, 1 H); 0.56 (d, J = 7.8 Hz, 2 H); 0.28 (d, J = 5.1 Hz, 2 H). | white solid |
| | | 4-[5-[3-adamantan-1-yl-4-(2,2,2-trifluoro-ethoxy)-phenyl]-[1,3,4]oxadiazol-2-yl]-benzoic acid | A (Figure 1) | $^1$H NMR (400 MHz, CDCl$_3$); δ (ppm) 8.00 (m, 4 H); 7.85 (d, J = 2.2 Hz, 1 H); 7.78 (dd, J = 8.5, 2.2 Hz, 1 H); 8.75 (d, J = 8.5 Hz, 1 H); 4.32 (q, J = 8.0 Hz, 2 H); 1.94 (m, 9 H); 1.88 (s, 8 H); 0.73 (s, 1 H); 0.56 (d, J = 7.8 Hz, 2 H); 1.60 (s, 6 H). | white solid |
| | | 4-[5-(3-adamantan-1-yl-4-propoxy-phenyl)-[1,3,4]oxadiazol-2-yl]-benzoic acid | A (Figure 1) | $^1$H NMR (400 MHz, CDCl$_3$); δ (ppm) 7.98 (m, 4 H); 7.76 (d, J = 2.3 Hz, 1 H); 7.71 (dd, J = 8.5, 2.3 Hz, 1 H); 8.78 (d, J = 8.5 Hz, 1 H); 3.84 (t, J = 8.3 Hz, 2 H); 1.97 (s, 8 H); 1.90 (s, 3 H); 1.58 (s, 6 H); 0.94 (t, J = 7.4 Hz, 3 H). | white solid |
| | | 4-{5-[3-adamantan-1-yl-4-(2,2-dimethoxy-ethoxy)-phenyl]-[1,3,4]oxadiazol-2-yl}-benzoic acid | A (Figure 1) | $^1$H NMR (400 MHz, CDCl$_3$); δ (ppm) 8.14 (m, 4 H); 7.84 (d, J = 2.2 Hz, 1 H); 7.87 (dd, J = 8.5, 2.1 Hz, 1 H); 8.89 (d, J = 8.5 Hz, 1 H); 4.80 (t, J = 5.3 Hz, 1 H); 4.03 (d, J = 8.3 Hz, 2 H); 3.43 (s, 6 H); 2.12 (s, 6 H); 2.06 (s, 3 H); 1.74 (s, 6 H). | white solid |
| | | 4-{5-[3-adamantan-1-yl-4-([1,3]dioxolen-2-ylmethoxy)-phenyl]-[1,3,4]oxadiazol-2-yl}-benzoic acid | A (Figure 1) | $^1$H NMR (400 MHz, CDCl$_3$); δ (ppm) 8.10 (m, 4 H); 7.91 (d, J = 2.3 Hz, 1 H); 7.84 (dd, J = 8.5, 2.3 Hz, 1 H); 8.89 (d, J = 8.5 Hz, 1 H); 5.29 (t, J = 3.8 Hz, 1 H); 4.04 (d, J = 3.9 Hz, 2 H); 3.98 (m, 2 H); 3.89-3.91 (m, 2 H); 2.07 (s, 6 H); 2.01 (s, 3 H); 1.89 (s, 6 H). | white solid |

| Example no. in experimental part | Chemical structure | Compound name | Synthesis pathway | 1H NMR | Appearance |
|---|---|---|---|---|---|
| | | 4-[5-(3-tert-butyl-4-hydroxy-phenyl)-[1,3,4]oxadiazol-2-yl]-benzoic acid | A (Figure 1) | | |
| | | 4-[5-(3-tert-butyl-4-ethoxy-phenyl)-[1,3,4]oxadiazol-2-yl]-benzoic acid | A (Figure 1) | | |
| | | 4-[5-(4-hydroxy-3-pyrrolidin-1-yl-phenyl)-[1,3,4]oxadiazol-2-yl]-benzoic | A (Figure 1) | | |
| | | methyl 4-[5-(4-hydroxy-3-pyrrolidin-1-yl-phenyl)-[1,3,4]oxadiazol-2-yl]-benzoate | A (Figure 1) | | |

B: Preparation of the Oxadiazole Compounds Described in Figure 2

Example 3: 4-[3-(3-tert-butyl-4-hydroxy-phenyl)-[1,2,4]oxadiazol-5-yl]-benzoic acid 3.1: 4-bromo-2-tert-butylphenol 47 g (98 mmol) of tetrabutylammonium bromide are added portionwise to a solution of 15 ml (98 mmol) of 2-tert-butylphenol in 300 ml of chloroform. The reaction medium is stirred at room temperature for 1 hour and then hydrolyzed by addition of 300 ml of a saturated aqueous sodium thiosulfate solution and extracted with dichloromethane. The organic phases are collected, washed with water, dried on magnesium sulfate and then filtered and evaporated. The crude residue obtained is taken up in diethyl ether and the remaining inorganic salts precipitate. The medium is filtered and the ether phase is washed with a saturated sodium chloride solution, dried on magnesium sulfate, filtered and evaporated 22 g (100%) of 4-bromo-2-tert-butylphenol are obtained in the form of a light yellow oil.

3.2: 4-bromo-2-tert-butyl-1-ethoxymethoxy-benzene 4.7 g (117 mmol) of sodium hydride are added portionwise to a solution of 22.4 g (98 mmol) of 4-bromo-2-tert-butylphenol in a mixture of 100 ml of tetrahydrofuran and 100 ml of dimethylformamide. After stirring at room temperature for 20 minutes, 10 ml (107 mmol) of chloromethoxy-ethane are added dropwise and then the reaction medium is stirred for 2 hours at room temperature. After hydrolysis by addition of water, the reaction medium is extracted with ethyl acetate. The organic phase is washed with a saturated solution of sodium chloride, dried on magnesium sulfate, filtered and evaporated 31.5 g of crude residue are obtained and purified by silica gel chromatography eluted with a heptane/ethyl acetate mixture, increasing the polarity regularly until a 9/1 ratio is obtained. 20 g (71%) of 4-bromo-2-tert-butyl-1-ethoxymethoxy-benzene are obtained in the form of a yellow oil.

3.3: 3-tert-butyl-4-ethoxymethoxy-benzonitrile 6.8 g (77 mmol) of copper cyanide are added portionwise to a solution of 20 g (70 mmol) of 4-bromo-2-tert-butyl-1-ethoxymethoxybenzene in 200 ml of dimethylformamide and 1 ml of pyridine. The reaction medium is stirred to reflux for 5 hours and then filtered. After the addition of water and dilution with ethyl acetate, the reaction medium is extracted with ethyl acetate. The organic phase is washed many times with water and then the organic phase is dried on magnesium sulfate, filtered and evaporated. 17 g of crude residue are obtained and purified by silica gel chromatography eluted with a heptane/ethyl acetate mixture, increasing the polarity regularly until a 9/1 ratio is obtained. 9.6 g (59%) of 3-tert-butyl-4-ethoxymethoxy-benzonitrile are obtained in the form of a brown oil.

3.4: 3-tert-butyl-4-ethoxymethoxy-N-hydroxy-benzamidine 4.3 g (62 mmol) of hydroxylamine hydrochloride are added portionwise to a solution of 9.6 g (41 mmol) of 3-tert-butyl-4-ethoxymethoxybenzonitrile in 100 ml of ethanol. A solution of 2.5 g (62 mmol) of sodium hydroxide in 20 ml of water is then added dropwise to the preceding mixture. The reaction medium is then heated under reflux for 24 hours and hydrolyzed by addition of water and extracted with ethyl acetate. The organic phase is washed with a saturated sodium chloride solution, dried on magnesium sulfate, filtered and evaporated. 11 g of crude residue are obtained and purified by silica gel chromatography eluted with a heptane/ethyl acetate mixture, increasing the polarity regularly until a 5/5 ratio is obtained in each of the solvents. 5.2 g (48%) of 3-tert-butyl-4-ethoxymethoxy-N-hydroxy-benzamidine are obtained in the form of a white solid.

3.5: methyl 4-[3-(3-tert-butyl-4-ethoxymethoxy-phenyl)-[1,2,4]oxadiazol-5-yl]-benzoate A suspension of 5 g (25 mmol) of methyl 4-chlorocarbonyl-benzoate in 25 ml of pyridine is added to a solution of 5.2 g (20 mmol) of 3-tert-butyl-4-ethoxymethoxy-N-hydroxybenzamidine in 50 ml of pyridine. The reaction medium is then heated under reflux for 30 minutes. After cooling, water is added and the medium is extracted with dichloromethane. The organic phase is washed with water, dried on magnesium sulfate and then filtered and evaporated. 9 g of crude residue are obtained and purified by silica gel chromatography eluted with heptane. 7 g (87%) of methyl 4-[3-(3-tert-butyl-4-ethoxymethoxy-phenyl)-[1,2,4] oxadiazol-5-yl] benzoate are obtained as a white solid.

3.6: 4-[3-(3-tert-butyl-4-ethoxymethoxy-phenyl)-[1,2,4]oxadiazol-5-yl]-benzoic acid 19 ml (19 mmol) of a 1 M aqueous lithium hydroxide solution are added to a solution of 6.5 g (16 mmol) of methyl 4-[3-(3-tert-butyl-4-ethoxymethoxy-phenyl)-[1,2,4]oxadiazol-5-yl]-benzoate in 70 ml of tetrahydrofuran. The reaction medium is stirred at room temperature for 5 hours and then acidified to pH 3-4 by addition of a 1 M aqueous hydrochloric acid solution. The product precipitates. After filtration and rinsing of the solid obtained with water and then with heptane, 6 g of crude residue are obtained and purified by silica gel chromatography eluted with a 8/2 heptane/ethyl acetate mixture. 4.8 g (76%) of 4-[3-(3-tert-butyl-4-ethoxymethoxy-phenyl)-[1,2,4]oxadiazol-5-yl]-benzoic acid are obtained in the form of a white solid.

3.7: Methyl 4-[3-(3-tert-butyl-4-hydroxy-phenyl)-[1,2,4]oxadiazol-5-yl]-benzoate 1 ml of concentrated sulfuric acid is added to a 0.9 g (2.3 mmol) solution of methyl 4-[3-(3-tert-butyl-4-ethoxymethoxy-phenyl)-[1,2,4]oxadiazol-5-yl]-benzoate in a mixture of 15 ml of methanol and 15 ml of tetrahydrofuran. The reaction medium is stirred at room temperature for 20 hours and then heated at 50° C. for 7 hours. After addition of water, the product precipitates. The precipitate is filtered and rinsed with water then with heptane. 0.75 g (94%) of methyl 4-[3-(3-tert-butyl-4-hydroxy-phenyl)-[1,2,4]oxadiazol-5-yl]-benzoate are obtained.

3.8: 4-[3-(3-tert-butyl-4-hydroxy-phenyl)-[1,2,4]oxadiazol-5-yl]-benzoic acid 1.8 ml (1.8 mmol) of a 1 M aqueous lithium hydroxide solution are added to a solution of 0.3 g (0.9 mmol) of methyl 4-[3-(3-tert-butyl-4-hydroxyphenyl)-[1,2,4] oxadiazol-5-yl]-benzoate in 8 ml of tetrahydrofuran. The reaction medium is stirred at room temperature for 24 hours and then acidified to pH 3-4 by addition of a 1 M aqueous hydrochloric acid solution. The product precipitates. After filtration and rinsing of the solid obtained with water and then with heptane, 0.25 g (86%) of 4-[3-(3-tert-butyl-4-hydroxy-phenyl)-[1,2,4]oxadiazol-5-yl]-benzoic acid are obtained.

Example 4: 4-[3-(3-tert-butyl-4-ethoxy-phenyl)-[1,2,4]oxadiazol-5-yl]-benzoic acid

4.1: Methyl 4-[3-(3-tert-butyl-4-ethoxy-phenyl)-[1,2,4]oxadiazol-5-yl]-benzoate 60 μl (0.7 mmol) of ethyl iodide are added to a mixture of 200 mg (0.6 mmol) of methyl 4-[3-(3-tert-butyl-4-hydroxy-phenyl)-[1,2,4]oxadiazol-5-yl]-benzoate (prepared as described in Example 1.7) and 300 mg (0.9 mmol) of cesium carbonate in 10 ml of dimethylformamide. The reaction mixture is heated at 80° C. for 18 h. After cooling, the reaction medium is filtered then evaporated. The crude residue obtained is purified by silica gel chromatography and eluted with a 1/1 heptane/ethyl acetate mixture. 188 mg (87%) of methyl 4-[3-(3-tert-butyl-4-ethoxy-phenyl)-[1,2,4] oxadiazol-5-yl]-benzoate are obtained.

4.2: 4-[3-(3-tert-butyl-4-ethoxy-phenyl)-[1,2,4]oxadiazol-5-yl]-benzoic acid 750 μl (0.75 mmol) of 1 M aqueous lithium hydroxide solution are added to a solution of 188 mg (0.50 mmol) of methyl 4-[3-(3-tert-butyl-4-ethoxyphenyl)-[1,2,4]oxadiazol-5-yl]-benzoate in 6 ml of tetrahydrofuran and 0.5 ml of water. The reaction medium is stirred at room temperature for 20 hours and then the tetrahydrofuran is evaporated. After dilution with water and acidification by a 1 M aqueous hydrochloric acid solution, the product precipitates. After filtration and rinsing the precipitate with water and heptane, 125 mg (68%) of 4-[3-(3-tert-butyl-4-ethoxyphenyl)-[1,2,4] oxadiazol-5-yl]-benzoic acid are obtained.
1H NMR (δ, DMSO): 1.41 (s, 9H), 7 (d, J=8.4 Hz, 1H), 7.8 (dd, J=8.4-2.1 Hz, 1H), 7.9 (d, J=2.1 Hz, 1H), 8.18 (dd, J=6.8-1.8 Hz, 2H), 8.3 (dd, J=6.7-1.7 Hz, 2H).

Example 5: 4-{3-[3-(1-methyl-cyclohexyl)-4-propoxy-phenyl]-[1,2,4]oxadiazol-5-yl}-benzoic acid

5.1: 4-bromo-2-(1-methylcyclohexyl)-phenol 2 ml (31 mmol) of methanesulfonic acid are added to a solution of 4.7 g (41 mmol) of 1-methylcyclohexanol and 7 g (40 mmol) of 4-bromophenol in 25 ml of dichloromethane and the mixture is heated under reflux for 24 hours. After cooling to room temperature, the reaction medium is washed with water and then with a saturated sodium bicarbonate solution. The organic phase is dried on magnesium sulfate then filtered and evaporated. The crude residue obtained is purified by silica gel chromatography eluted with a 97/3 heptane/ethyl acetate mixture. 4.7 g (44%) of 4-bromo-2-(1-methyl-cyclohexyl)-phenol are obtained.

5.2: 4-bromo-1-ethoxymethoxy-2-(1-methyl-cyclohexyl)-benzene 0.8 g (20 mmol) of 60% sodium hydride in heptane are added portionwise to a solution of 4.5 g (17 mmol) of 4-bromo-2-(1-methylcyclohexyl)-phenol in 20 ml of tetrahydrofuran and 20 ml of dimethylformamide. The reaction medium is stirred for 20 minutes at room temperature and then 1.7 ml (19 mmol) of chloromethoxyethane are added. After stirring for 2 hours at room temperature, the medium is hydrolyzed by adding water and then extracted with ethyl acetate. The organic phase is washed with a saturated sodium chloride solution, dried on magnesium sulfate, filtered and evaporated. 5.1 g of crude residue obtained are purified by silica gel chromatography eluted with a heptane/ethyl acetate mixture, increasing the polarity regularly until a 9/1 ratio is obtained. 4.9 g (89%) of 4-bromo-1-ethoxymethoxy-2-(1-methyl-cyclohexyl)-benzene are obtained in the form of a brown oil.

5.3: 4-ethoxymethoxy-3-(1-methyl-cyclohexyl)-benzonitrile 1.4 g (16 mmol) of copper cyanide are added to a solution of 4.8 g (15 mmol) of 4-ethoxymethoxy-3-(1-methyl-cyclohexyl)-benzonitrile in 50 ml of dimethylformamide and 1 ml of pyridine. The reaction medium is stirred under reflux for 10 hours then cooled and diluted with ethyl acetate. After filtration, the organic phase is washed with water, dried on magnesium sulfate and then filtered and evaporated. 10 g of crude residue are obtained and purified by silica gel chromatography eluted with a heptane/ethyl acetate mixture, increasing the polarity regularly until a 9/1 ratio is obtained. 1.8 g (46%) of 4-ethoxymethoxy-3-(1-methyl-cyclohexyl)-benzonitrile are obtained in the form of a yellow oil.

5.4: 4-ethoxymethoxy-N-hydroxy-3-(1-methyl-cyclohexyl)-benzamidine 0.7 g (10 mmol) of hydroxylamine hydrochloride followed by 0.4 g (10 mmol) of sodium hydroxide previously diluted in 5 ml of water are added to a solution of 1.8 g (7 mmol) of 4-ethoxymethoxy-3-(1-methyl-cyclohexyl)-benzonitrile in 25 ml of ethanol. The reaction medium is heated under reflux for 24 hours. After cooling and addition of water, the medium is extracted with ethyl acetate. The organic phase is washed with a saturated sodium chloride solution, dried on magnesium sulfate, filtered and evaporated. 2.2 g of crude residue are obtained and purified by silica gel chromatography eluted with a 7/3 heptane/ethyl acetate mixture. 1.5 g (76%) of 4-ethoxymethoxy-N-hydroxy-3-(1-methyl-cyclohexyl)-benzamidine are obtained.

5.5: methyl 4-{3-[4-ethoxymethoxy-3-(1-methyl-cyclohexyl)-phenyl]-[1,2,4]oxadiazol-5-yl}-benzoate A suspension of 1 g (5 mmol) of methyl 4-chlorocarbonyl-benzoate in 15 ml of pyridine is added to a solution of 1.5 g (5 mmol) of 4-ethoxymethoxy-N-hydroxy-3-(1-methylcyclohexyl)-benzamidine in 15 ml of pyridine. The reaction medium is heated under reflux for 30 minutes and then cooled, diluted with dichloromethane and washed with water. The organic phase is dried on magnesium sulfate then filtered and evaporated. 1.7 g (75%) of methyl 4-{3-[4-ethoxymethoxy-3-(1-methyl-cyclohexyl)-phenyl]-[1,2,4]oxadiazol-5-yl}-benzoate are obtained.

5.6: 4-{3-[4-ethoxymethoxy-3-(1-methyl-cyclohexyl)-phenyl]-[1,2,4]oxadiazol-5-yl}-benzoic acid In a similar manner to Example 3.6, from 1.7 g (4 mmol) of methyl 4-{3-[4-ethoxymethoxy-3-(1-methyl-cyclohexyl)-phenyl]-[1,2,4]oxadiazol-5-yl}-benzoate, 1.3 g (76%) 4-{3-[4-ethoxymethoxy-3-(1-methyl-cyclohexyl)-phenyl]-[1,2,4]oxadiazol-5-yl}-benzoic acid are obtained in the form of a white solid.

5.7: methyl 4-{3-[4-hydroxy-3-(1-methyl-cyclohexyl)-phenyl]-[1,2,4]oxadiazol-5-yl}-benzoate In a similar manner to Example 3.7, from 1.1 g (3 mmol) of methyl 4-{3-[4-ethoxymethoxy-3-(1-methyl-cyclohexyl-phenyl]-[1,2,4]oxadiazol-5-yl}-benzoate, 0.9 g (93%) of methyl 4-{3-[4-hydroxy-3-(1-methylcyclohexyl)-phenyl]-[1,2,4] oxadiazol-5-yl}-benzoate are obtained.

5.8: Methyl 4-{3-[3-(1-methyl-cyclohexyl)-4-propoxy-phenyl]-[1,2,4]oxadiazol-5-yl}-benzoate In a similar manner to Example 4.1, from 150 mg (0.4 mmol) of methyl 4-{3-[4-hydroxy-3-(1-methyl-cyclohexyl)-phenyl]-[1,2,4]oxadiazol-5-yl}-benzoate and 55 µl (1.6 mmol) of n-propyl iodine, 135 mg (82%) of methyl 4-{3-[3-(1-methyl-cyclohexyl)-4-propoxyphenyl]-[1,2,4] oxadiazol-5-yl}-benzoate are obtained.

5.9 4-{3-[3-(1-methyl-cyclohexyl)-4-propoxy-phenyl]-[1,2,4]oxadiazol-5-yl}-benzoic acid In a similar manner to Example 4.2, from 135 mg (0.3 mmol) of methyl 4-{3-[3-(1-methyl-cyclohexyl)-4-propoxy-phenyl]-[1,2,4]oxadiazol-5-yl}-benzoate, 85 mg (65%) of 4-{3-[3-(1-methyl-cyclohexyl)-4-propoxy-phenyl]-[1,2,4]oxadiazol-5-yl}-benzoic acid are obtained in the form of a white solid.

| Example no. in experimental part | Chemical structure | Compound name | Synthesis pathway | 1H NMR | Appearance |
|---|---|---|---|---|---|
| Example 3 | 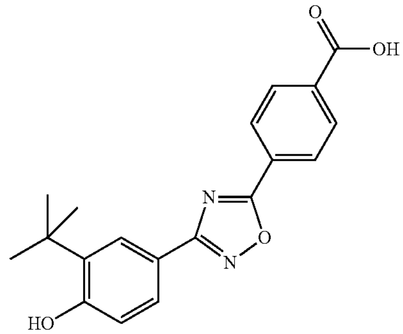 [SMILES: CC(C)(C)c1cc(-c2noc(-c3ccc(C(=O)O)cc3)n2)ccc1O] | 4-[3-(3-tert-butyl-4-hydroxy-phenyl)-[1,2,4]oxadiazol-5-yl]-benzoic acid | B (Figure 2) | $^1$H NMR (400 MHz, DMSO): δ (ppm) 13.45 (br s, 1 H); 10.20 (s, 1 H); 8.29 (d, J = 8.3 Hz, 2 H); 8.16 (d, J = 8.3 Hz, 2 H); 7.93 (d, J = 2.1 Hz, 1 H); 7.80 (dd, J = 8.3, 2.1 Hz, 1 H); 6.98 (d, J = 8.3 Hz, 1 H); 1.42 (s, 9 H). | white solid |
| example 4 | 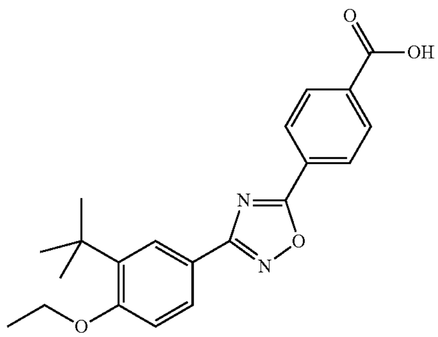 [SMILES: CCOc1ccc(-c2noc(-c3ccc(C(=O)O)cc3)n2)cc1C(C)(C)C] | 4-[3-(3-tert-butyl-4-ethoxy-phenyl)-[1,2,4]oxadiazol-5-yl]-benzoic acid | B (Figure 2) | $^1$H NMR (400 MHz, DMSO): δ (ppm) 8.20 (d, J = 8.1 Hz, 2 H); 7.95 (s, 1 H); 7.88 (d, J = 8.5 Hz, 1 H); 6.94 (d, J = 8.5 Hz, 1 H); 4.09 (q, J = 7.0 Hz, 2 H); 1.44 (t, J = 7.0 Hz, 3H); 1.38 (s, 9 H). | white solid |
| example 5 | 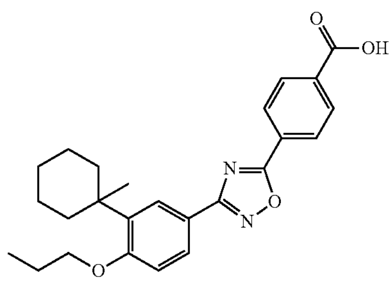 [SMILES: CCCOc1ccc(-c2noc(-c3ccc(C(=O)O)cc3)n2)cc1C1(C)CCCCC1] | 4-(3-[3-(1-methyl-cyclohexyl)-4-propoxy-phenyl]-[1,2,4]oxadiazol-5-yl]-benzoic acid | B (Figure 2) | $^1$H NMR (400 MHz, DMSO): δ (ppm) 13.4 (br s, 1H); 6.28 (d, J = 8.1 Hz, 2 H); 8.18 (d, J = 8.1 Hz, 2 H); 8.00 (s, 1 H); 7.91 (d, J = 8.5 Hz, 1 H); 7.15 (d, J = 8.6 Hz, 1 H); 4.04 (m, 2 H); 2.15 (m, 2 H); 1.82 (m, 2 H); 1.73 (m, 2 H); 1.47-1.57 (br m, 4 H); 1.33 (s, 3 H); 1.05 (t, J = 7.4 Hz, 3 H). | white solid |
| | | 4-[3-(3-adamantan-1-yl-4-ethoxymethoxy-phenyl)-[1,2,4]oxadiazol-5-yl]-benzoic acid | B (Figure 2) | $^1$H NMR (400 MHz, DMSO): δ (ppm) 8.24 (d, J = 8.1 Hz, 2 H); 8.17 (d, J = 8.2 Hz, 2 H); 8.00 (d, J = 2.1 Hz, 1 H); 7.91 (dd, J = 8.5, 2.0 Hz, 1 H); 7.18 (d, J = 8.6 Hz, 1 H); 5.30 (s, 2 H); 3.74 (q, J = 7.1 Hz, 2 H); 2.13 (s, 6 H); 2.06 (s, 3 H); 1.75 (s, 6 H); 1.22 (t, J = 7.1 Hz, 3 H). | white solid |
| | | 4-[3-(3-adamantan-1-yl-4-hydroxy-phenyl)-[1,2,4]oxadiazol-5-yl]-benzoic acid | B (Figure 2) | $^1$H NMR (400 MHz, CDCl$_3$): δ (ppm) 8.88 (s, 1 H); 8.20 (d, J = 8.2 Hz, 2 H); 8.14 (d, J = 8.2 Hz, 2 H); 7.91 (d, J = 2.1 Hz, 1 H); 7.74 (dd, J = 8.3, 2.1 Hz, 1 H); 6.84 (d, J = 8.3 Hz, 1 H); 2.13 (s, 6 H); 2.02 (s, 3 H); 1.72 (s, 6 H). | white solid |

-continued

| Example no. in experimental part | Chemical structure | Compound name | Synthesis pathway | 1H NMR | Appearance |
|---|---|---|---|---|---|
| | | 4-{3-[3-adamantan-1-yl-4-(2-methoxy-ethoxy)-phenyl]-[1,2,4]oxadiazol-5-yl}-benzoic acid | B (Figure 2) | $^1$H NMR (400 MHz, DMSO): δ (ppm) 8.22 (s, 4 H); 7.91 (s, 2 H); 7.16 (d, J = 7.8 Hz, 1 H); 4.19 (s, 2 H); 3.75 (s, 2 H); 3.34 (s, 3 H); 2.11 (s, 6 H); 2.04 (s, 3 H); 1.73 (s, 6 H). | brown solid |
| | | 4-{3-[3-adamantan-1-yl-4-(2-dimethylamino-ethoxy)-phenyl]-[1,2,4]oxadiazol-5-yl}-benzoic acid | B (Figure 2) | 1H NMR (400 MHz, DMSO): δ (ppm) 8.10-8.12 (m, 4 H); 7.8 (M, 1H); 7.49 (s, 1 H); 6.73 (M, 1 H); 4.36 (t, J = 5.8 Hz, 2 H); 3.11 (M, 2 H); 2.13 (M, 6 H); 1.99 (M, 3 H); 1.70 (t, J = 16.8 Hz, 6 H). | white solid |
| | | 4-[3-(3-adamantan-1-yl-4-methoxy-phenyl)-[1,2,4]oxadiazol-5-yl]-benzoic acid | B (Figure 2) | 1H NMR (400 MHz, DMSO): δ (ppm) 8.31 (d, J = 8.1 Hz, 2 H); 8.21 (d, J = 8.1 Hz, 2 H); 7.95-7.98 (m, 2 H); 7.18 (d, J = 8.5 Hz, 1 H); 3.89 (s, 3 H); 2.08 (s, 6 H); 2.03 (s, 3 H); 1.72 (s, 6 H). | white solid |
| | | 4-[3-(3-adamantan-1-yl-4-ethoxy-phenyl)-[1,2,4]oxadiazol-5-yl]-benzoic acid | B (Figure 2) | $^1$H NMR (400 MHz, DMSO): δ (ppm) 8.13-8.18 (m, 4 H); 7.90 (m, 2 H); 7.15-7.16 (m, 1 H); 4.14 (m, 2 H); 2.13 (s, 6 H); 2.07 (s, 3 H); 1.75 (s, 6 H); 1.44 (s, 3 H). | white solid |
| | | 4-[3-(3-adamantan-1-yl-4-propoxy-phenyl)-[1,2,4]oxadiazol-5-yl]-benzoic acid | B (Figure 2) | $^1$H NMR (400 MHz, DMSO): δ (ppm) 8.31 (m, 2 H); 8.25 (m, 2 H); 7.99 (m, 2 H); 7.13 (m, 1 H); 4.00 (m, 2 H); 2.11 (s, 8 H); 2.01 (s, 3 H); 1.79 (m, 2 H); 1.70 (s, 6 H); 1.05 (m, 3 H). | white solid |

-continued

| Example no. in experimental part | Chemical structure | Compound name | Synthesis pathway | 1H NMR | Appearance |
|---|---|---|---|---|---|
| | | 4-[3-(3-adamantan-1-yl-4-isobutoxy-phenyl)-[1,2,4]oxadiazol-5-yl]-benzoic acid | B (Figure 2) | $^1$H NMR (400 MHz, DMSO): δ (ppm) 8.30 (m, 2 H); 8.21 (m, J = 6.7 Hz, 2 H); 7.95 (m, 2 H); 7.15 (m, 1 H); 3.88 (m, 2 H); 2.14 (s, 8 H); 2.07 (s, 3 H); 1.75 (s, 6 H); 1.20 (m, 1H); 1.08 (m, 6 H). | white solid |
| | | 4-[3-[3-adamantan-1-yl-4-(2,2-dimethoxy-ethoxy)-phenyl]-[1,2,4]oxadiazol-5-yl]-benzoic acid | B (Figure 2) | $^1$H NMR (400 MHz, DMSO): δ (ppm) 8.30 (m, 4 H); 8.01-8.02 (m, 2 H); 7.20 (m, 2 H); 4.88 (t, J = 5.3 Hz, 1 H); 4.13 (d, J = 5.3 Hz, 2 H); 2.13 (s, 6 H); 2.01 (s, 3 H); 1.71 (t, J = 15.8 Hz, 6 H). An aromatic is masked by a pyridine signal (?). | light brown solid |
| | | 4-[3-(3-tert-butyl-4-ethoxymethoxy-phenyl)-[1,2,4]oxadiazol-5-yl]-benzoic acid | B (Figure 2) | $^1$H NMR (400 MHz, DMSO): δ (ppm) 8.29-8.32 (m, 4 H); 8.11 (d, J = 2.3 Hz, 1 H); 7.95 (dd, 8.5, 2.2 Hz, 1 H); 7.28 (d, J = 8.5 Hz, 1 H); 5.36 (s, 2 H); 3.78 (q, J = 7.0 Hz, 2 H); 1.47 (s, 9 H); 1.27 (t, J = 7.0 Hz, 3 H). | white solid |
| | | 4-(3-[4-ethoxymethoxy-3-(1-methyl-cyclohexyl)-phenyl]-[1,2,4]oxadiazol-5-yl)-benzoic acid | B (Figure 2) | $^1$H NMR (400 MHz, DMSO): δ (ppm) 8.35 (d, J = 8.2 Hz, 2 H); 8.29-8.30 (d, 2 H); 8.14 (d, J = 2.3 Hz, 1 H); 7.98 (dd, 8.5, 2.3 Hz, 1 H); 7.28 (s, 1 H); 5.34 (s, 2 H); 3.78 (q, J = 7.0 Hz, 2 H); 2.20 (m, 2 H); 1.82 (m, 2 H); 2.18 (m, 2 H); 1.55-1.88 (m, 5 H); 1.42 (m, 1 H); 1.27 (t, J = 7.0 Hz, 3 H). | white solid |

-continued

| Example no. in experimental part | Chemical structure | Compound name | Synthesis pathway | 1H NMR | Appearance |
|---|---|---|---|---|---|
| | | 4-{3-[4-hydroxy-3-(1-methyl-cyclohexyl)-phenyl]-[1,2,4]oxadiazol-5-yl}-benzoic acid | B (Figure 2) | ¹H NMR (400 MHz, DMSO): δ (ppm) 9.42 (s, 1 H); 8.19 (d, J = 8.1 Hz, 2 H); 8.12 (d, J = 8.1 Hz, 2 H); 7.83 (s, 1 H); 7.70 (d, J = 8.4 Hz, 1 H); 8.88 (d, J = 8.3 Hz, 1 H); 2.13 (m, 2 H); 1.09 (m, 2 H); 1.43 (m, 8 H); 1.33 (m, 1 H); 1.28 (s, 3 H). | white solid |
| | | 4-{3-[3-tert-butyl-4-(2-methoxy-ethoxy)-phenyl]-[1,2,4]oxadiazol-5-yl}-benzoic acid | B (Figure 2) | ¹H NMR (400 MHz, DMSO): δ (ppm) 8.20 (q, J = 8.2 Hz, 2 H); 8.13 (d, J = 8.0 Hz, 2 H); 7.98 (s, 1 H); 7.88 (d, J = 8.5 Hz, 1 H); 8.92 (d, J = 8.5 Hz, 1 H); 4.14 (s, 2 H); 3.75 (s, 2 H); 3.37 (s, 3H); 1.37 (s, 9 H). | pale pink solid |
| | | 4-{3-[3-tert-butyl-4-(2-dimethylamino-ethoxy)-phenyl]-[1,2,4]oxadiazol-5-yl}-benzoic acid | B (Figure 2) | ¹H NMR (400 MHz, DMSO): δ (ppm) 8.34 (q, 4 H); 8.18 (m, 2 H); 7.22 (m, 1 H); 4.18 (s, 2 H); 2.72 (s, 2 H); 2.23 (s, 6 H); 1.41 (s, 9 H). | broken white solid |
| | | 4-[3-(3-tert-butyl-4-methoxy-phenyl)-[1,2,4]oxadiazol-5-yl]-benzoic acid | B (Figure 2) | ¹H NMR (400 MHz, DMSO): δ (ppm) 8.20 (d, J = 8.7 Hz, 2 H); 8.13 (d, J = 9.7 Hz, 2 H); 7.97 (s, 1 H); 7.80 (d, J = 9.8 Hz, 1 H); 8.93 (d, J = 8.0 Hz, 1 H); 3.85 (s, 3 H); 1.35 (s, 9 H). | white solid |
| | | 4-[3-(3-tert-butyl-4-propoxy-phenyl)-[1,2,4]oxadiazol-5-yl]-benzoic acid | B (Figure 2) | ¹H NMR (400 MHz, DMSO): δ (ppm) 8.20 (d, J = 8.2 Hz, 2 H); 7.97 (s, 1 H); 7.80 (d, J = 8.5 Hz, 1 H); 8.91 (d, J = 8.5 Hz, 1 H); 3.82-4.00 (m, 2 H); 1.83 (m, 2 H); 1.38 (s, 8 H); 1.08 (t, J = 7.5 Hz, 3 H). | white solid |

-continued

| Example no. in experimental part | Chemical structure | Compound name | Synthesis pathway | 1H NMR | Appearance |
|---|---|---|---|---|---|
| | | 4-[3-(3-tert-butyl-4-isobutoxy-phenyl)-[1,2,4]oxadiazol-5-yl]-benzoic acid | B (Figure 2) | $^1$H NMR (400 MHz, DMSO): δ (ppm) 8.28 (d, J = 8.2 Hz, 2 H); 8.17 (d, J = 8.0 Hz, 2 H); 7.97 (s, 1 H); 7.92 (d, J = 8.8 Hz, 1 H); 7.12 (d, J = 8.8 Hz, 1 H); 3.88 (d, J = 8.2 Hz, 2 H); 2.15 (m, 1 H); 1.43 (s, 9 H); 1.08 (d, J = 8.7 Hz, 8 H). | beige solid |
| | | 4-[3-(3-tert-butyl-4-(2,2,2-trifluoro-ethoxy)-phenyl)-[1,2,4]oxadiazol-5-yl]-benzoic acid | B (Figure 2) | $^1$H NMR (400 MHz, DMSO): δ (ppm) 8.31 (d, J = 8.1 Hz, 2 H); 8.19 (d, J = 8.1 Hz, 2 H); 8.03 (d, J = 2.3 Hz, 1 H); 7.98 (dd, J = 8.8 et 2.3 Hz, 1 H); 7.26 (d, J = 8.7 Hz, 1 H); 4.92 (q, J = 8.8 Hz, 2 H); 1.42 (s, 9 H). | white solid |
| | | 4-[3-(3-tert-butyl-4-cyclopropylmethoxy-phenyl)-[1,2,4]oxadiazol-5-yl]-benzoic acid | B (Figure 2) | $^1$H NMR (400 MHz, DMSO): δ (ppm) 8.29 (d, J = 8.1 Hz, 2 H); 8.18 (d, J = 8.1 Hz, 2 H); 7.98 (s, 1 H); 7.82 (d, J = 8.8 Hz, 1 H); 7.13 (d, J = 8.8 Hz, 1 H); 3.87 (d, J = 7.0 Hz, 2 H); 1.45 (s, 8 H); 1.32 (s, 1 H); 0.83 (d, J = 7.8 Hz, 2 H); 0.38 (d, J = 5.1 Hz, 2 H). | white solid |
| | | 4-[3-[3-tert-butyl-4-(2,2-dimethoxy-ethoxy)-phenyl]-[1,2,4]oxadiazol-5-yl]-benzoic acid | B (Figure 2) | $^1$H NMR (400 MHz, DMSO): δ (ppm) 8.30 (s, 2 H); 8.19 (s, 2 H); 7.98 (m, 2 H); 7.21 (d, J = 8.5 Hz, 1 H); 4.82 (s, 1 H); 4.10 (s, 2 H); 3.39 (m, 8 H); 1.42 (s, 9 H). | pale pink solid |

-continued

| Example no. in experimental part | Chemical structure | Compound name | Synthesis pathway | 1H NMR | Appearance |
|---|---|---|---|---|---|
| | | 4-[3-[3-tert-butyl-4-([1,3]dioxolan-2-ylmethoxy)-phenyl]-[1,2,4]oxadiazol-5-yl]-benzoic acid | B (Figure 2) | $^1$H NMR (400 MHz, DMSO): δ (ppm) 8.30 (d, J = 8.2 Hz, 2 H); 8.18 (d, J = 8.2 Hz, 2 H); 7.88 (d, J = 2.2 Hz, 1 H); 7.93 (dd, J = 8.5, 2.1 Hz, 1 H); 7.19 (d, J = 8.6 Hz, 1 H); 8.32 (t, J = 3.8 Hz, 1 H); 4.14 (d, J = 3.8 Hz, 2 H); 3.85-3.98 (m, 4 H); 1.42 (s, 9 H). | white solid |
| | | 4-[3-[4-methoxy-3-(1-methyl-cyclohexyl)-phenyl]-[1,2,4]oxadiazol-5-yl]-benzoic acid | B (Figure 2) | $^1$H NMR (400 MHz, DMSO): δ (ppm) 8.27 (s, 2 H); 8.17 (s, 2H); 7.98 (s, 1 H); 7.83 (br s, 1 H); 7.18 (s, 1 H); 3.87 (s, 3 H); 2.08 (br s, 2 H); 1.73 (br s, 2 H); 1.46-1.56 (m, 6 H); 1.29 (s, 3 H). | white solid |
| | | 4-[3-[4-isobutoxy-3-(1-methyl-cyclohexyl)-phenyl]-[1,2,4]oxadiazol-5-yl]-benzoic acid | B (Figure 2) | $^1$H NMR (400 MHz, DMSO): δ (ppm) 8.27 (d, J = 8.0 Hz, 2H); 8.17 (d, J = 8.0 Hz, 2 H); 8.00 (s, 1H); 7.90 (d, J = 8.8 Hz, 1 H); 7.15 (d, J = 8.8 Hz, 1 H); 3.88 (d, J = 8.1 Hz, 2 H); 2.15 (br s, 2 H); 1.72 (br s, 2 H); 1.39-1.50 (m, 9 H); 1.08 (d, J = 8.7 Hz, 6 H). | white solid |
| | | 4-(3-[4-cyclopropylmethoxy-3-(1-methyl-cyclohexyl)-phenyl]-[1,2,4]oxadiazol-5-yl)-benzoic acid | B (Figure 2) | $^1$H NMR (400 MHz, DMSO): δ (ppm) 13.4 (br s, 1H); 8.28 (m, 2 H); 8.18 (m, 2 H); 7.99 (s, 1 H); 7.89 (d, J = 8.8 Hz, 1 H); 7.12 (d, J = 8.8 Hz, 1 H); 3.94 (d, J = 7.0 Hz, 2 H); 2.20 (m, 2 H); 1.57 (m, 2 H); 1.48-1.57 (m, 8 H); 1.35 (m, 4 H); 0.80 (s, 2 H); 0.35 (s, 2 H). | white solid |

| Example no. in experimental part | Chemical structure | Compound name | Synthesis pathway | 1H NMR | Appearance |
|---|---|---|---|---|---|
| | | 4-[3-[3-(1-methyl-cyclohexyl)-4-(2,2,2-trifluoro-ethoxy)-phenyl]-[1,2,4]oxadiazol-5-yl]-benzoic acid | B (Figure 2) | ¹H NMR (400 MHz, DMSO): δ (ppm) 8.24 (d, J = 7.9 Hz, 2 H); 8.15 (d, J = 8.0 Hz, 2 H); 8.08 (d, 2.1 Hz, 1 H); 7.97 (dd, J = 8.8, 2.1 Hz, 1 H); 7.26 (d, J = 8.6 Hz, 1 H); 4.90 (q, J = 8.7 Hz, 2 H); 2.14 (m, 2 H); 1.72 (m, 2 H); 1.52 (m, 6 H); 1.33 (s, 3 H). | white solid |
| | | 4-[3-[4-([1,3]dioxolan-2-ylmethoxy)-3-(1-methyl-cyclohexyl)-phenyl]-[1,2,4]oxadiazol-5-yl]-benzoic acid | B (Figure 2) | | |
| | | 4-[3-[3-tert-Butyl-4-(2-hydroxy-ethoxy)-phenyl]-[1,2,4]oxadiazol-5-yl]-benzoic acid | B (Figure 2) | | |
| | | 4-[3-[3-tert-Butyl-4-(3-hydroxy-propoxy)-phenyl]-[1,2,4]oxadiazol-5-yl]-benzoic acid | B (Figure 2) | | |

-continued

| Example no. in experimental part | Chemical structure | Compound name | Synthesis pathway | 1H NMR | Appearance |
|---|---|---|---|---|---|
| | | methyl 4-[3-[3-tert-butyl-4-hydroxy-phenyl]-[1,2,4]oxadiazol-5-yl]-benzoate | B (Figure 2) | | |
| | | 4-[3-[3-tert-butyl-4-((E)-propenyl)-phenyl]-[1,2,4]oxadiazol-5-yl]-benzoic acid | B (Figure 2) | | |
| | | 4-[3-(3-tert-butyl-4-propyl-phenyl)-[1,2,4]oxadiazol-5-yl]-benzoic acid | B (Figure 2) | | |
| | | 4-[3-(4-cyclopropylmethoxy-3-pyrrolidin-1-yl-phenyl)-[1,2,4]oxadiazol-5-yl]-benzoic acid | B (Figure 2) | | |

-continued

| Example no. in experimental part | Chemical structure | Compound name | Synthesis pathway | 1H NMR | Appearance |
|---|---|---|---|---|---|
| | | 4-[3-(4-hydroxy-3-pyrrolidin-1-yl-phenyl)-[1,2,4]oxadiazol-5-yl]-benzoic acid | B (Figure 2) | | |
| | | 4-[3-[4-(2-hydroxy-ethoxy)-3-pyrrolidin-1-yl-phenyl]-[1,2,4]oxadiazol-5-yl]-benzoic acid | B (Figure 2) | | |
| | | 4-[3-(4-Cyclopropylmethoxy-3-pyrrolidin-1-yl-phenyl]-[1,2,4]oxadiazol-5-yl]-benzoic acid | B (Figure 2) | | |
| | | 4-[3-(4-Hydroxy-3-pyrrolidin-1-yl-phenyl)-[1,2,4]oxadiazol-5-yl]-benzoic acid | B (Figure 2) | | |

-continued

| Example no. in experimental part | Chemical structure | Compound name | Synthesis pathway | 1H NMR | Appearance |
|---|---|---|---|---|---|
| | | 4-{3-[4-(2-hydroxy-ethoxy)-3-pyrrolidin-1-yl-phenyl)-[1,2,4]oxadiazol-5-yl}-benzoic acid | B (Figure 2) | | |
| | | 4-[3-(4-diethylamino-3-(3-hydroxy-propoxy-phenyl)-[1,2,4]oxadiazol-5-yl]-benzoic acid | B (Figure 2) | | |
| | | 4-[3-(4-tert-butyl-3-ethylamino-phenyl)-[1,2,4]oxadiazol-5-yl]-benzoic acid | B (Figure 2) | | |
| | | 4-[3-(3-adamantan-1-yl-4-trimethyl-silanylmethoxy-phenyl)-[1,2,4]oxadiazol-5-yl]-benzoic acid | B (Figure 2) | | |

| Example no. in experimental part | Chemical structure | Compound name | Synthesis pathway | 1H NMR | Appearance |
|---|---|---|---|---|---|
| | (structure shown) | 4-[3-(4-tert-butyl-3-ethylamino-phenyl)-[1,2,4]oxadiazol-5-yl]-benzoic acid | B (Figure 2) | | |

C: Preparation of the Pyrazole Compounds Described in Figure 3

Example 6: 4-[5-(3-adamantan-1-yl-4-hydroxy-phenyl)-4H-pyrazol-3-yl]-benzoic acid

6.1: methyl 3-adamantan-1-yl-4-(2-methoxy-ethoxymethoxy)-benzoate 1.7 g (42 mmol) of 60% sodium hydride in hexane are added to a solution of 10 g (35 mmol) of methyl 3-adamantan-1-yl-4-hydroxy-benzoate (prepared as described in Example 1.1) in 50 ml of tetrahydrofuran and 50 ml of dimethylformamide, previously cooled to 0° C. The reaction is stirred for 20 minutes then 4.4 ml (38 mmol) of 1-chloromethoxy-2-methoxy-ethane are added dropwise. The reaction medium is stirred from 0° C. to room temperature for 2 hours. Water is added and the reaction medium is extracted with ethyl acetate. The organic phase is dried on magnesium sulfate, filtered and evaporated. 14.8 g of crude residue are obtained and purified by silica gel chromatography eluted with a 7/3 heptane/ethyl acetate mixture. 12.8 g (99%) of methyl 3-adamantan-1-yl-4-(2-methoxy-ethoxymethoxy)-benzoate are obtained.

6.2: 3-adamantan-1-yl-4-(2-methoxy-ethoxymethoxy)-benzoic acid 2.8 g (69 mmol) of sodium hydroxide are added to a solution of 12.8 g (34 mmol) of methyl 3-adamantan-1-yl-4-(2-methoxy-ethoxymethoxy)-benzoate in 90 ml of tetrahydrofuran, 30 ml of methanol and 1 ml of water. The reaction medium is heated under reflux for 8 hours. After addition of water, the reaction medium is acidified to pH 6 and then extracted with ethyl acetate. The organic phase is washed with water, dried on magnesium sulfate, filtered and evaporated. 12.4 g (97%) of 3-adamantan-1-yl-4-(2-methoxy-ethoxymethoxy)-benzoic acid are obtained.

6.3: 1-[3-adamantan-1-yl-4-(2-methoxy-ethoxymethoxy)-phenyl]-ethanone 101 ml (101 mmol) of a methyllithium solution in 1 M tetrahydrofuran are added dropwise to a solution, previously cooled to −78° C., of 12.1 g (34 mmol) of 3-adamantan-1-yl-4-(2-methoxy-ethoxymethoxy)-benzoic acid in 90 ml of tetrahydrofuran and 90 ml of diethyl ether. The reaction medium is stirred from −78° C. to room temperature for 18 hours. 9 ml (75 mmol) of trimethylsilyl chloride are added and the reaction medium is stirred again for 45 minutes. 100 ml of water followed by 100 ml of a 1 M aqueous hydrochloric acid solution are added then the reaction medium is extracted with diethyl ether. The organic phase is washed with water, dried on magnesium sulfate, filtered and evaporated. 19 g of crude residue are obtained and purified by silica gel chromatography and eluted with a 6/4 heptane/ethyl acetate mixture. 12 g (98%) 1-[3-adamantan-1-yl-4-(2-methoxy-ethoxymethoxy)-phenyl]-ethanone are obtained.

6.4: methyl 4-{3-[3-adamantan-1-yl-4-(2-methoxy-ethoxymethoxy)-phenyl]-3-oxo-propionyl}-benzoate 65 ml (130 mmol) of a commercial solution of lithium diisopropylamide in 2 M tetrahydrofuran are added dropwise to a solution, previously cooled to −78° C., of 12 g (33 mmol) of 1-[3-adamantan-1-yl-4-(2-methoxy-ethoxymethoxy)-phenyl]ethanone in 90 ml of tetrahydrofuran. After stirring at −78° C. for 1 hour, a solution of 7.2 g (36 mmol) of methyl 4-chlorocarbonyl-benzoate in 70 ml of dioxane is added dropwise. The reaction medium is stirred from −78° C. to room temperature for 18 hours. After addition of water and neutralization to pH 5-6 by addition of a 1 M aqueous hydrochloric acid solution, the reaction medium is extracted with ethyl acetate. The organic phase is washed with water, dried on magnesium sulfate and then filtered and evaporated. 20.5 g of crude residue are obtained and purified by silica gel chromatography, eluted with a 99/1 dichloromethane/ethyl acetate mixture. 5 g (29%) of methyl 4-{3-[3-adamantan-1-yl-4-(2-methoxy-ethoxymethoxy)-phenyl]-3-oxo-propionyl}-benzoate are obtained.

6.5: methyl 4-{5-[3-adamantan-1-yl-4-(2-methoxy-ethoxymethoxy)-phenyl]-4H-pyrazol-3-yl}-benzoate 0.5 ml (10.4 mmol) of hydrazine hydrate are added to a solution of 2.7 g (5.2 mmol) of methyl 4-{3-[3-adamantan-1-yl-4-(2-methoxy-ethoxymethoxy)-phenyl]-3-oxo-propionyl}-benzoate in 35 ml of methanol. The reaction medium is stirred at room temperature for 18 hours. After addition of water, the reaction medium is extracted with ethyl acetate. The organic phase is washed with water, dried on magnesium sulfate and then filtered and evaporated. The residue obtained is recrystallized in a heptane/diethyl ether mixture (1/1). 2.7 g (75%) of methyl 4-{5-[3-adamantan-1-yl-4-(2-methoxy-ethoxymethoxy)-phenyl]-4H-pyrazol-3-yl}-benzoate are obtained in the form of a pale yellow solid.

6.6: ethyl 3-[3-adamantan-1-yl-4-(2-methoxy-ethoxymethoxy)-phenyl]-5-(4-methoxycarbonyl-phenyl)-pyrazole-1-carboxylate 0.2 ml (1.4 mmol) of triethylamine then 0.2 ml (1.8 mmol) of ethyl chloroformate are added to a solution of 0.3 g (0.6 mmol) of methyl 4-{5-[3-adamantan-1-yl-4-(2-methoxy-ethoxymethoxy)-phenyl]-4H-pyrazol-3-yl}-benzoate. The reaction medium is stirred at room temperature for 18 hours. After addition of water, the reaction medium is extracted with dichloromethane. The organic phase is dried on magnesium sulfate then filtered and evaporated. 0.5 g of crude residue are obtained and purified by silica gel chromatography eluted with an 8/2 heptane/ethyl acetate mixture. 0.3 g (88%) of ethyl 3-[3-adamantan-1-yl-4-(2-methoxy-ethoxymethoxy)-phenyl]-5-(4-methoxycarbonyl-phenyl)-pyrazole-1-carboxylate are obtained.

6.7: ethyl 3-(3-adamantan-1-yl-4-hydroxy-phenyl)-5-(4-methoxycarbonyl-phenyl)-pyrazole-1-carboxylate 0.3 g (0.5 mmol) of ethyl 3-[3-adamantan-1-yl-4-(2-methoxy-ethoxymethoxy)-phenyl]-5-(4-methoxycarbonyl-phenyl)-pyrazole-1-carboxylate are placed in solution in 3 ml of methanol, 10 ml of tetrahydrofuran and 0.3 ml concentrated sulfuric acid then stirred at room temperature for 48 hours. Water is added and the reaction medium is extracted with ethyl acetate. The organic phase is dried on magnesium sulfate then filtered and evaporated. 264 mg (100%) of ethyl 3-(3-adamantan-1-yl-4-hydroxy-phenyl)-5-(4-methoxycarbonyl-phenyl)-pyrazole-1-carboxylate are obtained.

6.8: 4-[5-(3-adamantan-1-yl-4-hydroxy-phenyl)-2H-pyrazol-3-yl]-benzoic acid 0.8 ml (0.8 mmol) of a 1 M aqueous sodium hydroxide solution are added to a solution of 130 mg (0.3 mmol) of ethyl 3-(3-adamantan-1-yl-4-hydroxy-phenyl)-5-(4-methoxycarbonyl-phenyl)-pyrazole-1-carboxylate in 5 ml of tetrahydrofuran and 0.5 ml of water. The reaction medium is stirred at room temperature for 4 hours. After addition of water and acidification with a 1 M solution of hydrochloric acid to pH 4-5, the precipitate formed is filtered, washed with water and dried. 130 mg of crude residue are obtained and purified by silica gel chromatography eluted with a 1/1 heptane/ethyl acetate mixture. 80 mg (74%) of 4-[5-(3-adamantan-1-yl-4-hydroxy-phenyl)-2H-pyrazol-3-yl]-benzoic acid are obtained.

Example 7: 4-{5-[3-adamantan-1-yl-4-(2-methoxy-ethoxymethoxy)-phenyl]-4H-pyrazol-3-yl}-benzoic acid 0.7 ml (0.7 mmol) of a 1 M aqueous sodium hydroxide solution are added to a solution of 130 mg (0.2 mmol) of ethyl 3-[3-adamantan-1-yl-4-(2-methoxy-ethoxymethoxy)-phenyl]-5-(4-methoxycarbonyl-phenyl)-pyrazole-1-carboxylate (prepared as described in 6.6) in 7 ml of tetrahydrofuran and 0.5 ml of water. The reaction mixture is heated at 60° C. for 17 h. After cooling and acidification to pH 3 with a 1 M aqueous hydrochloric acid solution, the reaction medium is filtered. The precipitate is washed with water and dried under vacuum. 93 mg (84%) of 4-{5-[3-adamantan-1-yl-4-(2-methoxy-ethoxymethoxy)-phenyl]-4H-pyrazol-3-yl}-benzoic acid are obtained in the form of a white solid.

| Example no. in experimental part | Chemical structure | Compound name | Synthesis pathway | 1H NMR | Appearance |
|---|---|---|---|---|---|
| Example 6 | 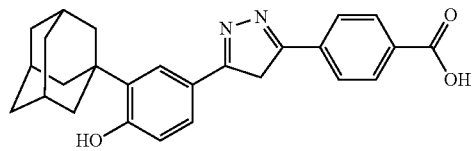 [SMILES: O=C(O)c1ccc(C2=NN=C(c3ccc(O)c(C45CC6CC(CC(C6)C4)C5)c3)C2)cc1] | 4-[5-(3-adamantan-1-yl-4-hydroxy-pheny)-4H-pyrazol-3-yl]-benzoic acid | C Figure 3) | ¹H NMR (400 MHz, CDCl₃): δ (ppm) 7.78 (d, J = 7.9 Hz, 2 H); 7.82 (d, J = 8.0 Hz, 2 H); 7.13 (d, J = 8.1 Hz, 1 H); 8.58 (d, J = 8.1 Hz, 1 H); 8.50 (s, 1 H); 1.91 (s, 8 H); 1.81 (s, 3 H); 1.51 (s, 6 H). | yellow solid |
| Example 7 | 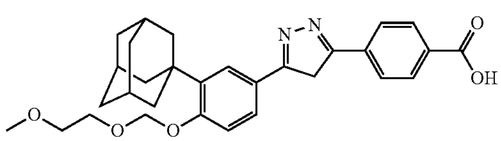 [SMILES: COCCOCOc1ccc(C2=NN=C(c3ccc(C(=O)O)cc3)C2)cc1C12CC3CC(CC(C3)C1)C2] | 4-[5-[3-adamantan-1-yl-4-(2-methoxy-ethoxymethoxy)-pheny]-4H-pyrazol-3-yl]-benzoic acid | C (Figure 3) | ¹H NMR (400 MHz, CDCl₃): δ (ppm) 7.91 (d, J = 8.0 Hz, 2 H); 7.74 (d, J = 8.1 Hz, 2 H); 7.48 (s, 1H); 7.39 (d, J = 8.6 Hz, 1 H); 7.03 (d, J = 8.5 Hz, 1 H); 8.87 (s, 1 H); 5.18 (s, 2 H); 3.70 (s, 3 H); 1.99 (s, 8 H); 1.93 (s, 4 H); 1.82 (s, 6 H). | yellow solid |

| Example no. in experimental part | Chemical structure | Compound name | Synthesis pathway | 1H NMR | Appearance |
|---|---|---|---|---|---|
| | | 3-[5-(3-adamantan-1-yl-4-hydroxy-pheny)-2-ethyl-2H-pyrazol-3-yl]-benzoic acid | C (Figure 3) | | |

D: Preparation of the Isoxazole Compounds Described in Figure 4

Example 8: 4-[3-(3-adamantan-1-yl-4-hydroxy-phenyl)-isoxazol-5-yl]-benzoic acid 8.1: methyl 4-[3-(3-adamantan-1-yl-4-hydroxy-phenyl)-isoxazol-5-yl]-benzoate A solution of 2.1 g (4 mmol) of ethyl 3-[3-adamantan-1-yl-4-(2-methoxy-ethoxymethoxy)-phenyl]-5-(4-methoxy-carbonyl-phenyl)-pyrazole-1-carboxylate (prepared as described in 6.6) in 50 ml of ethanol is added to a solution of 0.7 g (10 mmol) of hydroxylamine hydrochloride in 20 ml of water. The reaction medium is heated under reflux for 18 hours. After cooling, the precipitate formed is filtered and then dried under vacuum. 1.5 g (48%) of methyl 4-[3-(3-adamantan-1-yl-4-hydroxy-phenyl)-isoxazol-5-yl]-benzoate are obtained.

8.2: 4-[3-(3-adamantan-1-yl-4-hydroxy-phenyl)-isoxazol-5-yl]benzoic acid

500 µl (0.5 mmol) of a 1 M aqueous sodium hydroxide solution are added to a solution of 140 mg (0.3 mmol) of methyl 4-[3-(3-adamantan-1-yl-4-hydroxy-phenyl)-isoxazol-5-yl]-benzoate in 10 ml of tetrahydrofuran and 1 ml water. After stirring at room temperature for 18 hours, water is added then the medium is acidified with a 1 M aqueous hydrochloric acid solution. The precipitate formed is filtered and then dried under vacuum. The residue obtained is purified on silica gel eluted with a 50/50 heptane/ethyl acetate solution. 80 mg (60%) of 4-[3-(3-adamantan-1-yl-4-hydroxy-phenyl)-isoxazol-5-yl]-benzoic acid are obtained in the form of a white solid.

Example 9: 4-[3-(3-adamantan-1-yl-4-propoxy-phenyl)-isoxazol-5-yl]-benzoic acid 9.1: methyl 4-[3-(3-adamantan-1-yl-4-propoxy-phenyl)-isoxazol-5-yl]-benzoate 170 mg (0.9 mmol) of cesium carbonate are added to a solution of 320 mg (0.7 mmol) of methyl 4-[3-(3-adamantan-1-yl-4-hydroxy-phenyl)-isoxazol-5-yl]-benzoate (prepared as described in 8.1), 60 µl (0.9 mmol) of propyl iodide in 7 ml of dimethylformamide. The reaction mixture is heated at 80° C. for 18 h, cooled and then filtered. After evaporation of the filtrate until dry, the crude residue obtained is purified by silica gel chromatography eluted with a 50/50 heptane/ethyl acetate mixture. 140 mg (42%) of methyl 4-[3-(3-adamantan-1-yl-4-propoxy-phenyl)-isoxazol-5-yl]-benzoate are obtained in the form of a white solid.

9.2: 4-[3-(3-adamantan-1-yl-4-propoxy-phenyl)-isoxazol-5-yl]benzoic acid

500 µl (0.5 mmol) of a 1 M aqueous sodium hydroxide solution are added to a solution of 140 mg (0.3 mmol) of methyl 4-[3-(3-adamantan-1-yl-4-propoxy-phenyl)-isoxazol-5-yl]-benzoate in a mixture of 7 ml of tetrahydrofuran and 2 ml water. After stirring at room temperature for 18 hours, the tetrahydrofuran is evaporated until dry and then the reaction medium is acidified to pH 2-3 by addition of a 1 M aqueous hydrochloric acid solution. The product formed precipitates and is filtered and rinsed with methanol. 130 mg (94%) of 4-[3-(3-adamantan-1-yl-4-propoxy-phenyl)-isoxazol-5-yl]-benzoic acid are obtained

| no example dans parte experimentale | Chemical structure | Compound name | Synthesis pathway | 1H NMR | Appearance |
|---|---|---|---|---|---|
| Example 8 | 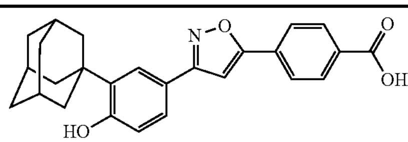 | 4-[3-(3-adamantan-1-yl-4-hydroxy-phenyl)-isoxazol-5-yl]-benzoic acid | D (Figure 4) | $^1$H NMR (400 MHz, CDCl$_3$): δ (ppm) 8.01 (s, 1 H); 8.02 (d, J = 7.9 Hz, 2 H); 7.81 (d, J = 8.2 Hz, 2 H); 7.51 (s, 1 H); 7.39 (d, J = 8.3 Hz, 1 H); 8.79 (d, J = 8.4 Hz, 1 H); 6.61 (s, 1 H); 2.08 (s, 6 H); 1.97 (s, 3 H); 1.67 (s, 6 H). | white solid |

-continued

| no example dans parte experimentale | Chemical structure | Compound name | Synthesis pathway | 1H NMR | Appearance |
|---|---|---|---|---|---|
| Example 9 | 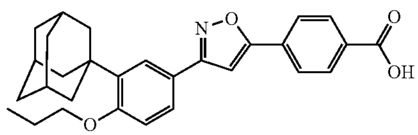 [SMILES: CCCOc1ccc(-c2cc(-c3ccc(C(=O)O)cc3)on2)cc1C12CC3CC(CC(C3)C1)C2] | 4-[3-(3-adamantan-1-yl-4-propoxy-phenyl)-isoxazol-5-yl]-benzoic acid | D (Figure 4) | ¹H NMR (400 MHz, DMSO): δ (ppm) 8.06-8.09 (m, 4 H); 7.70-7.74 (m, 2 H); 7.59 (s, 1 H); 7.14 (d, J = 8.8 Hz, 1 H); 4.05 (t, J = 6.3 Hz, 2 H); 2.15 (s, 6 H); 2.09 (s, 3H); 1.85 (m, 2 H); 1.77 (s, 6 H); 1.11 (t, J = 7.3 Hz, 3 H). | white solid |
| | | 4-[3-(3-adamantan-1-yl-4-cyclopropylmethoxy-phenyl)-isoxazol-5-yl]-benzoic acid | D (Figure 4) | ¹H NMR (400 MHz, DMSO): δ (ppm) 8.07 (d, J = 8.0 Hz, 2 H); 8.00 (d, J = 8.2 Hz, 2 H); 7.68-7.72 (m, 2 H); 7.57 (s, 0.6 H); 7.09 (d, J = 8.9 Hz, 2 H); 2.17 (s, 6 H); 2.09 (s, 3 H); 1.77 (s, 6 H); 1.17 (m, 1 H); 0.83 (d, J = 7.7 Hz, 2 H); 0.39 (d, J = 5.1 Hz, 2 H). | white solid |
| | | 4-[3-(3-adamantan-1-yl-4-methoxy-phenyl)-isoxazol-5-yl]-benzoic acid | D (Figure 4) | ¹H NMR (400 MHz, DMSO): δ (ppm) 8.08 (m, 4 H); 7.64-7.73 (m, 3 H); 7.17 (d, J = 8.9 Hz, 1 H); 3.89 (s, 3 H); 2.11 (br s, 9 H); 1.77 (s, 6 H). | white solid |
| | | 4-[3-(3-adamantan-1-yl-4-isobutoxy-phenyl)-isoxazol-5-yl]-benzoic acid | D (Figure 4) | ¹H NMR (400 MHz, DMSO): δ (ppm) 8.08 (d, J = 7.9 Hz, 2 H); 7.92 (d, J = 8.7 Hz, 2 H); 7.83 (s, 2 H); 7.15 (s, 1 H); 8.98 (d, J = 8.7 Hz, 1 H); 3.81 (s, 2 H); 2.18 (s, 1 H); 2.13 (s, 6 H); 2.07 (s, 3 H); 1.75 (s, 6 H); 1.09 (d, J = 8.6 Hz, 6 H) | white solid |
| | | 4-{3-[3-adamantan-1-yl-4-(2,2-dimethoxy-ethoxy)-phenyl]-isoxazol-5-yl}-benzoic acid | D (Figure 4) | ¹H NMR (400 MHz, DMSO): δ (ppm) 8.05-8.08 (m, 4 H); 7.70-7.74 (m, 3 H); 7.61 (s, 1 H); 7.17 (d, J = 8.9 Hz, 1 H); 4.83 (t, J = 5.2 Hz, 1 H); 4.08 (d, J = 5.3 Hz, 2 H); 3.40 (s, 6 H); 2.11 (m, 12 H); 1.77 (s, 6 H). | white solid |
| | | 4-[3-(3-adamantan-1-yl-4-ethoxy-phenyl)-isoxazol-5-yl]-benzoic | D (Figure 4) | | |

| no example dans parte experimentale | Chemical structure | Compound name | Synthesis pathway | 1H NMR | Appearance |
|---|---|---|---|---|---|
|  |  | 4-[3-(3-diethylamino-3-propoxy-phenyl)-isoxazol-5-yl]-benzoic acid |  |  |  |

E: Preparation of the Thiazole Compounds Described in Figure 5

Example 10: 4-[5-(3-adamantan-1-yl-4-ethoxymethoxy-phenyl)-thiazol-2-yl]-benzoic acid 10.1: 1-(5-bromo-2-ethoxymethoxy-phenyl)-adamantane 4.7 g (120 mmol) of 60% sodium hydride in hexane are added portionwise to a solution, previously cooled to 0° C., of 30 g (100 mmol) of 2-adamantan-1-yl-4-bromo-phenol in a mixture of 300 ml of dimethylformamide and 300 ml of tetrahydrofuran. After stirring at 0° C. for 30 minutes, 10.6 ml (120 mmol) of chloromethoxy-ethane are added dropwise. The reaction medium is stirred from 0° C. to room temperature for 4 hours. After addition of water, the reaction medium is extracted with ethyl acetate. The organic phase is washed abundantly with water, dried on magnesium sulfate, filtered and evaporated. 35 g (95%) of 1-(5-bromo-2-ethoxymethoxy-phenyl)-adamantane.

10.2: 3-(adamantan-1-yl)-4-ethoxymethoxy-phenyl-boronic acid 28 ml (70 mmol) of a 2.5 M butyllithium solution in hexane are added dropwise to a solution, previously cooled to −78° C., of 21 g (60 mmol) of 1-(5-bromo-2-ethoxymethoxy-phenyl)-adamantane in 210 ml of tetrahydrofuran. After stirring for 1 hour at −78° C., 15 ml (60 mmol) of tri-isopropyl-borate are added. The reaction medium is stirred 1 hour at −78° C. then room temperature for 5 hours. After cooling to 0° C., 80 ml (80 mmol) of a 1 M aqueous hydrochloric acid solution are added, the medium is stirred for 30 minutes and extracted with ethyl acetate. The organic phase is washed with a saturated sodium chloride solution, dried on magnesium sulfate, filtered and then evaporated. The residue obtained is taken up in heptane and then the precipitate is filtered. 13.4 g (73%) of 3-(adamantan-1-yl)-4-ethoxymethoxy-phenyl-boronic acid are obtained.

10.3: ethyl 4-thiazol-2-yl-benzoate 31 ml (20 mmol) of trimethylsilyl iodide and then a solution of 30 g (200 mmol) of 2-bromothiazole in 75 ml of tetrahydrofuran were added to a suspension of 36 g (550 mmol) of zinc powder in 90 ml of tetrahydrofuran previously activated by 4.5 ml (150 mmol) of 1,2-dibromoethane. The reaction medium is stirred for 15 minutes, then a solution of 46 ml (300 mmol) of ethyl 4-iodobenzoate in 375 ml of tetrahydrofuran and finally 2.7 g of tetrakis(triphenylphosphine)palladium are added. The reaction mixture is then heated at 60° C. for 18 hours. After cooling and filtration on celite, the filtrate is evaporated to dryness. 156 g of crude residue are obtained and purified by silica gel chromatography eluted with a 9/1 heptane/ethyl acetate mixture. 37 g (93%) of ethyl 4-thiazol-2-yl-benzoate are obtained.

10.4: ethyl 4-(5-bromo-thiazol-2-yl)-benzoate

A solution of 11 ml (200 mmol) of bromine in 95 ml of chloroform is added dropwise to a solution of 37 g (160 mmol) of ethyl 4-thiazol-2-yl-benzoate in 400 ml of chloroform, previously cooled to 0° C. The reaction medium is then stirred from 0° C. to room temperature for 24 hours. After addition of water and extraction with dichloromethane, the organic phase is dried on sodium sulfate, filtered and evaporated. 59.6 g of crude residue are obtained and purified by silica gel chromatography eluted with a 9/1 heptane/ethyl acetate mixture. 16.3 g (31%) of ethyl 4-(5-bromo-thiazol-2-yl)-benzoate are obtained in the form of a pale pink solid.

10.5: ethyl 4-[5-(3-adamantan-1-yl-4-ethoxymethoxy-phenyl)-thiazol-2-yl]-benzoate 20 ml (40 mmol) of a 2 M aqueous solution of potassium carbonate are added dropwise to a mixture of 5 g (16 mmol) of ethyl 4-(5-bromo-thiazol-2-yl)-benzoate and 7 g (21 mmol) of 3-(adamantan-1-yl)-4-ethoxymethoxy-phenyl-boronic acid in 50 ml of dimethoxyethane. The reaction medium is then degassed under nitrogen and then 0.9 g (0.8 mmol) of tetrakis(triphenylphosphine)palladium are added and the reaction medium is heated at 100° C. for 4 hours. After cooling and addition of water, the medium is extracted with dichloromethane, dried on sodium sulfate, filtered and evaporated. 13.4 g of crude residue are obtained and purified by silica gel chromatography eluted with a 95/5 heptane/ethyl acetate mixture. 7.5 g (87%) of ethyl 4-[5-(3-adamantan-1-yl-4-ethoxymethoxy-phenyl)-thiazol-2-yl]-benzoate are obtained.

10.6: 4-[5-(3-adamantan-1-yl-4-ethoxymethoxy-phenyl)-thiazol-2-yl]-benzoic acid 58 mg (1.4 mmol) of sodium hydroxide powder are added to a solution of 500 mg (1 mmol) of ethyl 4-[5-(3-adamantan-1-yl-4-ethoxymethoxy-phenyl)-thiazol-2-yl]-benzoate in 25 ml of tetrahydrofuran, 2.5 ml of methanol and 0.5 ml of water. The reaction medium is stirred at room temperature for 4 hours then water is added and the medium is acidified to pH 3 to with a 1 M aqueous hydrochloric acid solution and extracted with ethyl acetate. The organic phase is dried on magnesium sulfate then filtered and evaporated. 430 mg of crude residue are obtained and recrystallized in toluene. 240 mg (51%) 4-[5-(3-adamantan-1-yl-4-ethoxymethoxy-phenyl)-thiazol-2-yl]-benzoic acid are obtained.

Example 11: 4-[5-(3-adamantan-1-yl-4-isobutoxy-phenyl)-thiazol-2-yl]-benzoic acid 11.1: ethyl 4-[5-(3-adamantan-1-yl-4-hydroxy-phenyl)-thiazol-2-yl]benzoate 0.7 ml of concentrated sulfuric acid are added to a solution of 7 g (13.5 mmol) of ethyl 4-[5-(3-adamantan-1-yl-4-ethoxymethoxy-phenyl)-thiazol-2-yl] benzoate (prepared as described in Example 10.5) in 35 ml of tetrahydrofuran and 35 ml of ethanol. The reaction medium is stirred for 4 hours at room temperature and then 8 hours under reflux. After cooling, water is added and the reaction medium is extracted with ethyl acetate. The organic phase is dried on sodium sulfate then filtered and evaporated. 7.8 g (100%) of ethyl 4-[5-(3-adamantan-1-yl-4-hydroxy-phenyl)-thiazol-2-yl]benzoate are obtained.

11.2: ethyl 4-[5-(3-adamantan-1-yl-4-isobutoxy-phenyl)-thiazol-2-yl]-benzoate

A mixture of 100 mg (0.2 mmol) of ethyl 4-[5-(3-adamantan-1-yl-4-hydroxy-phenyl)-thiazol-2-yl]-benzoate, 36 mg (0.3 mmol) of 1-bromo-2-methylpropane, 13.4 mg (0.2 mmol) of potassium hydroxide in 2 ml of diglyme is heated under reflux for 5 hours. After cooling and dilution with water, the reaction medium is extracted with ethyl acetate. The organic phase is dried on magnesium sulfate then filtered and evaporated. The crude residue obtained is purified by silica gel chromatography eluted with a 9/1 heptane/ethyl acetate mixture. 104 mg (93%) of ethyl 4-[5-(3-adamantan-1-yl-4-isobutoxy-phenyl)-thiazol-2-yl]-benzoate are obtained.

11.3: 4-[5-(3-adamantan-1-yl-4-isobutoxy-phenyl)-thiazol-2-yl]-benzoic acid

According to a protocol identical to that of Example 10.6, from 104 mg (0.2 mmol), 95 mg (97%) of 4-[5-(3-adamantan-1-yl-4-isobutoxy-phenyl)-thiazol-2-yl]-benzoic acid are obtained in the form of a white solid.

Example 12: 4-[5-(3-tert-butyl-4-methoxy-phenyl)-thiazol-2-yl]-benzoic acid 12.1: 2-tert-butyl-4-iodo-phenol 16.5 g (73 mmol) of N-iodosuccinimide are added portionwise to a solution previously cooled to 0° C., of 10 g (67 mmol) of 2-tertbutylphenol and 1.5 ml (20 mmol) of trifluoroacetic acid in 250 ml of acetonitrile. After stirring at room temperature for 18 hours, ethyl acetate is added and the reaction medium is washed with a saturated aqueous sodium chloride solution then with a sodium thiosulfate solution. The organic phase is dried on magnesium sulfate then filtered and evaporated. The crude residue is purified by silica gel chromatography eluted with a 95/5 heptane/ethyl acetate mixture. 7.5 g (37%) of 2-tert-butyl-4-iodo-phenol are obtained.

12.2: 2-tert-butyl-4-iodo-1-(2-methoxy-ethoxymethoxy)-benzene 1.3 g (33 mmol) of 60% sodium hydride in hexane are added portionwise to a solution, previously cooled to 0° C., of 7.5 g (27 mmol) of 2-tert-butyl-4-iodo-phenol, 65 ml of tetrahydrofuran and 65 ml of dimethylformamide. After stirring at 0° C. for 30 minutes, 3.7 ml (33 mmol) of 1-chloromethoxy-2-methoxy-ethane are added dropwise. The reaction medium is stirred at room temperature for 1 hour and then poured into ice and extracted with ethyl acetate. The organic phase is washed with a saturated sodium chloride solution, dried on magnesium sulfate, filtered and evaporated. 13.6 g of crude residue are obtained and purified by silica gel chromatography eluted with heptane. 7.3 g (74%) of 2-tert-butyl-4-iodo-1-(2-methoxy-ethoxymethoxy)-benzene are obtained.

12.3: 3-tert-butyl-4-(2-methoxy-ethoxymethoxy)-benzene boronic acid 9.5 ml (24 mmol) of a solution of butyl lithium in 2.5 M hexane are added to a solution, previously cooled to −78° C., of 7.2 g (20 mmol) of 2-tert-butyl-4-iodo-1-(2-methoxy-ethoxymethoxy)-benzene in 72 ml of tetrahydrofuran. After stirring at −78° C. for 1 hour, 5 ml (22 mmol) of tri-isopropylborate are added dropwise. The reaction medium is stirred from −78° C. to room temperature for 2 hours. The reaction medium is again cooled to 0° C. and then a saturated aqueous ammonium chloride solution is added and the medium is stirred for 1 hour and then extracted with ethyl acetate. The organic phase is dried on sodium sulfate then filtered and evaporated. 5.5 g (100%) of 3-tert-butyl-4-(2-methoxy-ethoxymethoxy)-benzene boronic acid are obtained.

12.4: ethyl 4-{5-[3-tert-butyl-4-(2-methoxy-ethoxymethoxy)-phenyl]-thiazol-2-yl}-benzoate In a similar manner to Example 10.5, from 4.7 g (15 mmol) of ethyl 4-(5-bromo-thiazol-2-yl) benzoate (prepared as described in 10.4) and 5.5 g (20 mmol) of 3-tert-butyl-4-(2-methoxy-ethoxymethoxy)-benzene boronic acid, 4.9 g (69%) of ethyl 4-{5-[3-tert-butyl-4-(2-methoxy-ethoxymethoxy)-phenyl]-thiazol-2-yl}-benzoate are obtained.

12.5: ethyl 4-[5-(3-tert-butyl-4-hydroxy-phenyl)-thiazol-2-yl]-benzoate

In a similar manner to Example 11.1, from 4.9 g (10 mmol) of ethyl 4-{5-[3-tert-butyl-4-(2-methoxy-ethoxymethoxy)-phenyl]-thiazol-2-yl}-benzoate, 2.5 g (63%) of 4-[5-(3-tert-butyl-4-hydroxy-phenyl)-thiazol-2-yl]-benzoate are obtained.

12.6: ethyl 4-[5-(3-tert-butyl-4-methoxy-phenyl)-thiazol-2-yl]-benzoate

In a similar manner to Example 9.1, from 200 mg (0.5 mmol) of ethyl 4-[5-(3-tert-butyl-4-hydroxy-phenyl)-thiazol-2-yl]-benzoate and 100 µl (1.6 mmol) of methyl iodide, 191 mg (92%) of 4-[5-(3-tert-butyl-4-methoxy-phenyl)-thiazol-2-yl]benzoate are obtained.

12.7: 4-[5-(3-tert-butyl-4-methoxy-phenyl)-thiazol-2-yl]-benzoic acid

In a similar manner to Example 9.2, from of 187 mg (0.45 mmol) of ethyl 4-[5-(3-tert-butyl-4-methoxy-phenyl)-thiazol-2-yl]-benzoate, 130 mg (74%) 4-[5-(3-tert-butyl-4-methoxy-phenyl)-thiazol-2-yl]-benzoic acid are obtained in the form of a yellow powder.

Example 13: 4-{5-[4-hydroxy-3-(1-methyl-cyclohexyl)-phenyl]-thiazol-2-yl}-benzoic acid

13.1: 4-ethoxymethoxy-3-(1-methyl-cyclohexyl)-benzene boronic acid

In a similar manner to Example 12.3, from 5.7 g (16 mmol) of 4-bromo-1-ethoxymethoxy-2-(1-methyl-cyclohexyl)-benzene (prepared as described in 5.2), 5 g (98%) of 4-ethoxymethoxy-3-(1-methyl-cyclohexyl)-benzene boronic acid are obtained.

13.2: ethyl 4-{5-[4-(2-methoxy-ethoxymethoxy)-3-(1-methyl-cyclohexyl)-phenyl]-thiazol-2-yl}-benzoate In a similar manner to Example 10.5, from 0.8 g (2.4 mmol) of ethyl 4-{5-bromo-thiazol-2-yl}-benzoate (prepared as described in 10.4) and 1 g (2.4 mmol) of 4-ethoxymethoxy-3-(1-methyl-cyclohexyl)-benzene boronic acid, 1 g (66%) of ethyl 4-{5-[4-(2-methoxy-ethoxymethoxy)-3-(1-methyl-cyclohexyl)-phenyl]-thiazol-2-yl}-benzoate are obtained.

13.3: ethyl 4-{5-[4-hydroxy-3-(1-methyl-cyclohexyl)-phenyl]-thiazol-2-yl}-benzoate In a similar manner to Example 11.1, from 1 g (2 mmol) of ethyl 4-{5-[4-(2-methoxy-ethoxymethoxy)-3-(1-methyl-cyclohexyl)-phenyl]-thiazol-2-yl}-benzoate, 550 mg (40%) of ethyl 4-{5-[4-hydroxy-3-(1-methyl-cyclohexyl)-phenyl]-thiazol-2-yl}-benzoate are obtained.

13.4: 4-{5-[4-hydroxy-3-(1-methyl-cyclohexyl)-phenyl]-thiazol-2-yl}-benzoic acid In a similar manner to Example 9.2, from 170 mg (0.4 mmol) of ethyl 4-{5-[4-hydroxy-3-(1-methyl-cyclohexyl)-phenyl]-thiazol-2-yl}-benzoate, 140 mg (87%) 4-{5-[4-hydroxy-3-(1-methyl-cyclohexyl)-phenyl]-thiazol-2-yl}-benzoic acid are obtained in the form of a yellow solid.

Example 14: 4-[5-(5,5,8,8-tetramethyl-5,6,7,8-tetrahydro-naphthalen-2-yl)-thiazol-2-yl]-benzoic acid

14.1: 1,1,4,4-tetramethyl-1,2,3,4-tetrahydro-naphthalene 6-boronic acid

In a similar manner to 12.3, from 5 g (19 mmol) of 6-bromo-1,1,4,4-tetramethyl-1,2,3,4-tetrahydro-naphthalene, 3.5 g (79%) 1,1,4,4-tetramethyl-1,2,3,4-tetrahydro-naphthalene 6-boronic acid are obtained.

14.2: ethyl 4-[5-(5,5,8,8-tetramethyl-5,6,7,8-tetrahydro-naphthalen-2-yl)-thiazol-2-yl]-benzoate In a similar manner to Example 10.5, starting with 0.7 g (2.2 mmol) of ethyl 4-(5-bromo-thiazol-2-yl) benzoate (prepared as described in 10.4) and 0.7 g (2.9 mmol) of 1,1,4,4-tetramethyl-1,2,3,4-tetrahydro-naphthalene 6-boronic acid, 0.5 g (54%) of ethyl 4-[5-(5,5,8,8-tetramethyl-5,6,7,8-tetrahydro-naphthalen-2-yl)-thiazol-2-yl]-benzoate are obtained.

14.3: 4-[5-(5,5,8,8-tetramethyl-5,6,7,8-tetrahydro-naphthalen-2-yl)-thiazol-2-yl]-benzoic acid In a similar manner to Example 9.2, from 0.5 g (1.2 mmol) of ethyl 4-[5-(5,5,8,8-tetramethyl-5,6,7,8-tetrahydro-naphthalen-2-yl)-thiazol-2-yl]-benzoate, 0.42 g (90%) 4-[5-(5,5,8,8-tetramethyl-5,6,7,8-tetrahydro-naphthalen-2-yl)-thiazol-2-yl]-benzoic are obtained.

| Example no. in experimental part | Chemical structure | Compound name | Synthesis pathway | 1H NMR | Appearance |
|---|---|---|---|---|---|
| Example 10 | 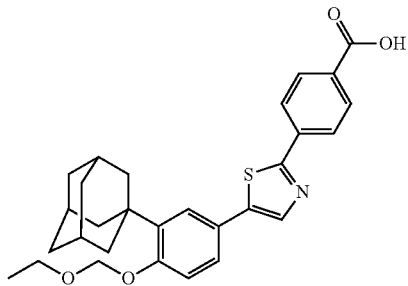 [SMILES: CCOCOc1ccc(-c2cnc(-c3ccc(C(=O)O)cc3)s2)cc1C12CC3CC(CC(C3)C1)C2] | 4-[5-(3-adamantan-1-yl-4-ethoxy methoxy-phenyl)-thiazol-2-yl]-benzoic acid | E (Figure 5) | $^1$H NMR (400 MHz, DMSO): δ (ppm) 8.27 (s, 1 H); 6.06-6.07 (m, 4 H); 7.56 (dd, J = 6.5, 2.2 Hz, 1 H); 7.45 (d, J = 2.3 Hz, 1 H); 7.15 (d, J = 8.6 Hz, 1 H); 8.35 (s, 2 H); 3.73 (q, J = 7.1 Hz, 2 H); 2.12 (s, 6 H); 2.08 (d, J = 4.9 Hz, 3 H); 1.76 (s, 6 H); 1.18 (t, J = 7.16 Hz, 3 H). | yellow solid |

-continued

| Example no. in experimental part | Chemical structure | Compound name | Synthesis pathway | 1H NMR | Appearance |
|---|---|---|---|---|---|
| Example 11 | 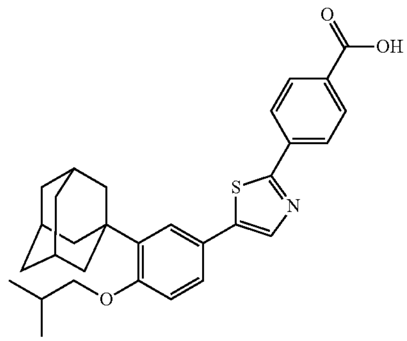 [SMILES: CC(C)COc1ccc(-c2cnc(-c3ccc(C(=O)O)cc3)s2)cc1C12CC3CC(CC(C3)C1)C2] | 4-[5-(3-adamantan-1-yl-4-isobutoxy-phenyl)-thiazol-2-yl]-benzoic acid | E (Figure 5) | $^1$H NMR (400 MHz, CDCl$_3$): δ (ppm) 8.02 (d, J = 8.3 Hz, 2 H); 7.92 (d, J = 6.3 Hz, 2 H);7.84 (s, 1 H); 7.35 (d, J = 2.4 Hz, 1 H); 7.31 (dd, J = 8.5, 2.3 Hz, 1 H); 8.81 (d, J = 8.4 Hz, 1 H); 3.71 (d, J = 8.2 Hz, 2 H); 2.07 (s, 8 H); 2.01 (s, 3 H); 1.70 (s, 6 H); 1.03 (d, J = 8.7 Hz, 6 H). | yellow solid |
| Example 12 | 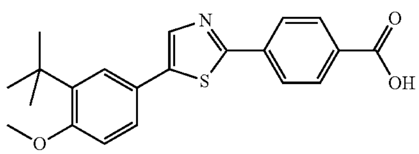 [SMILES: COc1ccc(-c2cnc(-c3ccc(C(=O)O)cc3)s2)cc1C(C)(C)C] | 4-[5-(3-tert-butyl-4-methoxy-phenyl)-thiazol-2-yl]-benzoic acid | E (Figure 5) | $^1$H NMR (400 MHz, CDCl$_3$): δ (ppm) 8.01 (m, 2 H); 7.68 (m, 2 H); 7.80 (d, J = 3.9 Hz, 1 H); 7.35 (s, 1 H); 7.31 (s, 1 H); 8.79 (d, J = 8.3 Hz, 1 H); 3.75 (m, J = 3.7 Hz, 3 H); 1.28 (m, J = 4.0 Hz, 9 H). | yellow solid |
| Example 13 | 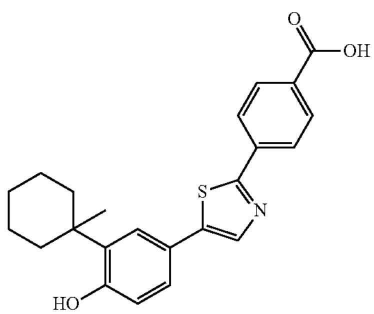 [SMILES: CC1(c2cc(-c3cnc(-c4ccc(C(=O)O)cc4)s3)ccc2O)CCCCC1] | 4-[5-[4-hydroxy-3-(1-methyl-cyclohexyl-phenyl]-thiazol-2-yl]-benzoic acid | E (Figure 5) | $^1$H NMR (400 MHz, DMSO): δ (ppm) 9.82 (s, 1 H); 8.18 (s, 1 H); 8.08 (m, 4 H); 7.42-7.43 (m, 2 H); 8.89 (d, J = 8.0 Hz, 1 H); 2.16 (t, J = 10.0 Hz, 2 H); 1.54-1.68 (m, 8 H); 1.31 (s, 3 H). | yellow solid |
| Example 14 | 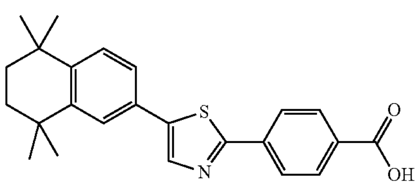 [SMILES: CC1(C)CCC(C)(C)c2cc(-c3cnc(-c4ccc(C(=O)O)cc4)s3)ccc21] | 4-[5-(5,5,8,8-tetramethyl-5,6,7,8-tetrahydro-2-yl)thiazol-2-yl]-benzoic acid | E (Figure 5) | $^1$H NMR (400 MHz, CDCl$_3$): δ (ppm) 8.19-8.21 (m, 2 H); 8.08-8.10 (m, 2 H); 8.04 (d, J = 1.9 Hz, 1 H); 7.53 (s, 1 H); 7.39 (d, 2 H); 1.73 (s, 4 H); 1.35 (s, 6 H); 1.32 (s, 6 H). | yellow solid |
| | | 4-[5-(3-adamantan-1-yl-4-hydroxy-phenyl)-thiazol-2-yl]-benzoic acid | E (Figure 5) | $^1$H NMR (400 MHz, DMSO): δ (ppm) 13.1 (br s, 1H); 9.79 (s, 1 H); 8.19 (s, 1H); 8.06 (s, 4 H); 7.42 (dd, J = 8.3, 2.2 Hz, 1 H); 7.38 (d, J = 2.3 Hz, 1 H); 6.87 (d, J = 8.3 Hz, 1H); 2.12 (s, 8 H); 2.08 (s, 3 H); 1.75 (s, 6 H). | yellow solid |

| Example no. in experimental part | Chemical structure | Compound name | Synthesis pathway | 1H NMR | Appearance |
|---|---|---|---|---|---|
| | | 4-[5-[3-adamantan-1-yl-4-(2-methoxy-ethoxy)-phenyl]-thiazol-2-yl]-benzoic acid | E (Figure 5) | ¹H NMR (400 MHz, CDCl₃): δ (ppm) 8.02 (d, J = 8.2 Hz, 2 H); 7.92 (d, J = 8.2 Hz, 2 H);7.85 (s, 1 H); 7.30-7.33 (m, 2 H); 8.81 (d, J = 8.3 Hz, 1 H); 4.07 (m, J = 4.9 Hz, 2 H); 3.74 (m, J = 4.8 Hz, 2 H); 3.37 (s, 2 H); 2.06 (s, 8 H); 2.01 (s, 3 H); 1.69 (s, 8 H). | yellow solid |
| | | 4-[5-(3-adamantan-1-yl-4-methoxy-phenyl]-thiazol-2-yl]-benzoic acid | E (Figure 5) | ¹H NMR (400 MHz, CDCl₃): δ (ppm) 7.91 (d, J = 8.0 Hz, 2 H); 7.81 (d, J = 7.9 Hz, 2 H); 7.75 (s, 1 H); 7.23 (s, 2 H); 8.74 (d, J = 8.2 Hz, 1 H); 3.89 (s, 3 H); 1.91 (m, J = 12.4 Hz, 9 H); 1.59 (s, 6 H). | yellow solid |
| | | 4-[5-(3-adamantan-1-yl-4-propoxy-phenyl]-thiazol-2-yl]-benzoic acid | E (Figure 5) | ¹H NMR (400 MHz, CDCl₃): δ (ppm) 8.00 (d, J = 8.1 Hz, 2 H); 7.89 (d, J = 8.0 Hz, 2 H); 7.82 (s, 1 H); 7.28-7.31 (m, 2 H); 8.79 (d, J = 8.3 Hz, 1 H); 3.87 (t, J = 8.3 Hz, 2 H); 2.04 (s, 8 H); 1.98 (s, 3 H); 1.78-1.81 (m, 2 H); 1.67 (s, 6 H); 1.02 (t, J = 7.4 Hz, 3 H). | yellow solid |
| | | 4-[5-(3-adamantan-1-yl-4-ethoxy-phenyl)-thiazol-2-yl]-benzoic acid | E (Figure 5) | ¹H NMR (400 MHz, CDCl₃): δ (ppm) 8.02 (d, J = 8.2 Hz, 2 H); 7.91 (d, J = 8.2 Hz, 2 H); 7.84 (s, 1 H); 7.29-7.32 (m, 2 H); 6.80 (d, J = 8.3 Hz, 1 H); 4.00 (q, J = 6.9 Hz, 2 H); 2.06 (s, 6 H); 2.00 (s, 3 H); 1.69 (s, 8 H); 1.41 (t, J = 6.9 Hz, 3 H). | yellow solid |
| | | 4-{5-[4-(2-methoxy-ethoxymethoxy)-3-(1-methyl-cyclohexyl)phenyl]-thiazol-2-yl}-benzoic acid | E (Figure 5) | ¹H NMR (400 MHz, CDCl₃): δ (ppm) 8.18 (d, J = 8.2 Hz, 2 H); 8.08 (d, J = 8.2 Hz, 2 H); 7.98 (s, 1 H); 7.54 (d, J = 2.4 Hz, 1 H); 7.40 (dd, J = 8.7, 2.1 Hz, 1 H); 7.24 (d, J = 8.5 Hz, 1 H); 5.35 (s, 2 H); 3.83-3.86 (m, 2 H); 3.60 (m, J = 4.9 Hz, 2 H) 3.39-3.40 (m, 3 H); 2.12 | yellow solid |

-continued

| Example no. in experimental part | Chemical structure | Compound name | Synthesis pathway | 1H NMR | Appearance |
|---|---|---|---|---|---|
| | | | | (m, J = 11.3 Hz, 2 H); 1.74 (m, 2 H); 1.40 (m, 6 H); 1.34 (s, 3 H). | |
| | | 4-[5-[4-isobutoxy-3-(1-methyl-cyclohexyl)-phenyl]-thiazol-2-yl]-benzoic acid | E (Figure 5) | $^1$H NMR (400 MHz, DMSO): δ (ppm) 8.23 (s, 1 H); 8.05 (s, 4 H); 7.54 (d, J = 8.6 Hz, 1 H); 7.50 (d, J = 2.6 Hz, 1 H); 7.05 (d, J = 8.5 Hz, 1 H); 3.82 (d, J = 6.1 Hz, 2 H); 2.17 (s, 2 H); 2.08 (m, 1 H); 1.89 (d, J = 12.4 Hz, 2 H) 1.55 (m, 2 H); 1.44 (. 2 H); 1.32 (s, 3 H); 1.04 (d, J = 8.8 Hz, 6 H). | yellow solid |
| | | 4-[5-[4-methoxy-3-(1-methyl-cyclohexyl)-phenyl]-thiazol-2-yl]-benzoic acid | E (Figure 5) | $^1$H NMR (400 MHz, DMSO): δ (ppm) 13.2 (br s, 1H); 8.25 (s, 1 H); 8.05-8.07 (m, 4 H); 7.59 (dd, J = 8.4, 2.3 Hz, 1 H); 7.50 (s, 1 H); 7.10 (d, J = 8.5 Hz, 1 H); 3.84 (s, 3 H); 2.09 (t, J = 10.1 Hz, 2 H); 1.72 (d, J = 12.3 Hz, 2 H); 1.37-1.56 (br m, 6 H); 1.29 (s, 3 H). | yellow solid |
| | | 4-{5-[3-(1-methyl-cyclohexyl)-4-propoxy-phenyl]-thiazol-2-yl}-benzoic acid | E (Figure 5) | 1H NMR (400 MHz, DMSO): δ (ppm) 8.24 (s, 1H); 8.06 (t, J = 9.3 Hz, 4 H); 7.55 (d, J = 8.6 Hz, 1 H); 7.51 (s, 1 H); 7.08 (d, J = 8.5 Hz, 1 H); 2.17 (m, J = 9.9 Hz, 2 H); 1.77-1.80 (m, 2 H); 1.69 (m, J = 12.6 Hz, 2 H); 1.56 (m, 2 H); 1.45 (m, 2 H); 1.36 (m, J = 10.0 Hz, 2 H); 1.31 (s, 3 H); 1.23 (m, J = 8.9 Hz, 2 H); 1.04 (t, J = 7.4 Hz, 3 H). | yellow solid |
| | | 4-[5-[4-cyclopropylmethoxy)-3-(1-methyl-cyclohexyl)-phenyl]-thiazol-2-yl]-benzoic acid | E (Figure 5) | 1H NMR (400 MHz, DMSO): δ (ppm) 8.24 (s, 1H); 8.08 (t, J = 9.3 Hz, 4 H); 7.55 (d, J = 8.8 Hz, 1 H); 7.51 (s, 1 H); 7.06 (d, J = 9.9 Hz, 2 H); 1.77-1.80 (m, 2 H); 1.89 (d, J = 12.6 Hz, 3 H); 1.56 (br s, 3 H); 1.45 (br s, 5 H); 1.38 (t, J = 10.0 Hz, 3 H); 1.31 (s, 3 H); 1.23 (d, J = 6.9 Hz, 3 H); 1.04 (t, J = 7.4 Hz, 3 H). | yellow solid |

| Example no. in experimental part | Chemical structure | Compound name | Synthesis pathway | 1H NMR | Appearance |
|---|---|---|---|---|---|
| | | 4-[5-[4-ethylcarbamoylmethoxy)-3-(1-methyl-cyclohexyl)-phenyl]-thiazol-2-yl]-benzoic acid | E (Figure 5) | ¹H NMR (400 MHz, DMSO): δ (ppm) 13.12 (br s, 1H); 8.28 (s, 1 H); 8.06 (s, 4 H); 7.93 (s, 1 H); 7.57 (d, J = 8.5 Hz, 1 H); 7.52 (s, 1 H); 8.98 (d, J = 8.5 Hz, 1 H); 4.55 (s, 2 H); 3.18 (t, J = 7.3 Hz, 2 H); 2.12 (m, 2 H); 1.74 (m, 2 H); 1.56 (m, 3 H); 1.46 (m, 5 H); 1.34 (s, 3 H); 1.17 (m, 1 H); 1.06 (t, J = 7.3 Hz, 3 H). | yellow solid |
| | | 4-[5-(3-adamantan-1-yl-4-propylamino-phenyl)-thiazol-2-yl]-benzoic acid | E (Figure 5) | ¹H NMR (400 MHz, CDCl₃): δ (ppm) 8.08 (d, J = 8.2 Hz, 2 H); 7.95 (d, J = 8.2 Hz, 2 H); 7.85 (s, 1 H); 7.35 (s, 1 H); 7.33 (d, J = 8.7 Hz, 1 H); 8.83 (d, J = 8.4 Hz, 1 H); 3.89 (t, J = 8.0 Hz, 1 H); 3.13 (t, J = 6.9 Hz, 2 H); 2.12 (s, 3 H); 2.08 (s, 6 H); 1.70-1.75 (m, 8 H); 1.03 (t, J = 7.4 Hz, 3 H). | yellow solid |
| | | 4-[5-(3-tert-butyl-4-ethoxy-phenyl)-thiazol-2-yl]-benzoic acid | E (Figure 5) | 1H NMR (400 MHz, CDCl3): δ (ppm) 7.99 (d, J = 8.3 Hz, 2 H); 7.88 (d, J = 8.3 Hz, 2 H); 7.81 (s, 1 H); 7.36 (d, J = 2.3 Hz, 1 H); 7.29 (dd, J = 8.4, 2.3 Hz, 1 H); 6.78 (d, J = 8.5 Hz, 1 H); 3.98 (q, J = 7.0 Hz, 2 H); 1.37 (t, J = 6.9 Hz, 3 H); 1.30 (s, 9 H). | yellow solid |
| | | 4-[5-(3-tert-butyl-4-propoxy-phenyl)-thiazol-2-yl]-benzoic acid | E (Figure 5) | ¹H NMR (400 MHz, CDCl₃): δ (ppm) 8.04 (d, J = 8.3 Hz, 2 H); 7.94 (d, J = 8.3 Hz, 2 H); 7.88 (s, 1 H); 7.42 (s, 1 H); 7.34 (d, J = 8.7 Hz, 1 H); 8.83 (d, J = 8.8 Hz, 1 H); 3.92 (m, 2 H); 1.82 (m, J = 9.7 Hz, 2 H); 1.36 (s, 9 H); 1.04 (m, 3 H). | yellow solid |
| | | 4-{5-[3-tert-butyl-4-(2,2,2-trifluoro-ethoxy-phenyl)-thiazol-2-yl]-benzoic acid | E (Figure 5) | ¹H NMR (400 MHz, CDCl₃): δ (ppm) 8.04 (d, J = 8.0 Hz, 2 H); 7.94 (d, J = 8.2 Hz, 2 H); 7.88 (s, 1 H); 7.47 (s, 1 H); 7.37 (d, J = 8.3 Hz, 1 H); 6.76 (d, J = 8.4 Hz, 1 H); 4.35 (q, J = 8.0 Hz, 2 H); 1.35 (s, 9 H). | yellow solid |

| Example no. in experimental part | Chemical structure | Compound name | Synthesis pathway | 1H NMR | Appearance |
|---|---|---|---|---|---|
| | | 4-[5-(3-tert-butyl-4-cyclopropylmethoxy-phenyl)-thiazol-2-yl]-benzoic acid | E (Figure 5) | ¹H NMR (400 MHz, CDCl₃): δ (ppm) 8.08 (d, J = 8.0 Hz, 2 H); 7.96 (d, J = 8.1 Hz, 2 H); 7.89 (s, 1 H); 7.45 (d, J = 2.5 Hz, 1 H); 7.35 (d, J = 8.4 Hz, 1 H); 6.80 (d, J = 8.4 Hz, 1 H); 3.83 (sd, J = 6.9 Hz, 2 H); 1.41 (s, 9 H); 0.62 (d, J = 7.7 Hz, 2 H); 0.33 (d, J = 5.1 Hz, 2 H); −0.05 (s, 1 H). | yellow solid |
| | | 4-{5-[3-tert-butyl-4-(2-methoxy-ethoxy)-phenyl]-thiazol-2-yl}-benzoic acid | E (Figure 5) | ¹H NMR (400 MHz, CDCl₃): δ (ppm) 8.21 (d, J = 8.1 Hz, 2 H); 8.09 (d, J = 8.1 Hz, 2 H); 8.00 (s, 1 H); 7.54 (s, 1 H); 7.45 (d, J = 8.4 Hz, 1 H); 6.94 (d, J = 8.4 Hz, 1 H); 4.21 (t, J = 4.8 Hz, 2 H); 3.86 (t, J = 4.8 Hz, 2 H); 3.49 (s, 3 H); 1.47 (s, 9 H). | yellow solid |
| | | 4-{5-[3-tert-butyl-4-(2,2-dimethoxy-ethoxy)-phenyl]-thiazol-2-yl}-benzoic acid | E (Figure 5) | ¹H NMR (400 MHz, CDCl₃): δ (ppm) 8.22 (d, J = 8.1 Hz, 2 H); 8.09 (d, J = 8.1 Hz, 2 H); 8.01 (s, 1 H); 7.55 (s, 1 H); 7.46 (d, J = 8.4 Hz, 1 H); 6.92 (d, J = 8.4 Hz, 1 H); 4.87 (t, J = 5.3 Hz, 1 H); 4.09 (d, J = 5.3 Hz, 2 H); 3.51 (s, 6 H); 1.47 (s, 9 H). | yellow solid |
| | | 4-{5-[3-(1-methyl-cyclohexyl)-4-(2,2,2-trifluoro-ethoxy)-phenyl]-thiazol-2-yl}-benzoic acid | E (Figure 5) | ¹H NMR (400 MHz, CDCl₃): δ (ppm) 8.08 (dd, J = 7.8, 2.6 Hz, 2 H); 7.94-7.96 (m, 3 H); 7.53 (s, 1 H); 7.39 (dd, J = 8.3, 2.4 Hz, 1 H); 8.79 (d, J = 8.5 Hz, 1 H); 4.38 (q, J = 8.1 Hz, 2 H); 2.10 (br s, 2 H); 1.68 (br s, 2 H); 1.56 (br s, 2 H); 1.37 (s, 3 H); 1.31 (s, 1 H); 1.29 (d, J = 2.5 Hz, 3 H); 1.20 (s, 1 H); | yellow solid |
| | | 4-[5-(3-tert-butyl-4-ethylcarbamoylmethoxy-phenyl)-thiazol-2-yl]-benzoic acid | E (Figure 5) | ¹H NMR (400 MHz, CDCl₃): δ (ppm) 8.20 (d, J = 8.2 Hz, 2 H); 8.07 (d, J = 8.2 Hz, 2 H); 8.00 (s, 1 H); 7.57 (d, J = 2.3 Hz, 1 H); 7.46 (dd, J = 8.4, 2.2 Hz, 1 H); 6.89 (d, J = 8.5 Hz, 1 H); 6.48 (s, 1 H); 4.61 (s, 2 H); 3.44 (p, J = 6.8 Hz, 2 H); 1.49 (s, 9 H); 1.21 (t, J = 7.3 Hz, 3 H). | yellow solid |

| Example no. in experimental part | Chemical structure | Compound name | Synthesis pathway | 1H NMR | Appearance |
|---|---|---|---|---|---|
| | | 4-[5-(3-tert-butyl-4-isobutoxy-phenyl)-thiazol-2-yl]-benzoic acid | E (Figure 5) | ¹H NMR (400 MHz, CDCl₃): δ (ppm) 8.19 (d, J = 8.2 Hz, 2 H); 8.07 (d, J = 8.2 Hz, 2 H); 7.98 (s, 1 H); 7.52 (d, J = 2.3 Hz, 1 H); 7.43 (dd, J = 8.4, 2.3 Hz, 1 H); 6.91 (d, J = 8.5 Hz, 1 H); 3.82 (d, J = 6.3 Hz, 2 H); 2.18-2.20 (m, 1 H); 1.46 (s, 9 H); 1.11 (d, J = 6.7 Hz, 6 H). | yellow solid |
| | | 4-[5-(3-adamantan-yl-4-propylamino-phenyl)-thiazol-2-yl]-benzoic acid | E (Figure 5) | | |
| | | 4-[5-(3-tert-butyl-4-ethylsulfanyl-phenyl)-thiazol-2-yl]-benzoic acid | E (Figure 5) | | |
| | | 4-[5-(3-tert-butyl-4-ethylsulfanyl-phenyl)-thiazol-2-yl]-benzoic acid | | | |

| Example no. in experimental part | Chemical structure | Compound name | Synthesis pathway | 1H NMR | Appearance |
|---|---|---|---|---|---|
| | 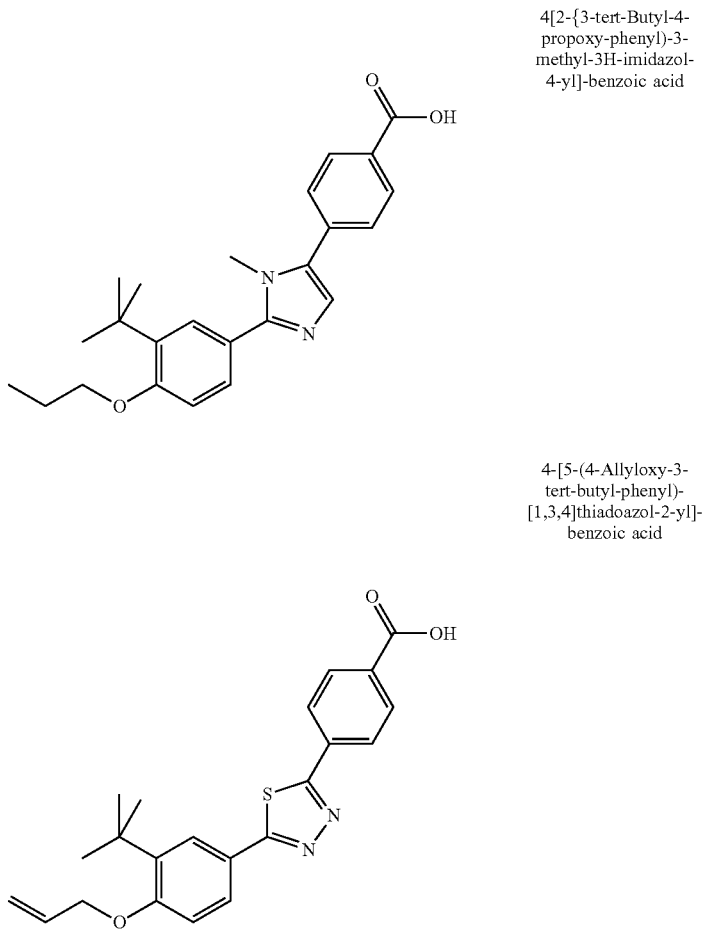 | 4-[5-(3-tert-butyl-4-hydroxy-phenyl)-thiazol-2-yl]-benzoic acid | E (Figure 5) | | |

F: Description of the Heteroaryl Compounds Described in Figures 6,7 and 8

| CHEMISTRY | Compound name |
|---|---|
| | 4[2-{3-tert-Butyl-4-propoxy-phenyl)-3-methyl-3H-imidazol-4-yl]-benzoic acid |
| | 4-[5-(4-Allyloxy-3-tert-butyl-phenyl)-[1,3,4]thiadoazol-2-yl]-benzoic acid |

| CHEMISTRY | Compound name |
|---|---|
| | 4-{2-[3-(1-Methyl-cyclohexyl)-4-(pyridin-4-ylmethoxy)-phenyl]-oxazol-4-yl}-benzoic acid |
| | 4-[5-(4-Ethoxy-3-pyrrolidin-1-yl-phenyl)-4H-[1,2,4]triazol-3-yl]-benzoic acid |
| | 4-{5-[3-Diethylamino-4-(4-fluoro-benzyloxy)-phenyl]-[1,3,4]thiadiazol-2-yl}benzoic acid |
| | 4-[5-(3-tert-Butyl-4-isobutoxy-phenyl)-[1,3,4]thiadiazol-2-yl]-benzoic acid |

-continued

| CHEMISTRY | Compound name |
|---|---|
| | 4-[5-(4-Butoxy-3-tert-butyl-phenyl)-1-methyl-1H-pyrrol-2-yl]-benzoic acid |
| | 4-{5-[4-(2-Amino-ethoxy)-3-tert-butyl-phenyl]-thiophen-2-yl}-benzoic acid |
| | 4-[2-(3-tert-Butyl-4-cyclopropylmethylsulfanyl-phenyl)-oxazol-5-yl]-benzoic acid |
| | 3-[5-(3-Adamantan-1-yl-4-hydroxy-phenyl)-2-ethyl-2H-pyrazol-3-yl]-benzoic acid |

G: Molecular Pharmacology Test

Principle:

The activity of our molecules on the RAR is measured using a recombinant line expressing the ligand-biding domain (LBD) of RAR fused with the DNA binding domain (DBD) of the estrogen receptors. The specific transactivation of the receptor on the receptor estrogen response element (ERE) leads to transcription of luciferase. The expression of this reporter gene is quantified by luminescence after addition of its substrate, luciferin.

This line was produced by Prof. Ballaguer (INSERM 439, Montpellier) after stable transfection of HeLa by ERE-βGlob-Luc-SV-Neo and RAR(α, β, γ)-ER-DBD-puro plasmids.

The compounds are evaluated by dose-response (10000 nM-0.04 nM) normalized relative to a basal control and a maximum efficacy control (CD0193, reference agonist with 100 nM saturating concentration): Y=((X−0%)/(100%−0%))*100.

The affinity ($EC_{50}$ in nM) and efficacy (in %) are measured using the XLfit (IDBS) software according to a four-parameter nonlinear regression (model 205).

Protocol:

HeLa ERE Luc-hRAR cells are inoculated on 96 well microplates (10,000 cell/100 μL). After 4 hours of incubation at 37° C./5% $CO_2$, they are treated with 5 μL of 20× products (0.1 final DMSO). After 18 hours of incubation at 37° C./5% CO2, 100 μL of revealing solution (luciferin in lysis buffer) are added and the luminescence is measured by a microplate reader.

Results:

| Compound name | RARα | | | RARβ | | | RARγ | | |
|---|---|---|---|---|---|---|---|---|---|
| | $EC_{50}$ (nM) | Efficacy | Comments | $EC_{50}$ (nM) | Efficacy (%) | Comments | $EC_{50}$ (nM) | Efficacy (%) | Comments |
| 4-[5-(5,5,8,8-tetramethyl-5,6,7,8-tetrahydro-naphthalen-2-yl)-thiazol-2-yl]-benzoic acid | 9793 | 64 | Total agonist | 52 | 110 | Total agonist | 162 | 78 | Total agonist |
| 4-[3-(3-tert-butyl-4-ethoxymethoxy-phenyl)-[1,2,4]oxadiazol-5-yl]-benzoic acid | 650 | 104 | Total agonist | 6.2 | 95 | Total agonist | 10 | 88 | Total agonist |
| 4-[3-(3-tert-butyl-4-hydroxy-phenyl)-[1,2,4]oxadiazol-5-yl]-benzoic acid | 107 | 106 | Total agonist | 3.0 | 110 | Total agonist | 2.4 | 110 | Total agonist |
| 4-{3-[4-ethoxymethoxy-3-(1-methyl-cyclohexyl)-phenyl]-[1,2,4]oxadiazol-5-yl}-benzoic acid | 90 | 80 | Total agonist | 0.56 | 107 | Total agonist | 0.90 | 102 | Total agonist |
| 4-[3-(3-tert-butyl-4-ethoxy-phenyl)-[1,2,4]oxadiazol-5-yl]-benzoic acid | 255 | 105 | Total agonist | 3.8 | 92 | Total agonist | 9.3 | 96 | Total agonist |
| 4-{5-[3-(1-methyl-cyclohexyl)-4-propoxy-phenyl]-thiazol-2-yl}-benzoic acid | 3175 | 68 | Total agonist | 635 | 90 | Total agonist | 1033 | 74 | Total agonist |
| 4-[5-(3-tert-butyl-4-methoxy-phenyl)-thiazol-2-yl]-benzoic acid | 109 | 53 | Partial agonist | 164 | 46 | Partial agonist | 66 | 40 | Partial agonist |

(*) IA = Inactive
(**) ND = $EC_{50}$ not determinable

4-[5-(3-tert-butyl-4-methoxy-phenyl)-thiazol-2-yl]-benzoic acid is a partial agonist on the three RAR isoforms.

The other compounds present are total agonists on the three RAR isoforms with a range of activity extending from $10^{-9}$ to $10^{-6}$M. They are preferentially active on RAR beta and gamma.

The invention claimed is:

1. A compound of formula (I)

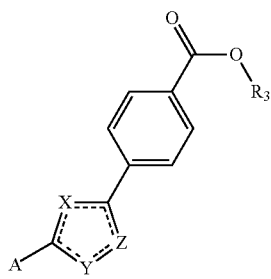

wherein:

A represents:

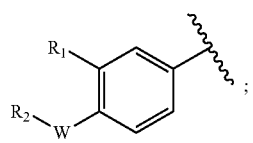

$R_1$ represents a branched alkyl radical, a substituted cycloalkyl radical, or an $NR_4R_5$ radical;

$R_2$ is a hydrogen atom, a linear or branched alkyl radical, a polyether radical, or a mono or polyhydroxyalkyl radical;

$R_3$ is a hydrogen atom;

$R_4$ and $R_5$, identical or different, represent a hydrogen atom, a linear or branched alkyl radical, a substituted alkyl radical, or an acyl radical;

$R_4$ and $R_5$ taken together can also be linked and form an optionally substituted azetidine, pyrrolidine or piperidine heterocycle with the nitrogen atom with which they are linked;

W represents O or S;

X, Y, Z, identical or different represent O, S, N, $NR_6$ or CH;

the central heterocycle

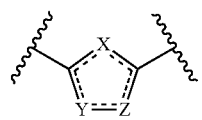

corresponds to one of the structures presented below, the dashed bonds may be a single or double bond depending on the nature of atoms X, Y and Z and their covalence

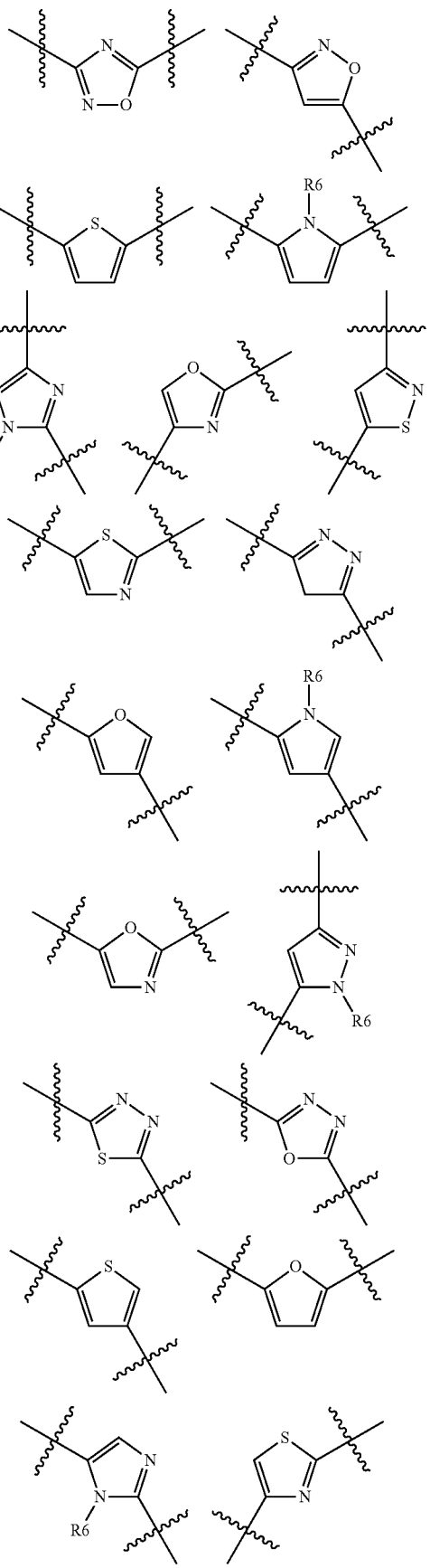

-continued

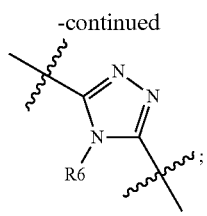

R$_6$ represents a hydrogen or alkyl radical;
as well as their addition salts with a pharmaceutically-acceptable acid, their addition salts with a pharmaceutically-acceptable base and their enantiomers.

2. The compound as defined by claim 1, wherein:
A represents a group

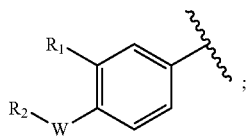

R$_1$ is a branched alkyl radical or an NR$_4$R$_5$ radical;
R$_2$ is a hydrogen atom, a linear or branched alkyl radical, or a monohydroxyalkyl radical;
R$_3$ is a hydrogen atom;
R$_4$ and R$_5$, identical or different, represent a linear or branched alkyl radical;
R$_4$ and R$_5$ taken together can also be linked and form an optionally substituted pyrrolidine heterocycle with the nitrogen atom with which they are linked; and
W is O.

3. The compound according to claim 1, wherein A represents:

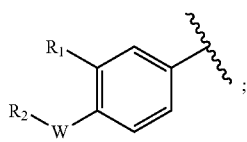

R$_1$ is a tert-butyl or 1-methyl-cyclohexyl radical;
R$_2$ is an ethoxymethyl radical;
W is O;
R$_3$ is a hydrogen atom;
X represents S, Y represents CH and Z represents N; or X represents N, Y represents N and Z represents O.

4. The compound as defined by claim 1, wherein the compound is selected from the group consisting of:
4-[5-(3-tert-butyl-4-hydroxy-phenyl)-thiazol-2-yl]-benzoic acid;
4-[3-(3-tert-butyl-4-ethoxymethoxy-phenyl)-[1,2,4]oxadiazol-5-yl]-benzoic acid;
4-{5-[4-(2-methoxy-ethoxymethoxy)-3-(1-methyl-cyclohexyl)-phenyl]-thiazol-2-yl}-benzoic acid;
4-[3-(3-tert-butyl-4-hydroxy-phenyl)-[1,2,4]oxadiazol-5-yl]-benzoic acid;
4-{3-[4-ethoxymethoxy-3-(1-methyl-cyclohexyl)-phenyl]-[1,2,4]-oxadiazol-5-yl}-benzoic acid;
4-{3-[4-hydroxy-3-(1-methyl-cyclohexyl)-phenyl]-[1,2,4]-oxadiazol-5-yl}-benzoic acid;
4-{3-[3-tert-butyl-4-(2-methoxy-ethoxy)-phenyl]-[1,2,4]-oxadiazol-5-yl}-benzoic acid;
4-[3-(3-tert-butyl-4-methoxy-phenyl)-[1,2,4]oxadiazol-5-yl]-benzoic acid;
4-[3-(3-tert-butyl-4-ethoxy-phenyl)-[1,2,4]oxadiazol-5-yl]-benzoic acid;
4-[3-(3-tert-butyl-4-propoxy-phenyl)-[1,2,4]oxadiazol-5-yl]-benzoic acid;
4-[3-(3-tert-butyl-4-isobutoxy-phenyl)-[1,2,4]oxadiazol-5-yl]-benzoic acid;
4-{3-[3-tert-Butyl-4-(2,2-dimethoxy-ethoxy)-phenyl]-[1,2,4]-oxadiazol-5-yl}-benzoic acid;
4-[3-(3-tert-butyl-4-[1,3]dioxolan-2-ylmethoxy)-phenyl]-[1,2,4]oxadiazol-5-yl)-benzoic acid;
4-{5-[4-hydroxy-3-(1-methyl-cyclohexyl)-phenyl]-thiazol-2-yl}-benzoic acid;
4-{5-[4-isobutoxy-3-(1-methyl-cyclohexyl)-phenyl]-thiazol-2-yl}-benzoic acid;
4-{5-[4-methoxy-3-(1-methyl-cyclohexyl)-phenyl]-thiazol-2-yl}-benzoic acid;
4-{5-[3-(1-methyl-cyclohexyl)-4-propoxy-phenyl]-thiazol-2-yl}-benzoic acid,
4-{5-[4-cyclopropylmethoxy-3-(1-methyl-cyclohexyl)-phenyl]-thiazol-2-yl}-benzoic acid;
4-[5-(3-tert-butyl-4-methoxy-phenyl)-thiazol-2-yl]-benzoic acid;
4-[5-(3-tert-butyl-4-ethoxy-phenyl)-thiazol-2-yl]-benzoic acid;
4-[5-(3-tert-butyl-4-propoxy-phenyl)-thiazol-2-yl]-benzoic acid;
4-[5-(3-tert-butyl-4-cyclopropylmethoxy-phenyl)-thiazol-2-yl]-benzoic acid;
4-{5-[3-tert-butyl-4-(2-methoxy-ethoxy)-phenyl]-thiazol-2-yl}-benzoic acid;
4-{5-[3-tert-butyl-4-(2,2-dimethoxy-ethoxy)-phenyl]-thiazol-2-yl}-benzoic acid;
4-{3-[4-methoxy-3-(1-methyl-cyclohexyl)-phenyl]-[1,2,4]-oxadiazol-5-yl}-benzoic acid;
4-{3-[3-(1-methyl-cyclohexyl)-4-propoxy-phenyl]-[1,2,4]oxadiazol-5-yl}-benzoic acid;
4-{3-[4-isobutoxy-3-(1-methyl-cyclohexyl)-phenyl]-[1,2,4]-oxadiazol-5-yl}-benzoic acid;
4-{3-[4-(2,2-dimethoxy-ethoxy)-3-(1-methyl-cyclohexyl)-phenyl]-[1,2,4]oxadiazol-5-yl}-benzoic acid;
4-[5-(3-tert-butyl-4-isobutoxy-phenyl)-thiazol-2-yl]-benzoic acid;
4-{3-[4-([1,3]dioxolan-2-ylmethoxy)-3-(1-methylcyclohexyl)-phenyl]-[1,2,4]oxadiazol-5-yl}-benzoic acid;
4-{3-[3-tert-butyl-4-(2-hydroxy-ethoxy)-phenyl]-[1,2,4]-oxadiazol-5-yl}-benzoic acid;
4-{3-[3-tert-butyl-4-(3-hydroxy-propoxy)-phenyl]-[1,2,4]-oxadiazol-5-yl}-benzoic acid;
4-[5-(3-tert-butyl-4-propoxy-phenyl)-1-methyl-1H-imidazol-2-yl]-benzoic acid;
4-[5-(3-tert-butyl-4-isobutoxy-phenyl)-[1,3,4]thiadiazol-2-yl]-benzoic acid;
4-[5-(4-butoxy-3-tert-butyl-phenyl)-1-methyl-1H-pyrrol-2-yl]-benzoic acid;
4-[5-(3-tert-butyl-4-hydroxy-phenyl)-[1,3,4]oxadiazol-2-yl]-benzoic acid;
4-[5-(3-tert-butyl-4-ethoxy-phenyl)-[1,3,4]oxadiazol-2-yl]-benzoic acid; and
4-[5-(4-hydroxy-3-pyrrolidin-1-yl-phenyl)-[1,3,4]oxadiazol-2-yl]-benzoic acid
or pharmaceutically acceptable salts thereof.

5. The compound as defined by claim 1, wherein the compound is selected from the group consisting of:
4-[3-(3-tert-butyl-4-ethoxymethoxy-phenyl)-[1,2,4]oxadiazol-5-yl]-benzoic acid;

4-[3-(3-tert-butyl-4-hydroxy-phenyl)-[1,2,4]oxadiazol-5-yl]-benzoic acid;
4-{3-[4-ethoxymethoxy-3-(1-methyl-cyclohexyl)-phenyl]-[1,2,4]oxadiazol-5-yl}-benzoic acid;
4-[3-(3-tert-butyl-4-ethoxy-phenyl)-[1,2,4]oxadiazol-5-yl]-benzoic acid;
4-{5-[3-(1-methyl-cyclohexyl)-4-propoxy-phenyl]-thiazol-2-yl}-benzoic acid; and
4-[5-(3-tert-butyl-4-methoxy-phenyl)-thiazol-2-yl]-benzoic acid or pharmaceutically acceptable salts thereof.

6. A pharmaceutical composition comprising the compound as defined by claim 1.

7. A medicament comprising an effective amount of the compound as defined by claim 1.

8. The compound according to claim 1, wherein the central heterocycle is:

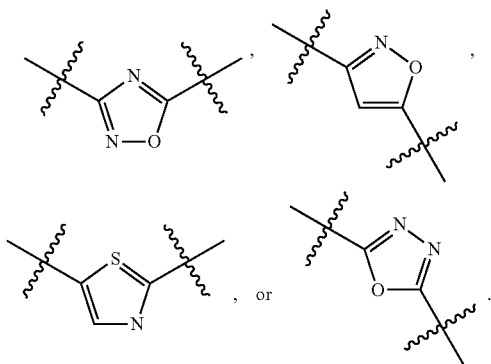

9. The compound according to claim 2, wherein the central heterocycle is

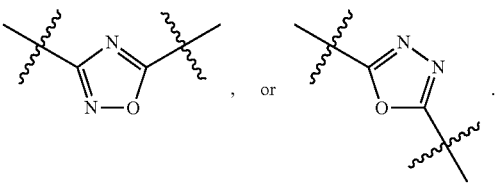 [SMILES: *c1noc(*)n1 ; *c1nnc(*)o1]

10. A compound selected from the group consisting of:
4-[3-(3-adamantan-1-yl-4-ethoxymethoxy-phenyl)-[1,2,4]oxadiazol-5-yl]-benzoic acid;
4-[5-(5,5,8,8-tetramethyl-5,6,7,8-tetrahydro-naphthalen-2-yl)-thiazol-2-yl]-benzoic acid;
4-[5-(3-adamantan-1-yl-4-ethoxymethoxy-phenyl)-thiazol-2-yl]-benzoic acid;
4-{5-[3-adamantan-1-yl-4-(2-methoxy-ethoxymethoxy)-phenyl]-[1,3,4]-oxadiazol-2-yl}-benzoic acid;
4-[5-(3-adamantan-1-yl-4-hydroxy-phenyl)-thiazol-2-yl]-benzoic acid;
4-[3-(3-adamantan-1-yl-4-hydroxy-phenyl)-[1,2,4]oxadiazol-5-yl]-benzoic acid;
4-{5-[3-adamantan-1-yl-4-(2-methoxy-ethoxy)-phenyl]-thiazol-2-yl}-benzoic acid;
4-[5-(3-tert-butyl-4-hydroxy-phenyl)-thiazol-2-yl]-benzoic acid;
4-[5-(3-adamantan-1-yl-4-methoxy-phenyl)-thiazol-2-yl]-benzoic acid;
4-[5-(3-adamantan-1-yl-4-isobutoxy-phenyl)-thiazol-2-yl]-benzoic acid;
4-[5-(3-adamantan-1-yl-4-propoxy-phenyl)-thiazol-2-yl]-benzoic acid;
4-[5-(3-adamantan-1-yl-4-ethoxy-phenyl)-thiazol-2-yl]-benzoic acid;
4-[5-(3-adamantan-1-yl-4-hydroxy-phenyl)-[1,3,4]oxadiazol-2-yl]-benzoic acid;
4-[5-(3-adamantan-1-yl-4-isobutoxy-phenyl)-[1,3,4]oxadiazol-2-yl]-benzoic acid;
4-{3-[3-adamantan-1-yl-4-(2-methoxy-ethoxy)-phenyl]-[1,2,4]oxadiazol-5-yl}-benzoic acid;
4-{3-[3-adamantan-1-yl-4-(2-dimethylamino-ethoxy)-phenyl]-[1,2,4]oxadiazol-5-yl}-benzoic acid;
4-[3-(3-adamantan-1-yl-4-methoxy-phenyl)-[1,2,4]oxadiazol-5-yl]-benzoic acid;
4-[3-(3-adamantan-1-yl-4-ethoxy-phenyl)-[1,2,4]oxadiazol-5-yl]-benzoic acid;
4-[3-(3-adamantan-1-yl-4-propoxy-phenyl)-[1,2,4]oxadiazol-5-yl]-benzoic acid;
4-[3-(3-adamantan-1-yl-4-isobutoxy-phenyl)-[1,2,4]oxadiazol-5-yl]-benzoic acid;
4-{3-[3-adamantan-1-yl-4-(2,2-dimethoxy-ethoxy)-phenyl]-[1,2,4]oxadiazol-5-yl}-benzoic acid;
4-[3-(3-tert-butyl-4-ethoxymethoxy-phenyl)-[1,2,4]oxadiazol-5-yl]-benzoic acid;
4-{5-[4-(2-methoxy-ethoxymethoxy)-3-(1-methyl-cyclohexyl)-phenyl]-thiazol-2-yl}-benzoic acid;
4-[5-(3-adamantan-1-yl-4-methoxy-phenyl)-[1,3,4]oxadiazol-2-yl]-benzoic acid;
4-[5-(3-adamantan-1-yl-4-ethoxy-phenyl)-[1,3,4]oxadiazol-2-yl]-benzoic acid;
4-5-(3-adamantan-1-yl-4-cyclopropylmethoxy-phenyl)-[1,3,4]oxadiazol-2-yl]-benzoic acid;
4-{5-[3-adamantan-1-yl-4-(2,2,2-trifluoro-ethoxy)-phenyl]-[1,3,4]-oxadiazol-2-yl}-benzoic acid;
4-[5-(3-adamantan-1-yl-4-propoxy-phenyl)-[1,3,4]oxadiazol-2-yl]-benzoic acid;
4-[3-(3-tert-butyl-4-hydroxy-phenyl)-[1,2,4]oxadiazol-5-yl]-benzoic acid;
4-{3-[4-ethoxymethoxy-3-(1-methyl-cyclohexyl)-phenyl]-[1,2,4]-oxadiazol-5-yl}-benzoic acid;
4-{3-[4-hydroxy-3-(1-methyl-cyclohexyl)-phenyl]-[1,2,4]-oxadiazol-5-yl}-benzoic acid;
4-{3-[3-tert-butyl-4-(2-methoxy-ethoxy)-phenyl]-[1,2,4]-oxadiazol-5-yl}-benzoic acid;
4-{3-[3-tert-butyl-4-(2-dimethylamino-ethoxy)-phenyl]-[1,2,4]-oxadiazol-5-yl}-benzoic acid;
4-[3-(3-tert-butyl-4-methoxy-phenyl)-[1,2,4]oxadiazol-5-yl]-benzoic acid;
4-[3-(3-tert-butyl-4-ethoxy-phenyl)-[1,2,4]oxadiazol-5-yl]-benzoic acid;
4-[3-(3-tert-butyl-4-propoxy-phenyl)-[1,2,4]oxadiazol-5-yl]-benzoic acid;
4-[3-(3-tert-butyl-4-isobutoxy-phenyl)-[1,2,4]oxadiazol-5-yl]-benzoic acid;
4-{3-[3-tert-butyl-4-(2,2,2-trifluoro-ethoxy)-phenyl]-[1,2,4]-oxadiazol-5-yl}-benzoic acid;
4-[3-(3-tert-butyl-4-cyclopropylmethoxy-phenyl)-[1,2,4]oxadiazol-5-yl]-benzoic acid;
4-{3-[3-tert-Butyl-4-(2,2-dimethoxy-ethoxy)-phenyl]-[1,2,4]-oxadiazol-5-yl}-benzoic acid;
4-[3-(3-tert-butyl-4-[1,3]dioxolan-2-ylmethoxy)-phenyl]-[1,2,4]oxadiazol-5-yl)-benzoic acid;
4-{5-[4-hydroxy-3-(1-methyl-cyclohexyl)-phenyl]-thiazol-2-yl}-benzoic acid;
4-{5-[4-isobutoxy-3-(1-methyl-cyclohexyl)-phenyl]-thiazol-2-yl}-benzoic acid;

4-{5-[4-methoxy-3-(1-methyl-cyclohexyl)-phenyl]-thiazol-2-yl}-benzoic acid;
4-{5-[3-(1-methyl-cyclohexyl)-4-propoxy-phenyl]-thiazol-2-yl}-benzoic acid,
4-{5-[4-cyclopropylmethoxy-3-(1-methyl-cyclohexyl)-phenyl]-thiazol-2-yl}-benzoic acid;
4-{5-[4-ethylcarbamoylmethoxy-3-(1-methyl-cyclohexyl)-phenyl]-thiazol-2-yl}-benzoic acid;
4-[3-(3-adamantan-1-yl-4-trimethylsilanylmethoxy-phenyl)-[1,2,4]oxadiazol-5-yl]-benzoic acid;
4-{5-[3-adamantan-1-yl-4-(2,2-dimethoxy-ethoxy)-phenyl]-[1,3,4]-oxadiazol-2-yl}-benzoic acid;
4-{5-[3-adamantan-1-yl-4-(2-methoxy-ethoxymethoxy)-phenyl]-4H-pyrazol-3-yl}-benzoic acid;
4-[5-(3-adamantan-1-yl-4-propylamino-phenyl)-thiazol-2-yl]-benzoic acid;
4-[5-(3-tert-butyl-4-methoxy-phenyl)-thiazol-2-yl]-benzoic acid;
4-[5-(3-tert-butyl-4-ethoxy-phenyl)-thiazol-2-yl]-benzoic acid;
4-[5-(3-tert-butyl-4-propoxy-phenyl)-thiazol-2-yl]-benzoic acid;
4-{5-[3-tert-butyl-4-(2,2,2-trifluoro-ethoxy)-phenyl]-thiazol-2-yl}-benzoic acid;
4-[5-(3-tert-butyl-4-cyclopropylmethoxy-phenyl)-thiazol-2-yl]-benzoic acid;
4-{5-[3-tert-butyl-4-(2-methoxy-ethoxy)-phenyl]-thiazol-2-yl}-benzoic acid;
4-{5-[3-tert-butyl-4-(2,2-dimethoxy-ethoxy)-phenyl]-thiazol-2-yl}-benzoic acid;
4-{5-[3-(1-methyl-cyclohexyl)-4-(2,2,2-trifluoro-ethoxy)-phenyl]-thiazol-2-yl}-benzoic acid;
4-{3-[4-methoxy-3-(1-methyl-cyclohexyl)-phenyl]-[1,2,4]-oxadiazol-5-yl}-benzoic acid;
4-{3-[3-(1-methyl-cyclohexyl)-4-propoxy-phenyl]-[1,2,4]oxadiazol-5-yl}-benzoic acid;
4-{3-[4-isobutoxy-3-(1-methyl-cyclohexyl)-phenyl]-[1,2,4]-oxadiazol-5-yl}-benzoic acid;
4-{3-[4-cyclopropylmethoxy-3-(1-methyl-cyclohexyl)-phenyl]-[1,2,4]-oxadiazol-5-yl}-benzoic acid;
4-{3-[4-(2,2-dimethoxy-ethoxy)-3-(1-methyl-cyclohexyl)-phenyl]-[1,2,4]oxadiazol-5-yl}-benzoic acid;
4-[5-(3-adamantan-1-yl-4-hydroxy-phenyl)-4H-pyrazol-3-yl]-benzoic acid;
4-[3-(3-adamantan-1-yl-4-cyclopropylmethoxy-phenyl)-isoxazol-5-yl]-benzoic acid;
4-[3-(3-adamantan-1-yl-4-propoxy-phenyl)-isoxazol-5-yl]-benzoic acid;
4-[3-(3-adamantan-1-yl-4-isobutoxy-phenyl)-isoxazol-5-yl]-benzoic acid;
4-{3-[3-adamantan-1-yl-4-(2,2-dimethoxy-ethoxy)-phenyl]-isoxazol-5-yl}-benzoic acid,
4-[5-(3-tert-butyl-4-ethylcarbamoylmethoxy-phenyl)-thiazol-2-yl]-benzoic acid;
4-[5-(3-tert-butyl-4-isobutoxy-phenyl)-thiazol-2-yl]-benzoic acid;
4-[3-(3-adamantan-1-yl-4-ethoxy-phenyl)-isoxazol-5-yl]-benzoic acid;
4-{5-[3-adamantan-1-yl-4-([1,3]dioxolan-2-ylmethoxy)-phenyl]-[1,3,4]oxadiazol-2-yl}-benzoic acid;
4-{3-[3-(1-methylcyclohexyl)-4-(2,2,2-trifluoroethoxy)-phenyl]-[1,2,4]oxadiazol-5-yl}-benzoic acid;
4-{3-[4-([1,3]dioxolan-2-ylmethoxy)-3-(1-methylcyclohexyl)-phenyl]-[1,2,4]oxadiazol-5-yl}-benzoic acid;
4-[5-(3-adamantan-1-yl-4-propylamino-phenyl)-thiazol-2-yl]-benzoic acid;
4-{3-[3-tert-butyl-4-(2-hydroxy-ethoxy)-phenyl]-[1,2,4]-oxadiazol-5-yl}-benzoic acid;
4-{3-[3-tert-butyl-4-(3-hydroxy-propoxy)-phenyl]-[1,2,4]-oxadiazol-5-yl}-benzoic acid;
4-[5-(3-tert-butyl-4-propoxy-phenyl)-1-methyl-1H-imidazol-2-yl]-benzoic acid;
4-[5-(4-allyloxy-3-tert-butyl-phenyl)-[1,3,4]thiadiazol-2-yl]-benzoic acid;
4-{4-[3-(1-methyl-cyclohexyl)-4-(pyridin-4-ylmethoxy)-phenyl]-oxazol-2-yl}-benzoic acid;
4-[5-(4-ethoxy-3-pyrrolidin-1-yl-phenyl)-4H-[1,2,4]triazol-3-yl]-benzoic acid;
4-{5-[3-diethylamino-4-(4-fluoro-benzyloxy)-phenyl]-[1,3,4]-thiadiazol-2-yl}-benzoic acid;
4-[5-(3-tert-butyl-4-isobutoxy-phenyl)-[1,3,4]thiadiazol-2-yl]-benzoic acid;
methyl 4-[3-(3-tert-butyl-4-hydroxy-phenyl)-[1,2,4]oxadiazol-5-yl]-benzoate;
4-[5-(4-butoxy-3-tert-butyl-phenyl)-1-methyl-1H-pyrrol-2-yl]-benzoic acid;
4-{5-[4-(2-amino-ethoxy)-3-tert-butyl-phenyl]-thiophen-2-yl}-benzoic acid;
4-{3-[3-tert-butyl-4-((E)-propenyl)-phenyl]-[1,2,4]oxadiazol-5-yl}-benzoic acid;
4-[3-(3-tert-butyl-4-propyl-phenyl)-[1,2,4]oxadiazol-5-yl]-benzoic acid;
4-[5-(3-tert-butyl-4-ethylsulfanyl-phenyl)-thiazol-2-yl]-benzoic acid;
4-[5-(3-tert-butyl-4-cyclopropylmethylsulfanyl-phenyl)-oxazol-2-yl]-benzoic acid;
4-[3-(4-cyclopropylmethoxy-3-pyrrolidin-1-yl-phenyl)-[1,2,4]oxadiazol-5-yl]-benzoic acid;
4-[3-(4-hydroxy-3-pyrrolidin-1-yl-phenyl)-[1,2,4]oxadiazol-5-yl]-benzoic acid;
4-{3-[4-(2-hydroxy-ethoxy)-3-pyrrolidin-1-yl-phenyl]-[1,2,4]oxadiazol-5-yl}-benzoic acid;
3-[5-(3-adamantan-1-yl-4-hydroxy-phenyl)-2-ethyl-2H-pyrazol-3-yl]-benzoic acid;
4-{3-[4-diethylamino-3-(3-hydroxy-propoxy)-phenyl]-[1,2,4]-oxadiazol-5-yl}-benzoic acid;
4-[3-(4-diethylamino-3-propoxy-phenyl)-isoxazol-5-yl]-benzoic acid;
4-[3-(4-tert-butyl-3-ethylamino-phenyl)-[1,2,4]oxadiazol-5-yl]-benzoic acid;
4-(2-[3-(1-methyl-cyclohexyl)-4-(pyridin-4-ylmethoxy)-phenyl]-oxazol-4-yl}-benzoic acid;
4-[2-(3-tert-butyl-4-cyclopropylmethylsulfanyl-phenyl)-oxazol-5-yl]-benzoic acid;
4-[5-(3-tert-butyl-4-hydroxy-phenyl)-[1,3,4]oxadiazol-2-yl]-benzoic acid;
4-[5-(3-tert-butyl-4-ethoxy-phenyl)-[1,3,4]oxadiazol-2-yl]-benzoic acid;
4-[5-(4-hydroxy-3-pyrrolidin-1-yl-phenyl)-[1,3,4]oxadiazol-2-yl]-benzoic acid;
methyl 4-[5-(4-hydroxy-3-pyrrolidin-1-yl-phenyl)-[1,3,4]oxadiazol-2-yl]-benzoate; and
methyl 4-[3-(4-tert-butyl-3-ethylamino-phenyl)-[1,2,4]oxadiazol-5-yl]-benzoate or pharmaceutically acceptable salts thereof.

11. The compound of claim 10 selected from the group consisting of:
4-{5-[4-hydroxy-3-(1-methyl-cyclohexyl)-phenyl]-thiazol-2-yl}-benzoic acid;
4-[5-(3-adamantan-1-yl-4-ethoxymethoxy-phenyl)-thiazol-2-yl]-benzoic acid;
4-[3-(3-tert-butyl-4-cyclopropylmethoxy-phenyl)-[1,2,4]oxadiazol-5-yl]-benzoic acid;

4-[3-(3-tert-butyl-4-methoxy-phenyl)-[1,2,4]oxadiazol-5-yl]-benzoic acid;

4-[3-(3-tert-butyl-4-ethoxy-phenyl)-[1,2,4]oxadiazol-5-yl]-benzoic acid;

4-[3-(3-tert-butyl-4-propoxy-phenyl)-[1,2,4]oxadiazol-5-yl]-benzoic acid;

4-[3-(3-tert-butyl-4-isobutoxy-phenyl)-[1,2,4]oxadiazol-5-yl]-benzoic acid; and

4-[3-(3-tert-butyl-4-hydroxy-phenyl)-[1,2,4]oxadiazol-5-yl]-benzoic acid or pharmaceutically acceptable salts thereof.

12. A compound of formula (I)

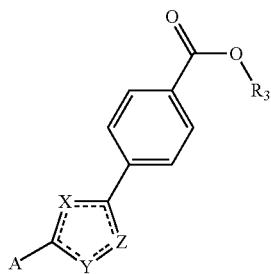

(I)

wherein:

A represents:

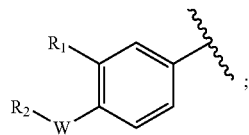

$R_1$ represents a linear or branched alkyl radical, a substituted alkyl radical, a cycloalkyl radical, a substituted cycloalkyl radical, an adamantyl radical, or an $NR_4R_5$ radical;

$R_2$ is a hydrogen atom, a linear or branched alkyl radical, a substituted alkyl radical, a fluorinated alkyl radical, an alkenyl radical, a substituted alkenyl radical, an alkynyl radical, a substituted alkynyl radical, a cycloalkyl-alkyl radical, a polyether radical, a mono or polyhydroxyalkyl radical, an aminoalkyl radical, an aralkyl radical, a substituted aralkyl radical, a heteroaralkyl radical, or a substituted heteroaralkyl radical;

$R_3$ is a hydrogen or a linear or branched alkyl radical;

$R_4$ and $R_5$, identical or different, represent a hydrogen atom, a linear or branched alkyl radical, a substituted alkyl radical, an acyl radical;

$R_4$ and $R_5$ taken together can also be linked and form an optionally substituted azetidine, pyrrolidine or piperidine heterocycle with the nitrogen atom with which they are linked;

W represents O, S, or NH;

X, Y, Z, identical or different represent O or N;

the central heterocycle

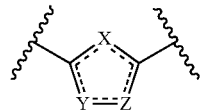

corresponds to one of the structures presented below, the dashed bonds may be a single or double bond depending on the nature of atoms X, Y and Z and their covalence

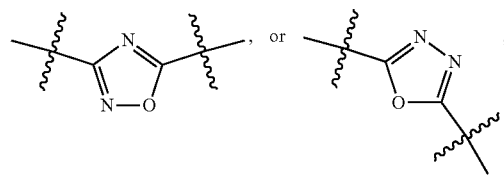

as well as their addition salts with a pharmaceutically acceptable acid, their addition salts with a pharmaceutically acceptable base and their enantiomers.

13. The compound as defined by claim 12, wherein:

A represents:

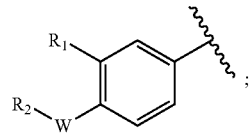

$R_1$ represents a linear or branched alkyl radical, a substituted cycloalkyl radical, an adamantyl radical, or an $NR_4R_5$ radical;

$R_2$ is a hydrogen atom, a linear or branched alkyl radical, a polyether radical, or a mono or polyhydroxyalkyl radical;

$R_3$ is a hydrogen;

$R_4$ and $R_5$, identical or different, represent a linear or branched alkyl radical, a substituted alkyl radical, an acyl radical; or $R_4$ and $R_5$ taken together can also be linked and form an optionally substituted azetidine, pyrrolidine or piperidine heterocycle with the nitrogen atom with which they are linked;

X is O; and the central heterocycle is

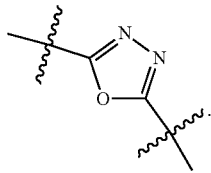 [SMILES: *c1nnc(*)o1]

14. The compound as defined by claim 12, wherein:
A represents:

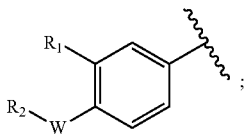

R₁ represents a branched alkyl radical, a substituted cycloalkyl radical, or an NR₄R₅ radical;
R₂ is a hydrogen atom, a linear or branched alkyl radical, a polyether radical, or a mono or polyhydroxyalkyl radical;
R₃ is a hydrogen;
R₄ and R₅, identical or different, represent a linear or branched alkyl radical, a substituted alkyl radical, an acyl radical; or
R₄ and R₅ taken together can also be linked and form an optionally substituted azetidine, pyrrolidine or piperidine heterocycle with the nitrogen atom with which they are linked;
X is O; and
the central heterocycle is

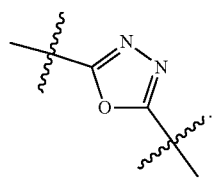 [SMILES: *c1nnc(*)o1]

15. The compound as defined by claim 12, wherein:
A represents:

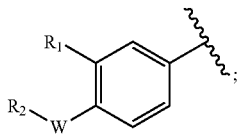

R₁ is a branched alkyl radical or an NR₄R₅ radical;
R₂ is a hydrogen atom, a linear or branched alkyl radical, or a monohydroxyalkyl radical,
R₃ is a hydrogen atom;
R₄ and R₅, identical or different, represent a linear or branched alkyl radical; or
R₄ and R₅ taken together can also be linked and form an optionally substituted pyrrolidine heterocycle with the nitrogen atom with which they are linked; and
X is O; and
the central heterocycle is an oxadiazole

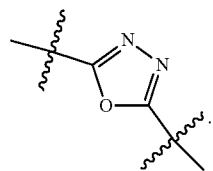 [SMILES: *c1nnc(*)o1]

16. The compound as defined by claim 12, wherein:
A represents:

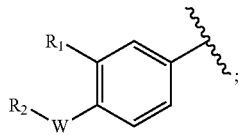

R₁ represents a branched alkyl radical or a substituted cycloalkyl radical;
R₂ is a hydrogen atom, a linear alkyl radical, or an alkyl radical substituted with an alkoxyl radical;
R3 is a hydrogen; and
wherein the central heterocycle

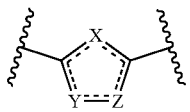

is an oxadiazolyl radical.
17. The compound as defined by claim 12, wherein:
A represents:

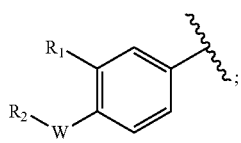

R₁ is a tert-butyl or 1-methyl-cyclohexyl radical;
R₂ is an ethoxymethyl radical;
W is O;
R₃ is a hydrogen; and
X represents N, Y represents N, and Z represents O.
18. A compound selected from the group consisting of:
4-[3-(3-adamantan-1-yl-4-ethoxymethoxy-phenyl)-[1,2,4]oxadiazol-5-yl]-benzoic acid;
4-{5-[3-adamantan-1-yl-4-(2-methoxy-ethoxymethoxy)-phenyl]-[1,3,4]-oxadiazol-2-yl}-benzoic acid;
4-[3-(3-adamantan-1-yl-4-hydroxy-phenyl)-[1,2,4]oxadiazol-5-yl]-benzoic acid;
4-[5-(3-adamantan-1-yl-4-hydroxy-phenyl)-[1,3,4]oxadiazol-2-yl]-benzoic acid;
4-[5-(3-adamantan-1-yl-4-isobutoxy-phenyl)-[1,3,4]oxadiazol-2-yl]-benzoic acid;
4-{3-[3-adamantan-1-yl-4-(2-methoxy-ethoxy)-phenyl]-[1,2,4]oxadiazol-5-yl}-benzoic acid;
4-{3-[3-adamantan-1-yl-4-(2-dimethylamino-ethoxy)-phenyl]-[1,2,4]oxadiazol-5-yl}-benzoic acid;
4-[3-(3-adamantan-1-yl-4-methoxy-phenyl)-[1,2,4]oxadiazol-5-yl]-benzoic acid;
4-[3-(3-adamantan-1-yl-4-ethoxy-phenyl)-[1,2,4]oxadiazol-5-yl]-benzoic acid;
4-[3-(3-adamantan-1-yl-4-propoxy-phenyl)-[1,2,4]oxadiazol-5-yl]-benzoic acid;
4-[3-(3-adamantan-1-yl-4-isobutoxy-phenyl)-[1,2,4]oxadiazol-5-yl]-benzoic acid;
4-{3-[3-adamantan-1-yl-4-(2,2-dimethoxy-ethoxy)-phenyl]-[1,2,4]oxadiazol-5-yl}-benzoic acid;

4-[3-(3-tert-butyl-4-ethoxymethoxy-phenyl)-[1,2,4]ox-
adiazol-5-yl]-benzoic acid;
4-[5-(3-adamantan-1-yl-4-methoxy-phenyl)-[1,3,4]ox-
adiazol-2-yl]-benzoic acid;
4-[5-(3-adamantan-1-yl-4-ethoxy-phenyl)-[1,3,4]oxadi-
azol-2-yl]-benzoic acid;
4-[5-(3-adamantan-1-yl-4-cyclopropylmethoxy-phenyl)-
[1,3,4]oxadiazol-2-yl]-benzoic acid;
4-{5-[3-adamantan-1-yl-4-(2,2,2-trifluoro-ethoxy)-phe-
nyl]-[1,3,4]oxadiazol-2-yl}-benzoic acid;
4-[5-(3-adamantan-1-yl-4-propoxy-phenyl)-[1,3,4]oxadi-
azol-2-yl]-benzoic acid;
4-[3-(3-tert-butyl-4-hydroxy-phenyl)-[1,2,4]oxadiazol-5-
yl]-benzoic acid;
4-{3-[4-ethoxymethoxy-3-(1-methyl-cyclohexyl)-phe-
nyl]-[1,2,4]oxadiazol-5-yl}-benzoic acid;
4-{3-[4-hydroxy-3-(1-methyl-cyclohexyl)-phenyl]-[1,2,
4]oxadiazol-5-yl}-benzoic acid;
4-{3-[3-tert-butyl-4-(2-methoxy-ethoxy)-phenyl]-[1,2,4]
oxadiazol-5-yl}-benzoic acid;
4-{3-[3-tert-butyl-4-(2-dimethylamino-ethoxy)-phenyl]-
[1,2,4]oxadiazol-5-yl}-benzoic acid;
4-[3-(3-tert-butyl-4-methoxy-phenyl)-[1,2,4]oxadiazol-5-
yl]-benzoic acid;
4-[3-(3-tert-butyl-4-ethoxy-phenyl)-[1,2,4]oxadiazol-5-
yl]-benzoic acid;
4-[3-(3-tert-butyl-4-propoxy-phenyl)-[1,2,4]oxadiazol-5-
yl]-benzoic acid;
4-[3-(3-tert-butyl-4-isobutoxy-phenyl)-[1,2,4]oxadiazol-
5-yl]-benzoic acid;
4-{3-[3-tert-butyl-4-(2,2,2-trifluoro-ethoxy)-phenyl]-[1,
2,4]oxadiazol-5-yl}-benzoic acid;
4-[3-(3-tert-butyl-4-cyclopropylmethoxy-phenyl)-[1,2,4]
oxadiazol-5-yl]-benzoic acid;
4-{3-[3-tert-butyl-4-(2,2-dimethoxy-ethoxy)-phenyl]-[1,
2,4]oxadiazol-5-yl}-benzoic acid;
4-{3-[3-tert-butyl-4-([1,3]dioxolan-2-ylmethoxy)-phe-
nyl]-[1,2,4]oxadiazol-5-yl}-benzoic acid;
4-[3-(3-adamantan-1-yl-4-trimethylsilanylmethoxy-phe-
nyl)-[1,2,4]oxadiazol-5-yl]-benzoic acid;
4-{5-[3-adamantan-1-yl-4-(2,2-dimethoxy-ethoxy)-phe-
nyl]-[1,3,4]oxadiazol-2-yl}-benzoic acid;
4-{3-[4-methoxy-3-(1-methyl-cyclohexyl)-phenyl]-[1,2,
4]oxadiazol-5-yl}-benzoic acid;
4-{3-[3-(1-methyl-cyclohexyl)-4-propoxy-phenyl]-[1,2,
4]oxadiazol-5-yl}-benzoic acid;
4-{3-[4-isobutoxy-3-(1-methyl-cyclohexyl)-phenyl]-[1,2,
4]oxadiazol-5-yl}-benzoic acid;
4-{3-[4-cyclopropylmethoxy-3-(1-methyl-cyclohexyl)-
phenyl]-[1,2,4]-oxadiazol-5-yl}-benzoic acid;
4-{3-[4-(2,2-dimethoxy-ethoxy)-3-(1-methyl-cyclo-
hexyl)-phenyl]-[1,2,4]oxadiazol-5-yl}-benzoic acid;
4-{5-[3-adamantan-1-yl-4-([1,3]dioxolan-2-ylmethoxy)-
phenyl]-[1,3,4]oxadiazol-2-yl}benzoique;
4-{3-[3-(1-methyl-cyclohexyl)-4-(2,2,2-trifluoro-
ethoxy)-phenyl]-[1,2,4]oxadiazol-5-yl}-benzoic acid;
4-{3-[4-([1,3]dioxolan-2-ylmethoxy)-3-(1-methylcyclo-
hexyl)-phenyl]-[1,2,4]oxadiazol-5-yl}-benzoic acid;
4-{3-[3-tert-butyl-4-(2-hydroxy-ethoxy)-phenyl]-[1,2,4]
oxadiazol-5-yl}-benzoic acid;
4-{3-[3-tert-butyl-4-(3-hydroxy-propoxy)-phenyl]-[1,2,
4]oxadiazol-5-yl}-benzoic acid;
methyl 4-[3-(3-tert-butyl-4-hydroxy-phenyl)-[1,2,4]ox-
adiazol-5-yl]-benzoate;
4-{3-[3-tert-butyl-4-((E)-propenyl)-phenyl]-[1,2,4]oxadi-
azol-5-yl}-benzoic acid;

4-[3-(3-tert-butyl-4-propyl-phenyl)-[1,2,4]oxadiazol-5-
yl]-benzoic acid;
4-[3-(4-cyclopropylmethoxy-3-pyrrolidin-1-yl-phenyl)-
[1,2,4]oxadiazol-5-yl]-benzoic acid;
4-[3-(4-hydroxy-3-pyrrolidin-1-yl-phenyl)-[1,2,4]oxadi-
azol-5-yl]-benzoic acid;
4-{3-[4-(2-hydroxy-ethoxy)-3-pyrrolidin-1-yl-phenyl]-
[1,2,4]oxadiazol-5-yl}-benzoic acid;
4-{3-[4-diethylamino-3-(3-hydroxy-propoxy)-phenyl]-
[1,2,4]oxadiazol-5-yl}-benzoic acid;
4-[3-(4-tert-butyl-3-ethylamino-phenyl)-[1,2,4]oxadi-
azol-5-yl]-benzoic acid;
4-[5-(3-tert-butyl-4-hydroxy-phenyl)-[1,3,4]oxadiazol-2-
yl]-benzoic acid;
4-[5-(3-tert-butyl-4-ethoxy-phenyl)-[1,3,4]oxadiazol-2-
yl]-benzoic acid;
4-[5-(4-hydroxy-3-pyrrolidin-1-yl-phenyl)-[1,3,4]oxadi-
azol-2-yl]-benzoic;
methyl 4-[5-(4-hydroxy-3-pyrrolidin-1-yl-phenyl)-[1,3,4]
oxadiazol-2-yl]-benzoate; and
methyl 4-[3-(4-tert-butyl-3-ethylamino-phenyl)-[1,2,4]
oxadiazol-5-yl]-benzoate or pharmaceutically accept-
able salts thereof.
19. The compound as defined by claim 12, wherein the
compound is selected from the group consisting of:
4-[3-(3-tert-butyl-4-ethoxymethoxy-phenyl)-[1,2,4]ox-
adiazol-5-yl]-benzoic acid;
4-[3-(3-tert-butyl-4-hydroxy-phenyl)-[1,2,4]oxadiazol-5-
yl]-benzoic acid;
4-{3-[4-ethoxymethoxy-3-(1-methyl-cyclohexyl)-phe-
nyl]-[1,2,4]oxadiazol-5-yl}-benzoic acid; and
4-[3-(3-tert-butyl-4-ethoxy-phenyl)-[1,2,4]oxadiazol-5-
yl]-benzoic acid or pharmaceutically acceptable salts
thereof.
20. A pharmaceutical composition comprising the com-
pound as defined by claim 12.
21. A medicament comprising an effective amount of the
compound as defined by claim 12.
22. The compound as defined by claim 1, wherein the
compound is 4-[3-(3-tert-butyl-4-hydroxy-phenyl)-[1,2,4]
oxadiazol-5-yl]-benzoic acid or a pharmaceutically accept-
able salt thereof.
23. The compound as defined by claim 1, wherein the
compound is 4-[3-(3-tert-butyl-4-methoxy-phenyl)-[1,2,4]
oxadiazol-5-yl]-benzoic acid or a pharmaceutically accept-
able salt thereof.
24. The compound as defined by claim 1, wherein the
compound is 4-{5-[4-hydroxy-3-(1-methyl-cyclohexyl)-
phenyl]-thiazol-2-yl}-benzoic acid or a pharmaceutically
acceptable salt thereof.
25. The compound as defined by claim 10, wherein the
compound is 4-[3-(3-tert-butyl-4-cyclopropylmethoxy-phe-
nyl)-[1,2,4]oxadiazol-5-yl]-benzoic acid or a pharmaceuti-
cally acceptable salt thereof.
26. The compound as defined by claim 1, wherein the
compound is 4-[3-(3-tert-butyl-4-ethoxy-phenyl)-[1,2,4]ox-
adiazol-5-yl]-benzoic acid or a pharmaceutically acceptable
salt thereof.
27. The compound as defined by claim 1, wherein the
compound is 4-[3-(3-tert-butyl-4-propoxy-phenyl)-[1,2,4]
oxadiazol-5-yl]-benzoic acid or a pharmaceutically accept-
able salt thereof.
28. The compound as defined by claim 1, wherein the
compound is 4-[3-(3-tert-butyl-4-isobutoxy-phenyl)-[1,2,4]
oxadiazol-5-yl]-benzoic acid or a pharmaceutically accept-
able salt thereof.

29. The compound as defined by claim 10, wherein the compound is 4-[5-(3-adamantan-1-yl-4-ethoxymethoxy-phenyl)-thiazol-2-yl]-benzoic acid or a pharmaceutically acceptable salt thereof.

* * * * *